(12) United States Patent
Chang et al.

(10) Patent No.: US 10,668,165 B2
(45) Date of Patent: Jun. 2, 2020

(54) MOLECULAR CONSTRUCTS FOR TREATING TUMORS

(71) Applicant: Immunwork Inc., Taipei (TW)

(72) Inventors: Tse-Wen Chang, Taipei (TW); Chien-Jen Lin, Taipei (TW); Hsing-Mao Chu, Taipei (TW)

(73) Assignee: IMMUNWORK INC., Taipei (TW)

( * ) Notice: Subject to any disclaimer, the term of this patent is extended or adjusted under 35 U.S.C. 154(b) by 498 days.

(21) Appl. No.: 14/997,874

(22) Filed: Jan. 18, 2016

(65) Prior Publication Data

US 2016/0206754 A1    Jul. 21, 2016

Related U.S. Application Data

(60) Provisional application No. 62/104,405, filed on Jan. 16, 2015, provisional application No. 62/114,427, filed on Feb. 10, 2015, provisional application No. 62/137,737, filed on Mar. 24, 2015.

(51) Int. Cl.

| | | |
|---|---|---|
| *A61K 47/64* | (2017.01) | |
| *A61K 47/65* | (2017.01) | |
| *A61K 39/00* | (2006.01) | |
| *A61K 47/68* | (2017.01) | |
| *C07K 14/655* | (2006.01) | |
| *C07K 14/715* | (2006.01) | |
| *C07K 16/24* | (2006.01) | |
| *C07K 16/28* | (2006.01) | |
| *C07K 14/485* | (2006.01) | |
| *A61K 51/06* | (2006.01) | |
| *A61K 51/08* | (2006.01) | |
| *C07K 14/705* | (2006.01) | |
| *A61K 31/4745* | (2006.01) | |
| *A61K 31/537* | (2006.01) | |
| *A61K 31/739* | (2006.01) | |
| *C07K 16/32* | (2006.01) | |
| *C07K 16/18* | (2006.01) | |
| *C07K 16/22* | (2006.01) | |
| *C07K 16/46* | (2006.01) | |
| *A61K 31/397* | (2006.01) | |
| *A61K 31/4709* | (2006.01) | |
| *A61K 31/4545* | (2006.01) | |
| *A61K 47/58* | (2017.01) | |
| *A61K 47/61* | (2017.01) | |
| *A61K 47/60* | (2017.01) | |

(52) U.S. Cl.
CPC ........ *A61K 47/6803* (2017.08); *A61K 31/397* (2013.01); *A61K 31/4545* (2013.01); *A61K 31/4709* (2013.01); *A61K 31/4745* (2013.01); *A61K 31/537* (2013.01); *A61K 31/739* (2013.01); *A61K 47/58* (2017.08); *A61K 47/60* (2017.08); *A61K 47/61* (2017.08); *A61K 47/64* (2017.08); *A61K 47/6801* (2017.08); *A61K 47/6843* (2017.08); *A61K 47/6845* (2017.08); *A61K 47/6849* (2017.08); *A61K 47/6851* (2017.08); *A61K 47/6883* (2017.08); *A61K 51/065* (2013.01); *A61K 51/088* (2013.01); *C07K 14/485* (2013.01); *C07K 14/655* (2013.01); *C07K 14/705* (2013.01); *C07K 14/70578* (2013.01); *C07K 14/7151* (2013.01); *C07K 16/18* (2013.01); *C07K 16/22* (2013.01); *C07K 16/241* (2013.01); *C07K 16/244* (2013.01); *C07K 16/2803* (2013.01); *C07K 16/2809* (2013.01); *C07K 16/2818* (2013.01); *C07K 16/2863* (2013.01); *C07K 16/2875* (2013.01); *C07K 16/2887* (2013.01); *C07K 16/32* (2013.01); *C07K 16/468* (2013.01); *A61K 2039/505* (2013.01); *C07K 2317/21* (2013.01); *C07K 2317/24* (2013.01); *C07K 2317/31* (2013.01); *C07K 2317/524* (2013.01); *C07K 2317/526* (2013.01); *C07K 2317/55* (2013.01); *C07K 2317/622* (2013.01); *C07K 2317/64* (2013.01); *C07K 2317/71* (2013.01); *C07K 2317/73* (2013.01); *C07K 2317/732* (2013.01); *C07K 2317/76* (2013.01); *C07K 2317/94* (2013.01); *C07K 2319/30* (2013.01); *C07K 2319/32* (2013.01); *C07K 2319/33* (2013.01)

(58) Field of Classification Search
None
See application file for complete search history.

*Primary Examiner* — Mark Halvorson
*Assistant Examiner* — Kauser M Akhoon
(74) *Attorney, Agent, or Firm* — Muncy, Geissler, Olds & Lowe, P.C.

(57) ABSTRACT

The present disclosure provides various molecular constructs having a targeting element and an effector element. Methods for treating various diseases using such molecular constructs are also disclosed.

11 Claims, 28 Drawing Sheets
Specification includes a Sequence Listing.

```
                              SEQUENCE LISTING

<160> NUMBER OF SEQ ID NOS: 36

<210> SEQ ID NO 1
<211> LENGTH: 4
<212> TYPE: PRT
<213> ORGANISM: Artificial Sequence
<220> FEATURE:
<223> OTHER INFORMATION: filler sequence-1

<400> SEQUENCE: 1

Gly Gly Gly Ser
1

<210> SEQ ID NO 2
<211> LENGTH: 4
<212> TYPE: PRT
<213> ORGANISM: Artificial Sequence
<220> FEATURE:
<223> OTHER INFORMATION: filler sequence-2

<400> SEQUENCE: 2

Gly Ser Gly Ser
1

<210> SEQ ID NO 3
<211> LENGTH: 4
<212> TYPE: PRT
<213> ORGANISM: Artificial Sequence
<220> FEATURE:
<223> OTHER INFORMATION: filler sequence-3

<400> SEQUENCE: 3

Gly Gly Ser Gly
1

<210> SEQ ID NO 4
<211> LENGTH: 5
<212> TYPE: PRT
<213> ORGANISM: Artificial Sequence
<220> FEATURE:
<223> OTHER INFORMATION: filler sequence-4

<400> SEQUENCE: 4

Gly Ser Gly Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: filler sequence-5

<400> SEQUENCE: 5

Ser Gly Gly Ser Gly
1               5

<210> SEQ ID NO 6
<211> LENGTH: 5
<212> TYPE: PRT
<213> ORGANISM: Artificial Sequence
<220> FEATURE:
<223> OTHER INFORMATION: filler sequence-6
```

<400> SEQUENCE: 6

Gly Gly Gly Gly Ser
1               5

<210> SEQ ID NO 7
<211> LENGTH: 6
<212> TYPE: PRT
<213> ORGANISM: Artificial Sequence
<220> FEATURE:
<223> OTHER INFORMATION: filler sequence-7

<400> SEQUENCE: 7

Gly Gly Ser Gly Gly Ser
1               5

<210> SEQ ID NO 8
<211> LENGTH: 7
<212> TYPE: PRT
<213> ORGANISM: Artificial Sequence
<220> FEATURE:
<223> OTHER INFORMATION: filler sequence-8

<400> SEQUENCE: 8

Gly Gly Ser Gly Gly Ser Gly
1               5

<210> SEQ ID NO 9
<211> LENGTH: 8
<212> TYPE: PRT
<213> ORGANISM: Artificial Sequence
<220> FEATURE:
<223> OTHER INFORMATION: filler sequence-9

<400> SEQUENCE: 9

Ser Gly Ser Gly Gly Ser Gly Ser
1               5

<210> SEQ ID NO 10
<211> LENGTH: 9
<212> TYPE: PRT
<213> ORGANISM: Artificial Sequence
<220> FEATURE:
<223> OTHER INFORMATION: filler sequence-10

<400> SEQUENCE: 10

Gly Ser Gly Gly Ser Gly Ser Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: filler sequence-11

<400> SEQUENCE: 11

Ser Gly Gly Ser Gly Gly Ser Gly Ser Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: filler sequence-12

```
<400> SEQUENCE: 12

Gly Gly Ser Gly Gly Ser Gly Gly Ser Gly Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: filler sequence-13

<400> SEQUENCE: 13

Ser Gly Gly Ser Gly Gly Ser Gly Ser Gly Gly Ser
1               5                   10

<210> SEQ ID NO 14
<211> LENGTH: 13
<212> TYPE: PRT
<213> ORGANISM: Artificial Sequence
<220> FEATURE:
<223> OTHER INFORMATION: filler sequence-14

<400> SEQUENCE: 14

Gly Gly Gly Gly Ser Gly Gly Ser Gly Gly Gly Gly Ser
1               5                   10

<210> SEQ ID NO 15
<211> LENGTH: 14
<212> TYPE: PRT
<213> ORGANISM: Artificial Sequence
<220> FEATURE:
<223> OTHER INFORMATION: filler sequence-15

<400> SEQUENCE: 15

Gly Gly Gly Ser Gly Ser Gly Ser Gly Ser Gly Gly Gly Ser
1               5                   10

<210> SEQ ID NO 16
<211> LENGTH: 15
<212> TYPE: PRT
<213> ORGANISM: Artificial Sequence
<220> FEATURE:
<223> OTHER INFORMATION: filler sequence-16

<400> SEQUENCE: 16

Ser Gly Ser Gly Gly Gly Gly Gly Ser Gly Gly Ser Gly Ser Gly
1               5                   10                  15

<210> SEQ ID NO 17
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-1

<400> SEQUENCE: 17

Cys Gly Gly Ser Gly Gly Ser Gly Gly Ser Lys Gly Ser Gly Ser Lys
1               5                   10                  15

<210> SEQ ID NO 18
<211> LENGTH: 19
<212> TYPE: PRT
<213> ORGANISM: Artificial Sequence
```

```
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptitde core-2

<400> SEQUENCE: 18

Cys Gly Gly Ser Gly Gly Ser Gly Gly Ser Lys Gly Ser Gly Ser Lys
1               5                   10                  15

Gly Ser Lys

<210> SEQ ID NO 19
<211> LENGTH: 31
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide-3

<400> SEQUENCE: 19

Cys Gly Ser Lys Gly Ser Lys Gly Ser Lys Gly Ser Lys Gly Ser Lys
1               5                   10                  15

Gly Ser Lys Gly Ser Lys Gly Ser Lys Gly Ser Lys Gly Ser Lys
            20                  25                  30

<210> SEQ ID NO 20
<211> LENGTH: 8
<212> TYPE: PRT
<213> ORGANISM: Artificial Sequence
<220> FEATURE:
<223> OTHER INFORMATION: hapten

<400> SEQUENCE: 20

Trp Ala Asp Trp Pro Gly Pro Pro
1               5

<210> SEQ ID NO 21
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-4

<400> SEQUENCE: 21

Xaa Gly Gly Ser Gly Gly Ser Gly Gly Ser Lys Gly Ser Gly Ser Lys
1               5                   10                  15

<210> SEQ ID NO 22
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
```

```
<222> LOCATION: 1
<223> OTHER INFORMATION: ACETYLATION
<220> FEATURE:
<223> OTHER INFORMATION: polypeptide core-5

<400> SEQUENCE: 22

Xaa Gly Gly Ser Gly Gly Ser Gly Gly Ser Lys Gly Ser Gly Ser Lys
1               5                   10                  15

Gly Ser Lys

<210> SEQ ID NO 23
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is L-azidohomoalanine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-6

<400> SEQUENCE: 23

Xaa Gly Gly Ser Gly Gly Ser Gly Gly Ser Lys Gly Ser Gly Ser Lys
1               5                   10                  15

Gly Ser Lys

<210> SEQ ID NO 24
<211> LENGTH: 21
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-7

<400> SEQUENCE: 24

Xaa Gly Gly Ser Gly Gly Ser Gly Gly Ser Lys Gly Ser Gly Ser Lys
1               5                   10                  15

Gly Ser Gly Ser Cys
            20

<210> SEQ ID NO 25
<211> LENGTH: 7
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-8
<220> FEATURE:
<221> NAME/KEY: MOD_RES
<222> LOCATION: 2,4,6
<223> OTHER INFORMATION: Xaa is PEGylated amino acid with two EG units

<400> SEQUENCE: 25

Cys Xaa Lys Xaa Lys Xaa Lys
1               5
```

```
<210> SEQ ID NO 26
<211> LENGTH: 11
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-9
<220> FEATURE:
<221> NAME/KEY: MOD_RES
<222> LOCATION: 2,4,6,8,10
<223> OTHER INFORMATION: Xaa is PEGylated amino acid with six EG units

<400> SEQUENCE: 26

Cys Xaa Lys Xaa Lys Xaa Lys Xaa Lys Xaa Lys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: CCK analogue
<220> FEATURE:
<221> NAME/KEY: MOD_RES
<222> LOCATION: 8
<223> OTHER INFORMATION: SO4H modification
      SULFATATION
<220> FEATURE:
<221> NAME/KEY: MOD_RES
<222> LOCATION: 9,12
<223> OTHER INFORMATION: Xaa is NOR-leucine

<400> SEQUENCE: 27

Cys Gly Gly Gly Gly Ser Asp Tyr Xaa Gly Trp Xaa Asp Phe
1               5                   10

<210> SEQ ID NO 28
<211> LENGTH: 292
<212> TYPE: PRT
<213> ORGANISM: Artificial Sequence
<220> FEATURE:
<223> OTHER INFORMATION: 2-chain EGF-hIgG1.Fc

<400> SEQUENCE: 28

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg Ala Ser Gly Gly Ser Gly Gly Gly Ser Gly
    50                  55                  60

Gly Gly Gly Ser Pro Ala Pro Glu Leu Leu Gly Gly Pro Ser Val Phe
65                  70                  75                  80

Leu Phe Pro Pro Lys Pro Lys Asp Thr Leu Met Ile Ser Arg Thr Pro
                85                  90                  95

Glu Val Thr Cys Val Val Val Asp Val Ser His Glu Asp Pro Glu Val
            100                 105                 110

Lys Phe Asn Trp Tyr Val Asp Gly Val Glu Val His Asn Ala Lys Thr
        115                 120                 125

Lys Pro Arg Glu Glu Gln Tyr Asn Ser Thr Tyr Arg Val Val Ser Val
```

```
                  130                 135                 140
Leu Thr Val Leu His Gln Asp Trp Leu Asn Gly Lys Asp Tyr Lys Cys
145                 150                 155                 160

Lys Val Ser Asn Lys Ala Leu Pro Ala Pro Ile Glu Lys Thr Ile Ser
                165                 170                 175

Lys Ala Lys Gly Gln Pro Arg Glu Pro Gln Val Tyr Thr Leu Pro Pro
            180                 185                 190

Ser Arg Asp Glu Leu Thr Arg Asn Gln Val Ser Leu Thr Cys Leu Val
        195                 200                 205

Lys Gly Phe Tyr Pro Ser Asp Ile Ala Val Glu Trp Glu Ser Asn Gly
    210                 215                 220

Gln Pro Glu Asn Asn Tyr Lys Thr Thr Pro Pro Val Leu Asp Ser Asp
225                 230                 235                 240

Gly Ser Phe Phe Leu Tyr Ser Lys Leu Thr Val Asp Lys Ser Arg Trp
                245                 250                 255

Gln Gln Gly Asn Val Phe Ser Cys Ser Val Met His Glu Ala Leu His
            260                 265                 270

Asn His Tyr Thr Gln Lys Ser Leu Ser Leu Ser Pro Gly Lys Gly Gly
        275                 280                 285

Gly Gly Asp Cys
    290

<210> SEQ ID NO 29
<211> LENGTH: 540
<212> TYPE: PRT
<213> ORGANISM: Artificial Sequence
<220> FEATURE:
<223> OTHER INFORMATION: 2-chain EGF-hIgG1.Fc-anti-PD-1

<400> SEQUENCE: 29

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg Ala Ser Gly Ser Gly Gly Gly Ser Gly
    50                  55                  60

Gly Gly Gly Ser Pro Ala Pro Glu Leu Leu Gly Gly Pro Ser Val Phe
65                  70                  75                  80

Leu Phe Pro Pro Lys Pro Lys Asp Thr Leu Met Ile Ser Arg Thr Pro
                85                  90                  95

Glu Val Thr Cys Val Val Val Asp Val Ser His Glu Asp Pro Glu Val
            100                 105                 110

Lys Phe Asn Trp Tyr Val Asp Gly Val Glu Val His Asn Ala Lys Thr
        115                 120                 125

Lys Pro Arg Glu Glu Gln Tyr Asn Ser Thr Tyr Arg Val Val Ser Val
    130                 135                 140

Leu Thr Val Leu His Gln Asp Trp Leu Asn Gly Lys Asp Tyr Lys Cys
145                 150                 155                 160

Lys Val Ser Asn Lys Ala Leu Pro Ala Pro Ile Glu Lys Thr Ile Ser
                165                 170                 175

Lys Ala Lys Gly Gln Pro Arg Glu Pro Gln Val Tyr Thr Leu Pro Pro
            180                 185                 190

Ser Arg Asp Glu Leu Thr Arg Asn Gln Val Ser Leu Thr Cys Leu Val
```

```
            195                 200                 205
Lys Gly Phe Tyr Pro Ser Asp Ile Ala Val Glu Trp Glu Ser Asn Gly
    210                 215                 220

Gln Pro Glu Asn Asn Tyr Lys Thr Thr Pro Pro Val Leu Asp Ser Asp
225                 230                 235                 240

Gly Ser Phe Phe Leu Tyr Ser Lys Leu Thr Val Asp Lys Ser Arg Trp
            245                 250                 255

Gln Gln Gly Asn Val Phe Ser Cys Ser Val Met His Glu Ala Leu His
        260                 265                 270

Asn His Tyr Thr Gln Lys Ser Leu Ser Leu Ser Pro Gly Lys Gly Gly
    275                 280                 285

Gly Gly Ser Gly Gly Gly Ser Gly Gly Gly Ser Glu Ile Val
290                 295                 300

Leu Thr Gln Ser Pro Ala Thr Leu Ser Leu Ser Pro Gly Glu Arg Ala
305                 310                 315                 320

Thr Leu Ser Cys Arg Ala Ser Gln Ser Val Ser Ser Tyr Leu Ala Trp
            325                 330                 335

Tyr Gln Gln Lys Pro Gly Gln Ala Pro Arg Leu Leu Ile Tyr Asp Ala
        340                 345                 350

Ser Asn Arg Ala Thr Gly Ile Pro Ala Arg Phe Ser Gly Ser Gly Ser
    355                 360                 365

Gly Thr Asp Phe Thr Leu Thr Ile Ser Ser Leu Glu Pro Glu Asp Phe
370                 375                 380

Ala Val Tyr Tyr Cys Gln Gln Ser Ser Asn Trp Pro Arg Thr Phe Gly
385                 390                 395                 400

Gln Gly Thr Lys Val Glu Ile Lys Arg Gly Ser Thr Ser Gly Ser Gly
            405                 410                 415

Lys Pro Gly Ser Gly Glu Gly Ser Thr Lys Gly Gln Val Gln Leu Val
        420                 425                 430

Glu Ser Gly Gly Gly Val Val Gln Pro Gly Arg Ser Leu Arg Leu Asp
    435                 440                 445

Cys Lys Ala Ser Gly Ile Thr Phe Ser Asn Ser Gly Met His Trp Val
450                 455                 460

Arg Gln Ala Pro Gly Lys Gly Leu Glu Trp Val Ala Val Ile Trp Tyr
465                 470                 475                 480

Asp Gly Ser Lys Arg Tyr Tyr Ala Asp Ser Val Lys Gly Arg Phe Thr
            485                 490                 495

Ile Ser Arg Asp Asn Ser Lys Asn Thr Leu Phe Leu Gln Met Asn Ser
        500                 505                 510

Leu Arg Ala Glu Asp Thr Ala Val Tyr Tyr Cys Ala Thr Asn Asp Asp
    515                 520                 525

Tyr Trp Gly Gln Gly Thr Leu Val Thr Val Ser Ser
530                 535                 540

<210> SEQ ID NO 30
<211> LENGTH: 545
<212> TYPE: PRT
<213> ORGANISM: Artificial Sequence
<220> FEATURE:
<223> OTHER INFORMATION: 2-chain EGF-hIgG1.Fc-anti-CD3

<400> SEQUENCE: 30

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
```

```
                    20                  25                  30
    Cys Val Val Gly Tyr Ile Gly Glu Arg Cys Gln Tyr Arg Asp Leu Lys
                35                  40                  45
    Trp Trp Glu Leu Arg Ala Ser Gly Gly Ser Gly Gly Gly Gly Ser Gly
                50                  55                  60
    Gly Gly Gly Ser Pro Ala Pro Glu Leu Leu Gly Gly Pro Ser Val Phe
    65                  70                  75                  80
    Leu Phe Pro Pro Lys Pro Lys Asp Thr Leu Met Ile Ser Arg Thr Pro
                    85                  90                  95
    Glu Val Thr Cys Val Val Val Asp Val Ser His Glu Asp Pro Glu Val
                    100                 105                 110
    Lys Phe Asn Trp Tyr Val Asp Gly Val Glu Val His Asn Ala Lys Thr
                    115                 120                 125
    Lys Pro Arg Glu Glu Gln Tyr Asn Ser Thr Tyr Arg Val Val Ser Val
                    130                 135                 140
    Leu Thr Val Leu His Gln Asp Trp Leu Asn Gly Lys Asp Tyr Lys Cys
    145                 150                 155                 160
    Lys Val Ser Asn Lys Ala Leu Pro Ala Pro Ile Glu Lys Thr Ile Ser
                    165                 170                 175
    Lys Ala Lys Gly Gln Pro Arg Glu Pro Gln Val Tyr Thr Leu Pro Pro
                    180                 185                 190
    Ser Arg Asp Glu Leu Thr Arg Asn Gln Val Ser Leu Thr Cys Leu Val
                    195                 200                 205
    Lys Gly Phe Tyr Pro Ser Asp Ile Ala Val Glu Trp Glu Ser Asn Gly
                    210                 215                 220
    Gln Pro Glu Asn Asn Tyr Lys Thr Thr Pro Pro Val Leu Asp Ser Asp
    225                 230                 235                 240
    Gly Ser Phe Phe Leu Tyr Ser Lys Leu Thr Val Asp Lys Ser Arg Trp
                    245                 250                 255
    Gln Gln Gly Asn Val Phe Ser Cys Ser Val Met His Glu Ala Leu His
                    260                 265                 270
    Asn His Tyr Thr Gln Lys Ser Leu Ser Leu Ser Pro Gly Lys Gly Gly
                    275                 280                 285
    Gly Gly Ser Gly Gly Gly Ser Gly Gly Gly Gly Ser Asp Ile Gln
                    290                 295                 300
    Met Thr Gln Ser Pro Ser Ser Leu Ser Ala Ser Val Gly Asp Arg Val
    305                 310                 315                 320
    Thr Ile Thr Cys Ser Ala Ser Ser Val Ser Tyr Met Asn Trp Tyr
                    325                 330                 335
    Gln Gln Thr Pro Gly Lys Ala Pro Lys Arg Trp Ile Tyr Asp Thr Ser
                    340                 345                 350
    Lys Leu Ala Ser Gly Val Pro Ser Arg Phe Ser Gly Ser Gly Ser Gly
                    355                 360                 365
    Thr Asp Tyr Thr Phe Thr Ile Ser Ser Leu Gln Pro Glu Asp Ile Ala
                    370                 375                 380
    Thr Tyr Tyr Cys Gln Gln Trp Ser Ser Asn Pro Phe Thr Phe Gly Gln
    385                 390                 395                 400
    Gly Thr Lys Leu Gln Ile Thr Arg Gly Ser Thr Ser Gly Ser Gly Lys
                    405                 410                 415
    Pro Gly Ser Gly Glu Gly Ser Thr Lys Gly Gln Val Gln Leu Val Gln
                    420                 425                 430
    Ser Gly Gly Gly Val Val Gln Pro Gly Arg Ser Leu Arg Leu Ser Cys
                    435                 440                 445
```

```
Lys Ala Ser Gly Tyr Thr Phe Thr Arg Tyr Thr Met His Trp Val Arg
            450                 455                 460

Gln Ala Pro Gly Lys Gly Leu Glu Trp Ile Gly Tyr Ile Asn Pro Ser
465                 470                 475                 480

Arg Gly Tyr Thr Asn Tyr Asn Gln Lys Val Lys Asp Arg Phe Thr Ile
                    485                 490                 495

Ser Arg Asp Asn Ser Lys Asn Thr Ala Phe Leu Gln Met Asp Ser Leu
                500                 505                 510

Arg Pro Glu Asp Thr Gly Val Tyr Phe Cys Ala Arg Tyr Tyr Asp Asp
            515                 520                 525

His Tyr Cys Leu Asp Tyr Trp Gly Gln Gly Thr Pro Val Thr Val Ser
        530                 535                 540

Ser
545

<210> SEQ ID NO 31
<211> LENGTH: 292
<212> TYPE: PRT
<213> ORGANISM: Artificial Sequence
<220> FEATURE:
<223> OTHER INFORMATION: 2-chain EGF(S2W/D3V)-hIgG1.Fc

<400> SEQUENCE: 31

Asn Trp Val Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg Ala Ser Gly Gly Ser Gly Gly Gly Gly Ser Gly
    50                  55                  60

Gly Gly Ser Pro Ala Pro Glu Leu Leu Gly Gly Pro Ser Val Phe
65                  70                  75                  80

Leu Phe Pro Pro Lys Pro Lys Asp Thr Leu Met Ile Ser Arg Thr Pro
                85                  90                  95

Glu Val Thr Cys Val Val Val Asp Val Ser His Glu Asp Pro Glu Val
            100                 105                 110

Lys Phe Asn Trp Tyr Val Asp Gly Val Glu Val His Asn Ala Lys Thr
        115                 120                 125

Lys Pro Arg Glu Glu Gln Tyr Asn Ser Thr Tyr Arg Val Val Ser Val
    130                 135                 140

Leu Thr Val Leu His Gln Asp Trp Leu Asn Gly Lys Asp Tyr Lys Cys
145                 150                 155                 160

Lys Val Ser Asn Lys Ala Leu Pro Ala Pro Ile Glu Lys Thr Ile Ser
                165                 170                 175

Lys Ala Lys Gly Gln Pro Arg Glu Pro Gln Val Tyr Thr Leu Pro Pro
            180                 185                 190

Ser Arg Asp Glu Leu Thr Arg Asn Gln Val Ser Leu Thr Cys Leu Val
        195                 200                 205

Lys Gly Phe Tyr Pro Ser Asp Ile Ala Val Glu Trp Glu Ser Asn Gly
    210                 215                 220

Gln Pro Glu Asn Asn Tyr Lys Thr Thr Pro Pro Val Leu Asp Ser Asp
225                 230                 235                 240

Gly Ser Phe Phe Leu Tyr Ser Lys Leu Thr Val Asp Lys Ser Arg Trp
                245                 250                 255
```

-continued

```
Gln Gln Gly Asn Val Phe Ser Cys Ser Val Met His Glu Ala Leu His
            260                 265                 270

Asn His Tyr Thr Gln Lys Ser Leu Ser Leu Ser Pro Gly Lys Gly Gly
            275                 280                 285

Gly Gly Asp Cys
            290

<210> SEQ ID NO 32
<211> LENGTH: 540
<212> TYPE: PRT
<213> ORGANISM: Artificial Sequence
<220> FEATURE:
<223> OTHER INFORMATION: 2-chain EGF(S2W/D3V)-hIgG1.Fc-anti-PD-1

<400> SEQUENCE: 32

Asn Trp Val Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg Ala Ser Gly Gly Ser Gly Gly Gly Gly Ser Gly
    50                  55                  60

Gly Gly Ser Pro Ala Pro Glu Leu Leu Gly Gly Pro Ser Val Phe
65                  70                  75                  80

Leu Phe Pro Pro Lys Pro Lys Asp Thr Leu Met Ile Ser Arg Thr Pro
                85                  90                  95

Glu Val Thr Cys Val Val Val Asp Val Ser His Glu Asp Pro Glu Val
            100                 105                 110

Lys Phe Asn Trp Tyr Val Asp Gly Val Glu Val His Asn Ala Lys Thr
        115                 120                 125

Lys Pro Arg Glu Glu Gln Tyr Asn Ser Thr Tyr Arg Val Val Ser Val
    130                 135                 140

Leu Thr Val Leu His Gln Asp Trp Leu Asn Gly Lys Asp Tyr Lys Cys
145                 150                 155                 160

Lys Val Ser Asn Lys Ala Leu Pro Ala Pro Ile Glu Lys Thr Ile Ser
                165                 170                 175

Lys Ala Lys Gly Gln Pro Arg Glu Pro Gln Val Tyr Thr Leu Pro Pro
            180                 185                 190

Ser Arg Asp Glu Leu Thr Arg Asn Gln Val Ser Leu Thr Cys Leu Val
        195                 200                 205

Lys Gly Phe Tyr Pro Ser Asp Ile Ala Val Glu Trp Glu Ser Asn Gly
    210                 215                 220

Gln Pro Glu Asn Asn Tyr Lys Thr Thr Pro Pro Val Leu Asp Ser Asp
225                 230                 235                 240

Gly Ser Phe Phe Leu Tyr Ser Lys Leu Thr Val Asp Lys Ser Arg Trp
                245                 250                 255

Gln Gln Gly Asn Val Phe Ser Cys Ser Val Met His Glu Ala Leu His
            260                 265                 270

Asn His Tyr Thr Gln Lys Ser Leu Ser Leu Ser Pro Gly Lys Gly Gly
        275                 280                 285

Gly Gly Ser Gly Gly Gly Gly Ser Gly Gly Gly Ser Glu Ile Val
    290                 295                 300

Leu Thr Gln Ser Pro Ala Thr Leu Ser Leu Ser Pro Gly Glu Arg Ala
305                 310                 315                 320
```

Thr Leu Ser Cys Arg Ala Ser Gln Ser Val Ser Ser Tyr Leu Ala Trp
                325                 330                 335

Tyr Gln Gln Lys Pro Gly Gln Ala Pro Arg Leu Leu Ile Tyr Asp Ala
                340                 345                 350

Ser Asn Arg Ala Thr Gly Ile Pro Ala Arg Phe Ser Gly Ser Gly Ser
                355                 360                 365

Gly Thr Asp Phe Thr Leu Thr Ile Ser Ser Leu Glu Pro Glu Asp Phe
            370                 375                 380

Ala Val Tyr Tyr Cys Gln Gln Ser Ser Asn Trp Pro Arg Thr Phe Gly
385                 390                 395                 400

Gln Gly Thr Lys Val Glu Ile Lys Arg Gly Ser Thr Ser Gly Ser Gly
                405                 410                 415

Lys Pro Gly Ser Gly Glu Gly Ser Thr Lys Gly Gln Val Gln Leu Val
                420                 425                 430

Glu Ser Gly Gly Gly Val Val Gln Pro Gly Arg Ser Leu Arg Leu Asp
            435                 440                 445

Cys Lys Ala Ser Gly Ile Thr Phe Ser Asn Ser Gly Met His Trp Val
        450                 455                 460

Arg Gln Ala Pro Gly Lys Gly Leu Glu Trp Val Ala Val Ile Trp Tyr
465                 470                 475                 480

Asp Gly Ser Lys Arg Tyr Tyr Ala Asp Ser Val Lys Gly Arg Phe Thr
                485                 490                 495

Ile Ser Arg Asp Asn Ser Lys Asn Thr Leu Phe Leu Gln Met Asn Ser
                500                 505                 510

Leu Arg Ala Glu Asp Thr Ala Val Tyr Tyr Cys Ala Thr Asn Asp Asp
                515                 520                 525

Tyr Trp Gly Gln Gly Thr Leu Val Thr Val Ser Ser
                530                 535                 540

<210> SEQ ID NO 33
<211> LENGTH: 545
<212> TYPE: PRT
<213> ORGANISM: Artificial Sequence
<220> FEATURE:
<223> OTHER INFORMATION: 2-chain EGF(S2W/D3V)-hIgG1.Fc-anti-CD3

<400> SEQUENCE: 33

Asn Trp Val Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
                20                  25                  30

Cys Val Val Gly Tyr Ile Gly Glu Arg Cys Gln Tyr Arg Asp Leu Lys
            35                  40                  45

Trp Trp Glu Leu Arg Ala Ser Gly Gly Ser Gly Gly Gly Gly Ser Gly
        50                  55                  60

Gly Gly Ser Pro Ala Pro Glu Leu Leu Gly Gly Pro Ser Val Phe
65                  70                  75                  80

Leu Phe Pro Pro Lys Pro Lys Asp Thr Leu Met Ile Ser Arg Thr Pro
                85                  90                  95

Glu Val Thr Cys Val Val Val Asp Val Ser His Glu Asp Pro Glu Val
                100                 105                 110

Lys Phe Asn Trp Tyr Val Asp Gly Val Glu Val His Asn Ala Lys Thr
            115                 120                 125

Lys Pro Arg Glu Glu Gln Tyr Asn Ser Thr Tyr Arg Val Val Ser Val
        130                 135                 140

Leu Thr Val Leu His Gln Asp Trp Leu Asn Gly Lys Asp Tyr Lys Cys
145                 150                 155                 160

Lys Val Ser Asn Lys Ala Leu Pro Ala Pro Ile Glu Lys Thr Ile Ser
                165                 170                 175

Lys Ala Lys Gly Gln Pro Arg Glu Pro Gln Val Tyr Thr Leu Pro Pro
            180                 185                 190

Ser Arg Asp Glu Leu Thr Arg Asn Gln Val Ser Leu Thr Cys Leu Val
        195                 200                 205

Lys Gly Phe Tyr Pro Ser Asp Ile Ala Val Glu Trp Glu Ser Asn Gly
210                 215                 220

Gln Pro Glu Asn Asn Tyr Lys Thr Thr Pro Val Leu Asp Ser Asp
225                 230                 235                 240

Gly Ser Phe Phe Leu Tyr Ser Lys Leu Thr Val Asp Lys Ser Arg Trp
                245                 250                 255

Gln Gln Gly Asn Val Phe Ser Cys Ser Val Met His Glu Ala Leu His
            260                 265                 270

Asn His Tyr Thr Gln Lys Ser Leu Ser Leu Ser Pro Gly Lys Gly Gly
        275                 280                 285

Gly Gly Ser Gly Gly Gly Ser Gly Gly Gly Ser Asp Ile Gln
290                 295                 300

Met Thr Gln Ser Pro Ser Ser Leu Ser Ala Ser Val Gly Asp Arg Val
305                 310                 315                 320

Thr Ile Thr Cys Ser Ala Ser Ser Ser Val Ser Tyr Met Asn Trp Tyr
                325                 330                 335

Gln Gln Thr Pro Gly Lys Ala Pro Lys Arg Trp Ile Tyr Asp Thr Ser
            340                 345                 350

Lys Leu Ala Ser Gly Val Pro Ser Arg Phe Ser Gly Ser Gly Ser Gly
        355                 360                 365

Thr Asp Tyr Thr Phe Thr Ile Ser Ser Leu Gln Pro Glu Asp Ile Ala
370                 375                 380

Thr Tyr Tyr Cys Gln Gln Trp Ser Ser Asn Pro Phe Thr Phe Gly Gln
385                 390                 395                 400

Gly Thr Lys Leu Gln Ile Thr Arg Gly Ser Thr Ser Gly Ser Gly Lys
                405                 410                 415

Pro Gly Ser Gly Glu Gly Ser Thr Lys Gly Gln Val Gln Leu Val Gln
            420                 425                 430

Ser Gly Gly Gly Val Val Gln Pro Gly Arg Ser Leu Arg Leu Ser Cys
        435                 440                 445

Lys Ala Ser Gly Tyr Thr Phe Thr Arg Tyr Thr Met His Trp Val Arg
        450                 455                 460

Gln Ala Pro Gly Lys Gly Leu Glu Trp Ile Gly Tyr Ile Asn Pro Ser
465                 470                 475                 480

Arg Gly Tyr Thr Asn Tyr Asn Gln Lys Val Lys Asp Arg Phe Thr Ile
                485                 490                 495

Ser Arg Asp Asn Ser Lys Asn Thr Ala Phe Leu Gln Met Asp Ser Leu
            500                 505                 510

Arg Pro Glu Asp Thr Gly Val Tyr Phe Cys Ala Arg Tyr Tyr Asp Asp
        515                 520                 525

His Tyr Ser Leu Asp Tyr Trp Gly Gln Gly Thr Pro Val Thr Val Ser
        530                 535                 540

Ser
545

<210> SEQ ID NO 34
<211> LENGTH: 253
<212> TYPE: PRT
<213> ORGANISM: Artificial Sequence
<220> FEATURE:
<223> OTHER INFORMATION: 2-chain Somatostatin-hIgG1.Fc

<400> SEQUENCE: 34

```
Ala Gly Cys Lys Asn Phe Phe Trp Lys Thr Phe Thr Ser Cys Ala Ser
1               5                   10                  15

Gly Gly Ser Gly Gly Gly Ser Gly Gly Gly Ser Pro Ala Pro
            20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Asp Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Arg
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys Gly Gly Gly Asp Cys
                245                 250
```

<210> SEQ ID NO 35
<211> LENGTH: 501
<212> TYPE: PRT
<213> ORGANISM: Artificial Sequence
<220> FEATURE:
<223> OTHER INFORMATION: 2-chain Somatostatin-hIgG1.Fc-anti-PD-1

<400> SEQUENCE: 35

```
Ala Gly Cys Lys Asn Phe Phe Trp Lys Thr Phe Thr Ser Cys Ala Ser
1               5                   10                  15

Gly Gly Ser Gly Gly Gly Ser Gly Gly Gly Ser Pro Ala Pro
            20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
50                  55                  60
```

```
Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
            85                  90                  95

Asn Ser Thr Tyr Arg Val Val Ser Val Leu Thr Val Leu His Gln Asp
            100                 105                 110

Trp Leu Asn Gly Lys Asp Tyr Lys Cys Lys Val Ser Asn Lys Ala Leu
            115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Asp Glu Leu Thr Arg
145                 150                 155                 160

Asn Gln Val Ser Leu Thr Cys Leu Val Lys Gly Phe Tyr Pro Ser Asp
            165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
210                 215                 220

Cys Ser Val Met His Glu Ala Leu His Asn His Tyr Thr Gln Lys Ser
225                 230                 235                 240

Leu Ser Leu Ser Pro Gly Lys Gly Gly Gly Ser Gly Gly Gly Gly
            245                 250                 255

Ser Gly Gly Gly Gly Ser Glu Ile Val Leu Thr Gln Ser Pro Ala Thr
            260                 265                 270

Leu Ser Leu Ser Pro Gly Glu Arg Ala Thr Leu Ser Cys Arg Ala Ser
            275                 280                 285

Gln Ser Val Ser Ser Tyr Leu Ala Trp Tyr Gln Gln Lys Pro Gly Gln
            290                 295                 300

Ala Pro Arg Leu Leu Ile Tyr Asp Ala Ser Asn Arg Ala Thr Gly Ile
305                 310                 315                 320

Pro Ala Arg Phe Ser Gly Ser Gly Ser Gly Thr Asp Phe Thr Leu Thr
            325                 330                 335

Ile Ser Ser Leu Glu Pro Glu Asp Phe Ala Val Tyr Tyr Cys Gln Gln
            340                 345                 350

Ser Ser Asn Trp Pro Arg Thr Phe Gly Gln Gly Thr Lys Val Glu Ile
            355                 360                 365

Lys Arg Gly Ser Thr Ser Gly Ser Gly Lys Pro Gly Ser Gly Glu Gly
            370                 375                 380

Ser Thr Lys Gly Gln Val Gln Leu Val Glu Ser Gly Gly Gly Val Val
385                 390                 395                 400

Gln Pro Gly Arg Ser Leu Arg Leu Asp Cys Lys Ala Ser Gly Ile Thr
            405                 410                 415

Phe Ser Asn Ser Gly Met His Trp Val Arg Gln Ala Pro Gly Lys Gly
            420                 425                 430

Leu Glu Trp Val Ala Val Ile Trp Tyr Asp Gly Ser Lys Arg Tyr Tyr
            435                 440                 445

Ala Asp Ser Val Lys Gly Arg Phe Thr Ile Ser Arg Asp Asn Ser Lys
            450                 455                 460

Asn Thr Leu Phe Leu Gln Met Asn Ser Leu Arg Ala Glu Asp Thr Ala
465                 470                 475                 480
```

```
Val Tyr Tyr Cys Ala Thr Asn Asp Asp Tyr Trp Gly Gln Gly Thr Leu
                485                 490                 495

Val Thr Val Ser Ser
            500

<210> SEQ ID NO 36
<211> LENGTH: 506
<212> TYPE: PRT
<213> ORGANISM: Artificial Sequence
<220> FEATURE:
<223> OTHER INFORMATION: 2-chain Somatostatin-hIgG1.Fc-anti-CD3

<400> SEQUENCE: 36

Ala Gly Cys Lys Asn Phe Phe Trp Lys Thr Phe Thr Ser Cys Ala Ser
1               5                   10                  15

Gly Gly Ser Gly Gly Gly Gly Ser Gly Gly Gly Gly Ser Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Asp Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Arg
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys Gly Gly Gly Gly Ser Gly Gly Gly Gly
                245                 250                 255

Ser Gly Gly Gly Gly Ser Asp Ile Gln Met Thr Gln Ser Pro Ser Ser
            260                 265                 270

Leu Ser Ala Ser Val Gly Asp Arg Val Thr Ile Thr Cys Ser Ala Ser
        275                 280                 285

Ser Ser Val Ser Tyr Met Asn Trp Tyr Gln Gln Thr Pro Gly Lys Ala
    290                 295                 300

Pro Lys Arg Trp Ile Tyr Asp Thr Ser Lys Leu Ala Ser Gly Val Pro
305                 310                 315                 320

Ser Arg Phe Ser Gly Ser Gly Ser Gly Thr Asp Tyr Thr Phe Thr Ile
                325                 330                 335
```

-continued

```
Ser Ser Leu Gln Pro Glu Asp Ile Ala Thr Tyr Tyr Cys Gln Gln Trp
            340                 345                 350

Ser Ser Asn Pro Phe Thr Phe Gly Gln Gly Thr Lys Leu Gln Ile Thr
        355                 360                 365

Arg Gly Ser Thr Ser Gly Ser Gly Lys Pro Gly Ser Gly Glu Gly Ser
    370                 375                 380

Thr Lys Gly Gln Val Gln Leu Val Gln Ser Gly Gly Gly Val Val Gln
385                 390                 395                 400

Pro Gly Arg Ser Leu Arg Leu Ser Cys Lys Ala Ser Gly Tyr Thr Phe
                405                 410                 415

Thr Arg Tyr Thr Met His Trp Val Arg Gln Ala Pro Gly Lys Gly Leu
                420                 425                 430

Glu Trp Ile Gly Tyr Ile Asn Pro Ser Arg Gly Tyr Thr Asn Tyr Asn
            435                 440                 445

Gln Lys Val Lys Asp Arg Phe Thr Ile Ser Arg Asp Asn Ser Lys Asn
        450                 455                 460

Thr Ala Phe Leu Gln Met Asp Ser Leu Arg Pro Glu Asp Thr Gly Val
465                 470                 475                 480

Tyr Phe Cys Ala Arg Tyr Tyr Asp Asp His Tyr Cys Leu Asp Tyr Trp
                485                 490                 495

Gly Gln Gly Thr Pro Val Thr Val Ser Ser
                500                 505
```

MOLECULAR CONSTRUCTS FOR TREATING TUMORS

CROSS-REFERENCE TO RELATED APPLICATIONS

This application relates to and claims the benefit of U.S. Provisional Application No. 62/104,405, filed Jan. 16, 2015, U.S. Provisional Application No. 62/114,427, filed Feb. 10, 2015, and U.S. Provisional Application No. 62/137,737, filed Mar. 24, 2015; the contents of the applications are incorporated herein by reference in their entirety.

BACKGROUND OF THE INVENTION

1. Field of the Invention

The present disclosure relates to the field of pharmaceuticals; more particularly, to multi-functional molecular constructs, e.g., those having targeting and effector elements for delivering the effector (e.g., therapeutic drug) to targeted sites.

2. Description of the Related Art

The continual advancement of a broad array of methodologies for screening and selecting monoclonal antibodies (mAbs) for targeted antigens has helped the development of a good number of therapeutic antibodies for many diseases that were regarded as untreatable just a few years ago. According to Therapeutic Antibody Database, approximately 2,800 antibodies have been studied or are being planned for studies in human clinical trials, and approximately 80 antibodies have been approved by governmental drug regulatory agencies for clinical uses. The large amount of data on the therapeutic effects of antibodies has provided information concerning the pharmacological mechanisms how antibodies act as therapeutics.

One major pharmacologic mechanism for antibodies acting as therapeutics is that, antibodies can neutralize or trap disease-causing mediators, which may be cytokines or immune components present in the blood circulation, interstitial space, or in the lymph nodes. The neutralizing activity inhibits the interaction of the disease-causing mediators with their receptors. It should be noted that fusion proteins of the soluble receptors or the extracellular portions of receptors of cytokines and the Fc portion of IgG, which act by neutralizing the cytokines or immune factors in a similar fashion as neutralizing antibodies, have also been developed as therapeutic agents.

Several therapeutic antibodies that have been approved for clinical applications or subjected to clinical developments mediate their pharmacologic effects by binding to receptors, thereby blocking the interaction of the receptors with their ligands. For those antibody drugs, Fc-mediated mechanisms, such as antibody-dependent cellular cytotoxicity (ADCC) and complement-mediated cytolysis (CMC), are not the intended mechanisms for the antibodies.

Some therapeutic antibodies bind to certain surface antigens on target cells and render Fc-mediated functions and other mechanisms on the target cells. The most important Fc-mediated mechanisms are antibody-dependent cellular cytotoxicity (ADCC) and complement-mediated cytolysis (CMC), which both will cause the lysis of the antibody-bound target cells. Some antibodies binding to certain cell surface antigens can induce apoptosis of the bound target cells.

Antibodies can also serve as carriers of cytotoxic molecules or other therapeutic agents without the antibodies' serving obvious therapeutic effector functions. In general, those antibodies bind to "tumor-associated" antigens on target cells, but cannot cause cell lysis by themselves. Antibodies specific for CD19 and CD22 on B lymphomas are well known. For many years, those antibodies have been explored as carriers for cytotoxic agents, including radioactive nuclides with very short half-lives, such as $^{90}$Y, $^{131}$I, and $^{177}$Lu. Some antibodies have also been studied as targeting agents for liposomes loaded with cytotoxic drugs, such as doxorubicin, paclitaxel, and amphotericin B. The field of antibody drug conjugates (ADC) has experienced an explosive phase of research and development in recent years, mainly attributing to the development of extremely cytotoxic drugs, such as auristatin, maytansine, calicheamicin, and camptothecin, and of methodologies for conjugating the cytotoxic molecules onto antibody molecules. Those ADCs have been designed to target diffusive (or liquid) tumors of the blood, lymphoid system, and bone marrow, including various types of lymphomas and leukemia, expressing one or more unique CD markers. Some ADCs are also being developed for solid tumors. A few of this new generation of antibody drug conjugates have been approved for clinical uses and many are in clinical trials.

However, in the first generation of ADCs, the cytotoxic drug molecules are linked non-selectively to cysteine or lysine residues in the antibody, thereby resulting in a heterogeneous mixture of ADCs with different numbers of drug molecules per ADC. This approach leads to some safety and efficacy issues. For example, the first FDA-approved ADC, gemtuzumab ozogamicin, for treating acute myelogenous leukemia, is now withdrawn from the market due to unacceptable toxicity.

The concept and methodology for preparing antibodies with dual specificities germinated more than three decades ago. In recent year, the advancement in recombinant antibody engineering methodologies and the drive to develop improved medicine has stimulated the development bi-specific antibodies adopting a large variety of structural configurations.

For example, the bi-valent or multivalent antibodies may contain two or more antigen-binding sites. A number of methods have been reported for preparing multivalent antibodies by covalently linking three or four Fab fragments via a connecting structure. For example, antibodies have been engineered to express tandem three or four Fab repeats.

Several methods for producing multivalent antibodies by employing synthetic crosslinkers to associate, chemically, different antibodies or binding fragments have been disclosed. One approach involves chemically cross-linking three, four, and more separately Fab fragments using different linkers. Another method to produce a construct with multiple Fabs that are assembled to one-dimensional DNA scaffold was provided. Those various multivalent Ab constructs designed for binding to target molecules differ among one another in size, half-lives, flexibility in conformation, and ability to modulate the immune system. In view of the foregoing, several reports have been made for preparing molecular constructs with a fixed number of effector elements or with two or more different kinds of functional elements (e.g., at least one targeting element and at least one effector element). However, it is often difficult to build a molecular construct with a particular combination of the targeting and effector elements either using chemical synthesis or recombinant technology. Accordingly, there exists a need in the related art to provide novel molecular platforms to build a more versatile molecule suitable for covering applications in a wide range of diseases.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In a first aspect, the present disclosure is directed to an Fc-based molecular construct that has at least one targeting element and at least one effector element linked, directly or indirectly, to a CH2-CH3 domain of an immunoglobulin. By selecting the effector element(s) and targeting element(s) of the present Fc-based molecular construct, the molecular construct can be used to treat various cellular proliferative diseases, including diffused tumors and solid tumors. The present disclosure is also advantageous in that, in some embodiments, it utilizes the linker unit according to embodiments of the present disclosure, which provides a facile means for controlling the amount of the drug (e.g., cytotoxic drugs) payload of the present Fc-based molecular construct. The linker unit carrying multiple drug molecules is herein referred to as a drug bundle. Such drug bundles can be manufactured separately before being conjugated to the antibody molecules, thus avoiding subjecting drug molecules under harsh chemical conditions for the direct conjugation with the antibody molecules.

According to various embodiments of the present disclosure, the Fc-based molecular construct comprises a pair of CH2-CH3 segments of an IgG.Fc, a first pair of effector elements, and a first pair of targeting elements.

For a first series of Fc-based molecular constructs according to this aspect, each effector element of the first pair of effector elements is a drug bundle, while each targeting element of the first pair of targeting elements is an antibody fragment specific for a cell surface antigen. In these cases, the first pair of effector elements is linked to the C-termini of the pair of CH2-CH3 segments, whereas the first pair of targeting elements is linked to the N-termini of the pair of CH2-CH3 segments. According to various embodiments of the present disclosure, the drug bundle comprises a plurality of cytotoxic drug molecules, such as, auristatin, maytansine, doxorubicin, calicheamicin, and camptothecin; while the cell surface antigen targeted by these Fc-based molecular construct is CD5, CD19, CD20, CD22, CD23, CD30, CD33, CD34, CD37, CD38, CD43, CD78, CD79a, CD79b, CD138, or CD319. As an example, rather than a limitation, these Fc-based molecular constructs are useful in the treatment of various diffused tumors.

In a second series of Fc-based molecular constructs according to this aspect, each effector element of the first pair of effector elements is a drug bundle, while each targeting element of the first pair of targeting elements is an antibody fragment specific for a tumor-associated antigen. In these cases, the first pair of effector elements is linked to the C-termini of the pair of CH2-CH3 segments, whereas the first pair of targeting elements is linked to the N-termini of the pair of CH2-CH3 segments. According to various embodiments of the present disclosure, the drug bundle comprises a plurality of molecules of, a cytotoxic drug, a toll-like receptor (TLR) agonist, or a chelator complexed with a radioactive nuclide, whereas the tumor-associated antigen targeted by these Fc-based molecular construct is human epidermal growth factor receptor-1 (HER1), HER2, HER3, HER4, CA19-9, CA125, carcinoembryonic antigen (CEA), cell surface-associated mucin 1 (MUC1), melanoma-associated antigen (MAGE), prostate-specific membrane antigen (PSMA), prostate stem cell antigen (PSCA); mucin-related Tn, Sialyl Tn, Globo H, stage-specific embryonic antigen-4 (SSEA-4), ganglioside GD2, or epithelial cell adhesion molecule (EpCAM). As an example, but not a limitation, these Fc-based molecular constructs are useful in the treatment of various solid tumors, including malignant and/or metastatic solid tumors.

For a third series of Fc-based molecular constructs according to this aspect, each effector element of the first pair of effector elements is a drug bundle or an antibody fragment specific for a cell surface antigen, a growth factor, or a hapten; while each targeting element of the first pair of targeting elements is the growth factor or a peptide hormone. In the case where the effector elements are the drug bundles, the first pair of effector elements is respectively linked to the C-termini of the pair of CH2-CH3 segments, whereas the targeting elements are respectively linked to the N-termini of the pair of CH2-CH3 segments. Alternatively, when the effector elements are the antibody fragments, then the effector elements are respectively linked to the N-termini of the pair of CH2-CH3 segments, whereas the targeting elements are respectively linked to the C-termini of the pair of CH2-CH3 segments, and vice versa.

By selecting the effector element(s) and the targeting element(s), the Fc-based molecular constructs of this third series provided herein are also useful for use in the treatment of various solid tumors, including malignant and/or metastatic solid tumors; however, the present disclosure is not limited thereto.

According to embodiments of the present disclosure, the cytotoxic drug suitable for use as the effector elements is auristatin, maytansine, doxorubicin, calicheamicin, or camptothecin. Illustrative examples of TLR agonist include, lipopolysaccharide (LPS), monophosphoryl lipid A, motolimod, imiquimod, resiquimod, gardiquimod, CpG oligodeoxynucleotide (CpG DON), lipoteichoic acid, β-glucan, and zymosan. Chelators suitable for use herein include, but are not limited to, 1,4,7,10-Tetra-aza-cyclo-dodecane-N,N'',N''',N''''-tetraacetic acid (DOTA), 1,4,7-Triaza-cyclononane-1,4,7-triacetic acid (NOTA), 1,4,7-triazacyclooctane-1,4-diacetic acid-7-p-isothiocyanobenzyl (NODA), or diethylene triamine pentaacetic acid (DTPA). Non-limiting examples of radioactive nuclides to be complexed with the above-mentioned chelators or the like include $^{90}$Y, $^{111}$In, and $^{177}$Lu.

Some antibody fragments suitable for use as the effector elements are those specific to cell surface antigens such as programmed cell death 1 (PD-1), programmed cell death 1 ligand 1 (PD-L1), cytotoxic T-lymphocyte-associated protein 4 (CTLA-4), CD3, CD16a, CD28, and CD134. Another example is the antibody fragment specific for the growth factor like epidermal growth factor (EGF), mutant EGF, epiregulin, heparin-binding epidermal growth factor (HB-EGF), VEGF-A, basic fibroblast growth factor (bFGF), and hepatocyte growth factor (HGF). Antibody fragments specific for haptens are also suitable for use herein, and illustrative examples of haptens include dinitrophenol (DNP), trinitrophenol (TNP), dansyl, penicillin, p-aminobenzoic acid, or a polypeptide having the amino acid sequence of SEQ ID NO: 20.

As to the targeting element(s) suitable for use in this series of Fc-based molecular constructs, the targeting element(s)

may be a growth factor such as EGF, mutant EGF, epiregulin, HB-EGF, VEGF-A, bFGF, and HGF. Alternatively, the targeting element(s) may be a peptide hormone like CCK, somastatin, and TSH.

The Fc-based molecular constructs according to this aspect of the present disclosure share some common structural features, which are summarized below.

In certain embodiments, the pair of CH2-CH3 segments is derived from human IgG heavy chain γ4 or human IgG heavy chain γ1.

In some examples, the first pair of effector elements (e.g., for the third series of Fc-based molecular constructs) or the first pair of targeting elements (e.g., for the first and second series of Fc-based molecular constructs) takes a Fab configuration (i.e., comprising the $V_H$-CH1 domain and the $V_L$-CK domain); this Fab fragment is linked to the N-termini of the first and second heavy chains so that the Fc-based molecular construct adopts an IgG configuration. In these cases, the pair of elements that is not in the Fab configuration may be linked to the C-termini of the pair of CH2-CH3 segments.

According to certain embodiments, the present Fc-based molecular construct further comprises a peptide extension and a coupling arm. Specifically, the peptide extension has the sequence of $(G_{2-4}S)_{2-8}C$ and is linked to the C-terminus of one of the pair of CH2-CH3 segments. In such cases, the coupling arm is linked to the C-terminus of the coupling arm via thiol-maleimide reaction occurred therebetween. Also, before being conjugated with the drug bundle, the free terminus of the conjugating arm (that is, the terminus that is not linked to the cysteine residue) is modified with an alkyne, azide, strained alkyne, or tetrazine group, so that the drug bundle is linked thereto via inverse electron demand Diels-Alder (iEDDA) reaction or the strain-promoted azide-alkyne click chemistry (SPAAC) reaction or Copper(I)-catalyzed alkyne-azide cycloaddition (CuAAC) reaction occurred therebetween.

When the effector element is a drug bundle, the drug bundle may be provided as the linker unit according to embodiments of the present disclosure. Specifically, the drug bundle comprises a center core, a plurality of first linking arms, and optionally, a second linking arm. The center core may be a compound having a plurality of amine groups or a polypeptide comprising a plurality of lysine (K) residues, according to various embodiments of the present disclosure. Each of the first linking arms has one terminus that is linked to the center core by reacting with the amine groups of the compound core or the K residues of the polypeptide core. The first linking arm also carries a maleimide group at the free terminus thereof, wherein each of the molecules (e.g., molecules of cytotoxic drugs, TLR agonists, or chelator/radioactive nuclide complexes) is linked to the center core via connecting through the first linking arm by reacting with the maleimide group.

In the case where the center core is the polypeptide core, then the amino acid residue at the N- or C-terminus of the center core is a cysteine residue or has an azide group or an alkyne group.

For polypeptide cores with a terminal amino acid residue having the azide group or the alkyne group, the drug bundle may be linked to the peptide extension via the CuAAC reaction occurred between said terminal residue and the C-terminus of the peptide extension.

For polypeptide cores with a terminal residue that is cysteine, or for compound cores, the drug bundle further comprises the second linking arm. The second linking arm has one terminus linked to the center core by reacting with the cysteine residue of the polypeptide core or one amine group of the compound core. The second linking arm also carries an alkyne group, azide group, tetrazine group, or strained alkyne group at the free terminus thereof, so that the drug bundle can be linked to the C-terminus of the peptide extension via the CuAAC reaction or the iEDDA reaction occurred therebetween.

According to some optional embodiments of the present disclosure, the Fc-based molecular construct may further comprise a second pair of effector elements or a second pair of targeting elements.

For the second series of Fc-based molecular constructs, a second pair of targeting elements may be respectively linked to the first pair of targeting elements. For example, in certain embodiments, each effector element of the first pair of effector elements is a drug bundle comprising the plurality of molecules of the cytotoxic drug, each targeting element of the first pair of targeting elements is an scFv specific for HER2, and each targeting elements of the second pair of targeting elements is an scFv specific for HER1.

For the third series of Fc-based molecular constructs, a second pair of effector elements may be linked, in a tandem or diabody configuration, to the N-termini of the pair of elements that is linked to the N-termini of the pair of CH2-CH3 segments, thereby forming a pair of bispecific scFvs that is linked to the N-termini of the pair of CH2-CH3 segments. Alternatively, the third series of Fc-based molecular construct may further comprise a second pair of targeting elements that is linked, in a tandem or diabody configuration, to the N-termini of the pair of elements that is linked to the N-termini of the pair of CH2-CH3 segments, thereby forming a pair of bispecific scFvs that is linked to the N-termini of the pair of CH2-CH3 segments.

In a second aspect, the present disclosure is directed to methods for treating various cellular proliferative diseases. Generally, the methods involve the step of administrating an effective amount of the Fc-based molecular constructs according to the first aspect or any of the associated embodiments, to a subject in need of such treatment.

In certain embodiments, the present method is directed to the treatment of diffused tumors, such as B lymphocyte-derived lymphoma or leukemia, plasmacytoma, multiple myeloma, T-cell derived lymphoma or leukemia, and myelogenous leukemia. As discussed above, the first series of Fc-based molecular constructs of the first aspect of the present disclosure are useful in the treatment of the diffused tumor. Illustrative examples of the cell surface antigen(s) targeted by the present Fc-based molecular construct when treating a specific diffused tumor are provided in the appended claims and discussed in the description section bellow.

As discussed above, the present method is also suitable for treating solid tumors in a subject. Examples of solid tumors include, but are not limited to, melanomas, esophageal carcinomas, gastric carcinomas, brain tumor, small cell lung cancer, non-small cell lung cancer, bladder cancer, breast cancer, pancreatic cancer, renal cancer, hepatocellular carcinoma, ovary cancer, prostate cancer, thyroid cancer, testis cancer, and head and neck squamous cell carcinoma. As discussed above, the second and third series of Fc-based molecular construct of the first aspect of the present disclosure are useful in the treatment of the solid tumor. Some exemplary combination of the effector element(s) and targeting element(s) for treating solid tumors are provided in the appended claims and discussed in the description section bellow.

According to some optional embodiments of the present disclosure, when treating the solid tumor, the method comprises the steps of (a) subjecting the subject to a blood dialysis procedure using an antibody fragment specific for one or more tumor-associated antigens to remove the tumor-associated antigens that are shed from the tumor into the circulation of the subject, and then, (b) administering the Fc-based molecular construct of the present disclosure for treating the solid tumor.

In the cases where the Fc-based molecular construct uses an antibody fragment specific for a hapten as the effector element, the present method further comprises the step of administering to the subject an immunoregulatory effector that is tagged with the same hapten, after the administration of the present Fc-based molecular construct. Non-limiting examples of the immunoregulatory effector include IFN-α, IL-2, TNF-α, and IFN-γ, and an IgG antibody specific for PD-1, PD-L1, CTLA-4, and CD3.

According to some embodiments of the present disclosure, the malignant tumor that sheds one or more tumor-associated antigens into the circulation of the subject, and the method further comprises the step of, subjecting the subject to a blood dialysis procedure using an antibody fragment specific for the one or more tumor-associated antigens to remove the tumor-associated antigens that are shed from the malignant tumor, prior to the administration of the Fc-based molecular construct.

BRIEF DESCRIPTION OF THE DRAWINGS

The present description will be better understood from the following detailed description read in light of the accompanying drawings briefly discussed below.

Figure 1B:
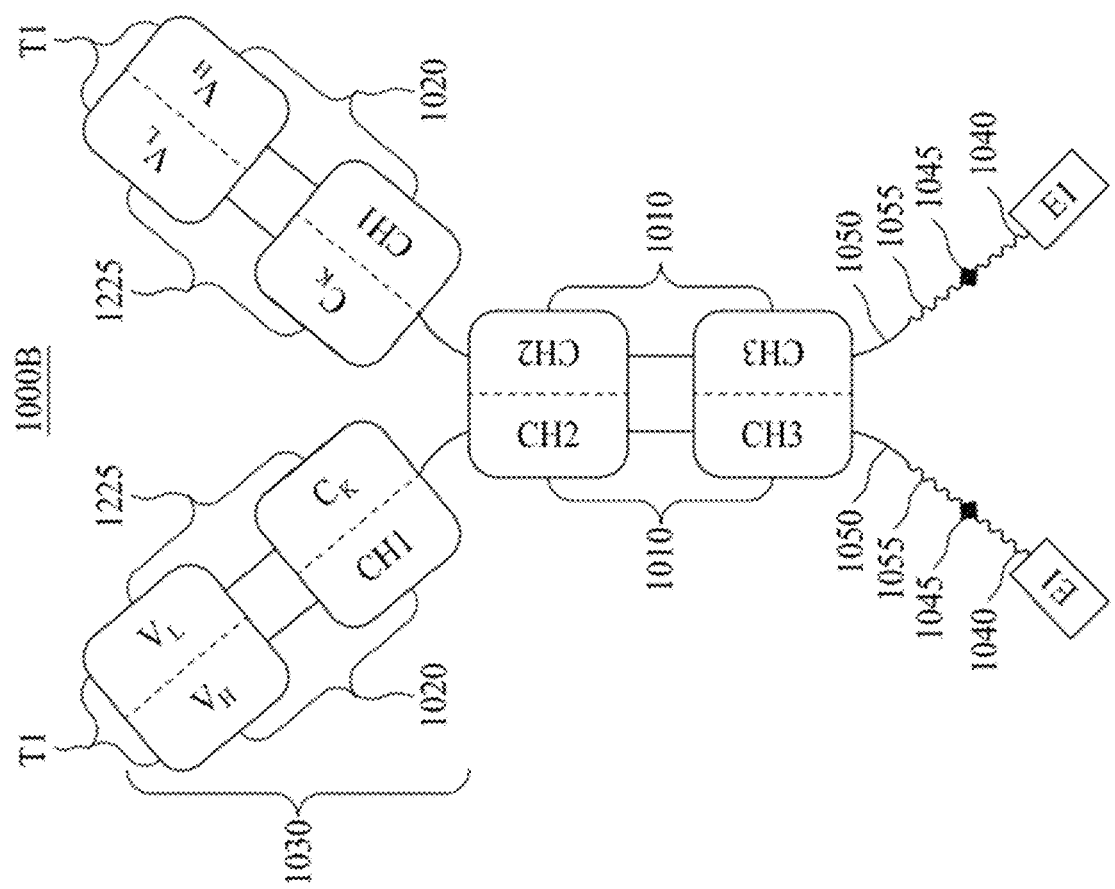
FIGS. 1A to 1C are schematic diagrams illustrating Fc-based molecular constructs according to various embodiments of the present disclosure.

In accordance with common practice, the various described features/elements are not drawn to scale but instead are drawn to best illustrate specific features/elements

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Specifically, as used herein and in the claims, the singular forms "a" and "an" include the plural reference unless the context clearly indicated otherwise. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

This present disclosure pertains generally to molecular constructs, in which each molecular construct comprises a targeting element (T) and an effector element (E), and these molecular constructs are sometimes referred to as "T-E molecules", "T-E pharmaceuticals" or "T-E drugs" in this document.

As used herein, the term "targeting element" refers to the portion of a molecular construct that directly or indirectly binds to a target of interest (e.g., a receptor on a cell surface or a protein in a tissue) thereby facilitates the transportation of the present molecular construct into the interested target. In some example, the targeting element may direct the molecular construct to the proximity of the target cell. In other cases, the targeting element specifically binds to a molecule present on the target cell surface or to a second molecule that specifically binds a molecule present on the cell surface. In some cases, the targeting element may be internalized along with the present molecular construct once it is bound to the interested target, hence is relocated into the cytosol of the target cell. A targeting element may be an antibody or a ligand for a cell surface receptor, or it may be a molecule that binds such antibody or ligand, thereby indirectly targeting the present molecular construct to the target site (e.g., the surface of the cell of choice). The localization of the effector (therapeutic agent) in the diseased site will be enhanced or favored with the present molecular constructs as compared to the therapeutic without a targeting function. The localization is a matter of degree or relative proportion; it is not meant for absolute or total localization of the effector to the diseased site.

According to the present invention, the term "effector element" refers to the portion of a molecular construct that elicits a biological activity (e.g., inducing immune responses, exerting cytotoxic effects and the like) or other functional activity (e.g., recruiting other hapten tagged therapeutic molecules), once the molecular construct is directed to its target site. The "effect" can be therapeutic or diagnostic. The effector elements encompass those that bind to cells and/or extracellular immunoregulatory factors. The effector element comprises agents such as proteins, nucleic acids, lipids, carbohydrates, glycopeptides, drug moieties (both small molecule drug and biologics), compounds, elements, and isotopes, and fragments thereof.

Although the terms, first, second, third, etc., may be used herein to describe various elements, components, regions, and/or sections, these elements (as well as components, regions, and/or sections) are not to be limited by these terms. Also, the use of such ordinal numbers does not imply a sequence or order unless clearly indicated by the context. Rather, these terms are simply used to distinguish one element from another. Thus, a first element, discussed below, could be termed a second element without departing from the teachings of the exemplary embodiments.

Here, the terms "link," "couple," and "conjugates" are used interchangeably to refer to any means of connecting two components either via direct linkage or via indirect linkage between two components.

The term "polypeptide" as used herein refers to a polymer having at least two amino acid residues. Typically, the polypeptide comprises amino acid residues ranging in length from 2 to about 200 residues; preferably, 2 to 50 residues. Where an amino acid sequence is provided herein, L-, D-, or beta amino acid versions of the sequence are also contemplated. Polypeptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an α-ester, a β-ester, a thioamide, phosphonamide, carbomate, hydroxylate, and the like.

In certain embodiments, conservative substitutions of the amino acids comprising any of the sequences described herein are contemplated. In various embodiments, one, two, three, four, or five different residues are substituted. The term "conservative substitution" is used to reflect amino acid substitutions that do not substantially alter the activity (e.g., biological or functional activity and/or specificity) of the molecule. Typically, conservative amino acid substitutions involve substitution one amino acid for another amino acid with similar chemical properties (e.g., charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are considered to be derived synthetically from the standard amino acids without sufficient change to the structure of the parent, are isomers, or are metabolite precursors.

In certain embodiments, polypeptides comprising at least 80%, preferably at least 85% or 90%, and more preferably at least 95% or 98% sequence identity with any of the sequences described herein are also contemplated.

"Percentage (%) amino acid sequence identity" with respect to the polypeptide sequences identified herein is defined as the percentage of polypeptide residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two polypeptide sequences was carried out by computer program Blastp (protein-protein BLAST) provided online by Nation Center for Biotechnology Information (NCBI). The percentage amino acid sequence identity of a given polypeptide sequence A to a given polypeptide sequence B (which can alternatively be phrased as a given polypeptide sequence A that has a certain % amino acid sequence identity to a given polypeptide sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "PEGylated amino acid" as used herein refers to a polyethylene glycol (PEG) chain with one amino group and one carboxyl group. Generally, the PEGylated amino acid has the formula of $NH_2-(CH_2CH_2O)_n-COOH$. In the present disclosure, the value of n ranges from 1 to 20; preferably, ranging from 2 to 12.

As used herein, the term "terminus" with respect to a polypeptide refers to an amino acid residue at the N- or C-end of the polypeptide. With regard to a polymer, the term "terminus" refers to a constitutional unit of the polymer (e.g., the polyethylene glycol of the present disclosure) that is positioned at the end of the polymeric backbone. In the present specification and claims, the term "free terminus" is used to mean the terminal amino acid residue or constitutional unit is not chemically bound to any other molecular.

The term "antigen" or "Ag" as used herein is defined as a molecule that elicits an immune response. This immune response may involve a secretory, humoral and/or cellular antigen-specific response. In the present disclosure, the term "antigen" can be a protein, a polypeptide (including mutants or biologically active fragments thereof), a polysaccharide, a glycoprotein, a glycolipid, a nucleic acid, or a combination thereof.

In the present specification and claims, the term "antibody" is used in the broadest sense and covers fully assembled antibodies, antibody fragments that bind with antigens, such as antigen-binding fragment (Fab/Fab'), F(ab')$_2$ fragment (having two antigen-binding Fab portions linked together by disulfide bonds), variable fragment (Fv), single chain variable fragment (scFv), bi-specific single-chain variable fragment (bi-scFv), nanobodies, unibodies and diabodies. "Antibody fragments" comprise a portion of an intact antibody, preferably the antigen-binding region or variable region of the intact antibody. Typically, an "antibody" refers to a protein consisting of one or more polypeptides substantially encoded by immunoglobulin genes or fragments of immunoglobulin genes. The well-known immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, with each pair having one "light" chain (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. According to embodiments of the present disclosure, the antibody fragment can be produced by modifying the nature antibody or by de novo synthesis using recombinant DNA methodologies. In certain embodiments of the present disclosure, the antibody and/or antibody fragment can be bispecific, and can be in various configurations. For example, bispecific antibodies may comprise two different antigen binding sites (variable regions). In various embodiments, bispecific antibodies can be produced by hybridoma technique or recombinant DNA technique. In certain embodiments, bispecific antibodies have binding specificities for at least two different epitopes.

The term "specifically binds" as used herein, refers to the ability of an antibody or an antigen-binding fragment thereof, to bind to an antigen with a dissociation constant (Kd) of no more than about $1 \times 10^{-6}$ M, $1 \times 10^{-7}$ M, $1 \times 10^{-8}$ M, $1 \times 10^{-9}$ M, $1 \times 10^{-10}$ m, $1 \times 10^{-11}$ M, M $1 \times 10^{-12}$ M, and/or to bind to an antigen with an affinity that is at least two-folds greater than its affinity to a nonspecific antigen.

The term "tumor" as used herein, refers to all neoplastic cell growth and proliferation, whether malignant or benign, and all pre-cancerous and cancerous cells and tissues. In the present specification and claims, the term "tumor" comprises solid tumors and diffused tumors.

The term "solid tumor" as used herein, denotes an abnormal mass of tissue that usually does not contain cysts or liquid areas. Different types of solid tumors are named for the type of cells that form them. Examples of solid tumors include, but are not limited to, sarcomas and carcinomas. Generally, "sarcomas" are cancers arising from connective or supporting tissues such as bone or muscle. "Carcinomas" are cancers arising from glandular cells and epithelial cells, which line body tissues.

The term "diffused tumor" as used herein refers to leukemia and/or hematological malignancy that is formed from hematopoietic (blood-forming) cells and affect blood, bone marrow, or lymph nodes. The example of the diffused tumor includes, but is not limited to, acute lymphocytic leukemia (ALL), chronic lymphocytic leukemia (CLL), acute myelogenous leukemia (AML), chronic myelogenous leukemia (CML), Hodgkin lymphoma, non-Hodgkin lymphoma, and myeloma.

The term "tumor-associated antigen" (TAA) as used herein refers to any cancer antigen that is known in the art and includes antigens found on the cancer cell surface, as well as those that are shed from cancerous cell and become soluble (i.e., soluble cancer antigens). Several cell surface antigens disposed on tumors or normal cells have soluble counterparts. Such antigens include, but are not limited to those found on cancer-associated fibroblasts (CAFs), tumor endothelial cells (TEC) and tumor-associated macrophages (TAM).

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present molecular construct or a pharmaceutical composition comprising the same to a subject, who has a medical condition a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The term "effective amount" as used herein refers to the quantity of the present recombinant protein that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of subject being treated, the duration of the treatment, the nature of concurrent therapy (if any), and the specific formulations employed and the structure of the compounds or its derivatives. Effective amount may be expressed, for example, as the total mass of active component (e.g., in grams, milligrams or micrograms) or a ratio of mass of active component to body mass, e.g., as milligrams per kilogram (mg/kg).

The terms "application" and "administration" are used interchangeably herein to mean the application of a molecular construct or a pharmaceutical composition of the present invention to a subject in need of a treatment thereof.

The terms "subject" and "patient" are used interchangeably herein and are intended to mean an animal including the human species that is treatable by the molecular construct, pharmaceutical composition, and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human.

The present disclosure is based, at least on the construction of the T-E pharmaceuticals that can be delivered to target cells, target tissues or organs at increased proportions relative to the blood circulation, lymphoid system, and other cells, tissues or organs. When this is achieved, the therapeutic effect of the pharmaceuticals is increased, while the scope and severity of the side effects and toxicity is decreased. It is also possible that a therapeutic effector is administered at a lower dosage in the form of a T-E molecule, than in a form without a targeting component. Therefore, the therapeutic effector can be administered at lower dosages without losing potency, while lowering side effects and toxicity.

Diseases that can Benefit from Better Drug Targeting

Drugs used for many diseases can be improved for better efficacy and safety, if they can be targeted to the disease sites, i.e., if they can be localized or partitioned to the disease sites more favorably than the normal tissues or organs. Following are primary examples of diseases, in which drugs can be improved if they can be preferentially distributed to the disease sites or cells.

Several classes of large numbers of therapeutic agents have been developed and experimented in animal models and in human clinical trials for the treatment of malignant tumors, including diffused and solid tumors and primary and metastatic tumors of varying clinical stages. These therapeutic agents, some of which have been approved by governmental regulatory agencies for use in patients, include (1) a large number of compounds targeting key cellular regulatory pathways or structural components, or damaging DNA or important cellular machinery, (2) antibodies specific for surface antigens of certain cell types or specific for certain tumor-associated antigens and capable of mediating apoptosis, antibody-dependent cellular cytotoxicity (ADCC), or complement-mediated cytolysis (CMC) of the targeted cells, (3) antibodies specific for certain tumor-associated antigens, which are conjugated with potent cytotoxic drugs, (4) immunoregulatory cytokines, such as such as interferon-α (IFN-α), interleukin-2 (IL-2), or interferon-γ (IFN-γ), which can activate the immune system in fighting against malignant cells, (5) antibodies targeting certain cell surface markers of B and T lymphocytes, e.g., anti-CD20 rituximab, (6) antibodies targeting growth factor receptors, e.g., anti-HER2/Neu trastuzumab and anti-EGFR cetuximab, (7) antibodies targeting vascular endothelial growth factor-A (VEGF-A) for inhibiting angiogenesis, e.g., bevacizumab, and (8) antibodies binding to immune checkpoints, such as PD1 (programmed cell death protein 1, CD279), e.g., nivolumab, PD-L1 (programmed cell death protein ligand 1, CD274), e.g., MPDL3280A, CTLA4 (cytotoxic T-lymphocyte protein 4, CD152), e.g., ipilimumab, which inhibit the negative feedback of immune reactions and allow continual activation of on-going immune responses.

The usefulness of therapeutic agents for treating cancer as well as for many other diseases is limited or compromised by their toxicity, because the agents also act on some normal cells to some degrees. Therefore, many therapeutic agents have limited therapeutic windows and therefore, in order to control their toxic effects, they are administered in many of the treated patients at suboptimal doses, as far as therapeutic efficacy is concerned, which are insufficient to achieve satisfactory therapeutic effects.

The antibody-drug conjugate approach, which is being pursued actively, requires that the tumor-targeting antibodies together with the carried cytotoxic drugs be internalized by the targeted cells expressing the tumor-associated antigens, which the targeting antibodies recognize. This requirement may potentially limit the power of the current antibody-drug conjugate approach, because cells in a tumor express a tumor-associated antigen at varying densities. Those cells expressing relatively low levels may not be killed by the current antibody-drug conjugates during treatment and will grow up as the therapeutic agents are discontinued.

I Diffused Tumor

I-(i) Targeting Cancerous Cells Originated from Leukocytes

The cancer derived from malignantly transformed cells of the lymphoid and myeloid lineages account for a significant proportion among all cancer. Those tumors are generally diffusive and not solid. Thus, the targeting of leukocyte-derived tumors will involve the targeting of the individual tumor cells. Therefore, the identification of the expression of cell-surface antigens of the tumor cells is a key in the targeting of leukocyte-derived tumors.

Tumors derived from white blood cells (leukocytes) are generally classified into three categories: (1) leukemia found in the blood and bone marrow, (2) lymphoma found in the lymphatic system, and (3) myeloma in many parts of bone marrow and also in the blood.

Leukemia has four broad classifications: (1) acute lymphocytic leukemia (ALL), (2) chronic lymphocytic leukemia (CLL), (3) acute myelogenous leukemia (AML), and (4) chronic myelogenous leukemia (CML). However, as advanced diagnostic and analytic methods are being developed, new types of leukemia, such as B cell CLL, T cell CLL, B cell prolymphocytic leukemia, Hairy cell leukemia, and others are been defined.

Lymphomas are divided into two categories: (1) Hodgkin lymphomas and (2) non-Hodgkin lymphomas. Of the patients who have lymphomas, about 12% have Hodgkin lymphomas and the rest have non-Hodgkin lymphomas. Of the non-Hodgkin lymphomas, most are B cell-derived and there are many subtypes of B cell non-Hodgkin lymphomas. The rest of the non-Hodgkin lymphomas are T cell lymphomas.

Myeloma is derived from antibody-producing plasma cells and is also referred to as plasmacytoma. Myeloma cells are found in bone marrow and can travel in the blood circulation and establish growth in many parts of the bone and hence myeloma is also called multiple myeloma.

While leukemia, lymphomas, and myeloma are derived from myeloid, lymphoid, and plasma cells, the diagnosis of the tumor types is often very complex, involving tissue and cellular examinations with histological, immunohistological, morphological, and cellular marker analyses of the biopsied tumor samples. Since the pluripotent stem cells, the myeloid lineage, which differentiate into granulocytes (neutrophils, eosinophils, and basophils), monocytes and macrophages, and platelets, and the lymphoid lineage, which differentiate into B cells and T cells, undergo many steps of differentiation and maturation, the malignant transformation can occur at any of the differentiation stages. Furthermore, the cancerous transformation may augment and gain certain traits and reduce or lose certain traits.

The surface markers or differentiation antigens, especially those, which have been assigned a CD (cluster of differentiation) number, have become very useful and often necessary to identify the various leukocytes and immunocytes in the studies of innate and adaptive immunity. Often the identification of a cell type requires a set of markers.

For antibody-based therapeutic approaches for targeting cancer of the leukocyte origin, identification of the surface markers of a targeted tumor is very useful and powerful. However, among the patients who have been diagnosed to have the same type of tumor, the surface markers can vary over a large range in terms of density.

I-(ii) Surface Markers on B Cell-Derived Lymphocytic Leukemia and Lymphoma

Both ALL and CLL are not solid tumors. ALL is derived from lymphoblasts, precursor B cells, precursor T cells, or B cells. ALL consists of the immunophenotypic subtypes: (1) precursor B cell acute lymphoblastic leukemia, which expresses cell surface markers associated with B cell precursors and precursor T cell acute lymphoblastic leukemia, which express markers of precursor T cells, (2) Burkitt's lymphoma, which is derived from B cells of the germinal center and express cell surface markers associated with B cells, and (3) acute biphenotypic leukemia, which express markers of both lymphoid and myeloid cells.

CLL is also referred to as B-cell CLL (B-CLL), because CLL is mostly derived from B cells. Thus, the major difference of the cellular origin between ALL and CLL is that ALL is derived from lymphoblasts, which are the common precursors of B cells and T cells and CLL is derived from B cells. All CLL cells in a patient are from monoclonal, derived original one B cell of a particular set of $V_H$ and $V_L$. The cells of CLL express CD19 and CD20, and characteristically CD5 and CD23.

Hodgkin lymphomas are characterized by the presence of Reed-Sternberg cells, which are multi-nucleated giant cells derived from B cells. There are at least four subtypes of Hodgkin lymphomas based on the morphology of Reed-Sternberg cells and the composition of reactive cell infiltrate in the lymph node biopsy specimen: (1) nodular sclerosing Hodgkin lymphoma, (2) mixed-cellularity, (3) lymphocyte-rich or lymphocytic predominance, and (4) lymphocyte depleted. It is well established that Hodgkin lymphoma is derived from mature B cells. Cells of Hodgkin lymphoma, depending on its immunophenotype, express a subset of CD15, CD20, CD30, CD79a, and CD138. Most of the cases of non-Hodgkin lymphomas are derived from B cells. There are at least 14 subtypes of B-cell non-Hodgkin lymphomas.

B lymphocytes are the source of antigen-specific antibodies and are a critical component of the adaptive immune system for the defense against infectious pathogens. However, B cells can also be pathogenic and the cause of several types of diseases. B-cell disorders are divided into undesired immunoglobulin production (autoimmune and allergic diseases) and uncontrolled proliferation (lymphomas, leukemia). B cells have proven to be effective targets for the treatment of multiple autoimmune disorders and B-lineage cancer. Many approaches pertaining to B-cell depletion for the treatment of B cell malignancies and antibody-mediated diseases have been developed with partial success or are in active experimental stages. These include therapeutic antibodies that target human B-cell surface antigens, such as CD19, CD20, CD22, CD37, CD79a/CD79b, and isotype-specific Ig receptor. Some of such antibodies can cause lysis of B cells. Some other antibodies will cause B cell lysis when the antibodies are conjugated with cytotoxic drugs.

Multiple myeloma, also referred to as plasma cell myeloma, is the second most common hematological malignancies (after non-Hodgkin lymphoma), constituting 1% of all cancers and 2% of all cancer deaths. Multiple myeloma produces large quantities of myeloma proteins and occupies bone marrow and manifests a series of symptoms, including bone pain, anemia, renal failure, infection, and neurological problems. Multiple myeloma is derived from the malignant transformation of plasma cells, which differentiate from B lymphocytes. However, cells of multiple myeloma do not express the most common B cell markers, such as CD19, CD20, and CD22.

A number of therapies and drugs have been experimented and a few have been approved for the treatment of multiple myeloma. These include corticosteroids, chemotherapies, proteasome inhibitors, and immunoregulatory compounds.

I-(iii) Unique B Cell Antigens Igα, Igβ and Migis-δ as Targets of Antibodies

Igα (CD79a)/Igβ (CD79b) is set of antigens that are expressed in association of the B cell receptor (BCR) complex on the surface of cells of the B-cell linage. Igα/Igβ is a heterodimeric transmembrane protein, which is composed of two distinct chains Igα and Igβ stabilized by disulfide bonding. Igα/Igβ forms a complex with the BCR and generates a signal following recognition of antigen by the BCR complex. During the development of B cell maturation, Igα/Igβ is expressed in the pre-B-cell stage and is early than CD20 for the expression pattern on the B-cell lineage. Igα/Igβ has been considered as attractive target for the B cell depletion therapy in the treatment of non-Hodgkin lymphomas because Igα/Igβ is expressed on B cells and on most non-Hodgkin lymphomas.

The mIgD and mIgM are coexpressed on the surface of mature B cells and function as part of BCR. The mIgD contains a unique migis-δ peptide segment of 27 AA, which represents the extracellular portions of the membrane-anchoring segment of mIgD and is located between the CH3 domain and transmembrane segment. It has been proposed that migis-δ peptide provides an antigenic site for targeting mIgD-expressing B cells. The site is present on the mIgD-expressing B cells and not on the secreted IgD.

I-(iv) T Cell Tumors

T lymphocyte subsets through their surface molecules and secreted factors mediate a complex network of immunoregulatory activities on humoral and cellular immune effector functions, including the production of different classes of antibodies, the secretion of various cytokines, and the generation of cytotoxic T cells and other cytolytic cells. Many autoimmune diseases are caused by the abnormal activities of T cells against self-components or cells. For example, in type-I diabetes, the insulin-producing β cells in the islets of Langerhans of pancreas are attacked and killed by autoimmune T cells. The devastating autoimmune diseases, such as systemic lupus erythematosus (SLE), multiple sclerosis, and inflammatory bowel diseases, are caused mainly by T cells. Furthermore, the rejection reaction toward organ or tissue transplants is mediated mainly by T cells.

There are also a few forms of T cell malignancy. Thus, modulating T cell activities or removing T cells has been an active area of drug discovery research. A variety of antibodies and their modified forms against T cell surface antigens, including CD3, CD4, CD8, CD25, and CD28 have been studied in animal models or human clinical trials for treating various human diseases mentioned above. Some antibodies with or without the conjugation with cytotoxic drugs can cause the lysis of the targeted T cell subsets. Some antibodies can cause anergy or an idled, inactive state of T cells without actually lysing the cells.

T lymphocytes play major roles in regulating activities of various immunocytes and various other cell types in adaptive and native immunity. In the development of therapeutic agents to target lymphocytes, fewer candidates have been successfully developed for targeting T cells than for targeting B cells. However, there have been increasing numbers of therapeutic antibodies that are being developed to target surface antigens of T cell subsets. Antibodies targeting T cell surface antigens can potentially be employed to treat malignant tumors derived from T cells. Antibodies may also be used to modulate T cell activities, either to inhibit them or to enhance them.

I-(v) Myelogenous Leukemia

AML is derived from myeloid stem cells or myeloid blasts, the precursors for the mature granulocytes and monocytes. Many of the subtypes of AML are caused by mutagens, which cause chromosomal translocations or loss of certain gene segments. Cells of AML derived from various differentiation stages express some subsets of surface markers of CD13, CD14, CD15, CD33, CD34, CD36, CD41, CD61, CD64, CD65, and CD11c. Cells of AML derived from the early precursor myeloid stages express CD34, which is a surface marker of pluripotent stem cells, and CD33, which is a marker of immature myeloid cells. Cells of AML derived from many myeloid differentiation stages express CD15, a marker of mature myeloid cells. CML is a clonal bone marrow stem cell disorder and resulted from the malignant transformation of a stem cell or myeloid stem cell, resulting from the chromosome translocation called the Philadelphia chromosome.

II Solid Tumor

II-(i) Solid Tumor and Tumor-Associated Antigens

Cells of many types of tumors express certain antigens on cell surface at elevated levels compared to those on normal cells. Those antigens are referred to as tumor-associated antigens. For example, serum samples from patients with pancreatic tumors and many types of gastrointestinal cancer, including colorectal cancer, esophageal cancer, and hepatocellular carcinoma, contain CA19-9 antigen (carbohydrate antigen 19-9, a sialyl-Lewis A antigen). The cells of those tumors express CA19-9 on the extracellular matrix on cell surface. Similarly, serum samples from patients with ovarian cancer, endometrial cancer, fallopian tube cancer, and some other types of cancer have elevated CA-125 (carbohydrate antigen 125, mucin 16) and the cells of those tumors express CA125. Overexpression of cell surface associated glycoprotein mucin 1 (MUC1) is often associated with colon, breast, ovarian, lung, and pancreatic cancer.

The ganglioside GD2 is highly expressed on neuroectoderm-derived tumors and sarcomas, including neuroblastoma, retinoblastoma, melanoma, small cell lung cancer, brain tumors, osteosarcoma, rhabdomyosarcoma, Ewing's sarcoma in children and adolescents, as well as liposarcoma, fibrosarcoma, leiomyosarcoma and other soft tissue sarcoma in adults.

While mesothelin is expressed on normal mesothelial cells, it is expressed on many human cancers, mesothelioma, tumors of the pancreas, ovary, lung, and stomach, cholangiocarcinoma, and triple-negative breast cancer.

Tn antigen is a structural element on glycoproteins, in which N-acetylgalactosamine (GalNAc) is linked to serine or threonine by a glycosidic bond, i.e. as an O-glycan. Addition of single monosaccharide residues creates disaccharide antigens: the Thomsen-Friedenreich antigen (TF antigen or T antigen) is formed by substitution with galactose (Gal(b1-3)GalNAc); the sialyl-Tn antigen (STn antigen) is formed by substitution with sialic acid (Neu5Ac(a2-6)GalNAc. TN and sialy-Tn are not usually found on healthy cell surfaces, but may be found on cancer cells.

Tumor-associated antigens that have been widely studied as markers of tumors or explored as targets for immunological therapies include (1) epidermal growth factor receptors (EGFRs)—human epidermal growth factor 1 (EGFR or HER1), HER2, HER3, HER4, or their mutants; (2) glycoproteins—CA19-9 (bearing Sialyl Lewis$^A$ antigen), CA125 (bearing mucin 16 or MUC 16), cell surface-associated mucin 1 (MUC1), or carcinoembryonic antigen, melanoma-associated antigen (MAGE), prostate-specific membrane antigen (PSMA), prostate stem cell antigen (PSCA), or mesothelin; (3) mucin-related Tn or Sialyl Tn; (4) the blood group Lewis related Lewis$^Y$, Sialyl Lewis$^Y$, Sialyl Lewis$^A$, or Lewis$^X$; (5) glycosphingolipids—Globo H or stage-specific embryonic antigen-4 (SSEA-4); or (6) gangliosides—GD2, GD3, GM2, fucosyl GM1, or Neu5GcGM3.

II-(ii) Growth Factors, Peptide Hormones, and Cytokines as Targeting Agents for Cells Overexpressing Receptors A number of growth factors, peptide hormones and regulatory cytokines regulate important physiological processes in a human body. These substances mediate their functions through interacting with their receptors on different cell types. The most prominent are endocrine or exocrine cells in organs or compartments or organs bearing function-specific receptors, which respond to growth factors, hormones, or cytokines. For example, the exocrine cells in the pancreas bear receptors that respond to secretin, gastrin, and cholecystokinin (CCK) from duodenum and stomach during food intake and digestive process.

When malignant transformation occurs to the receptor-bearing cells, the tumorous cells maintain the expression of the receptors. In fact, in many cases, an abnormally high expression of the receptors occurs due to certain mutations in the cells, which are not necessarily in the receptors themselves. The affected cells thus become malignantly transformed. The overexpression of receptors on tumors, e.g., somatostatin receptors are strongly expressed on most neuroendocrine tumors, and the targeting of those receptors for therapeutic and diagnostic (e.g., radio-imaging) purposes have been an active area of research. Neuroendocrine tumors are generally rare, but include a long list of tumors of various cell origins, including those of gastroenteropancreatic neuroendocrine tumors, thyroid gland tumors, Merkel cell carcinoma, adrenomedullary tumors, and many others.

Examples of this line of research are numerous. The over-expression of the family of epidermal growth factor receptors (EGFRs) in breast cancer, lung cancer, colon cancer, and many other types of carcinoma is well documented. For example, monoclonal antibody trastuzumab specific for HER2/Neu receptor is broadly used for treating HER2-positive breast cancer. Cetuximab specific for EGFR is being used in treating metastatic colon cancer, metastatic non-small cell lung cancer, and head and neck cancer. Small molecular inhibitors, such as gefitinib and erlotinib, which interrupts the tyrosine kinase domain in EGFR, have also been developed for the treatment of several type of cancer.

Pancreatic cancer is one of the most vicious cancers. Among the various types of pancreatic cancers, the pancreatic (ductal or invasive) adenocarcinoma derived from the exocrine cells account for 85%, although those ductal epithelial cells account only for 10% among all cells in the pancreas. The exocrine cells express receptors for the peptide hormones, gastrin, secretin, or cholecystokinin, which are secreted by the cells in the stomach and duodenum, and respond to those hormones and secrete bicarbonate ions and digestive enzymes. The overexpressed receptors for CCK and gastrin in pancreatic cancer and many other types have also been explored as a target for radioimaging. Other hormones and receptors, which are under active investigation, are somatostatin and gastrin-releasing peptide. In such radio-imaging approaches, CCK or gastrin of their peptide analogues are coupled with chelating groups for radioactive nuclides. In the imaging procedure, the imaging agents bind to the primary or metastasized tumors containing cells expressing the receptors. Peptide hormones or their analogues carrying radionuclides, lutetium-177, yttrium-90, or indium-111, have also been experimented for treating tumors.

II-(iii) Immune Checkpoints as Targets

CTLA-4 is a protein receptor that down-regulates the immune system. CTLA-4 is found on the surface of T cells, and acts as an "off" switch when bound to CD80 (B7-1) or CD86 (B7-2) on the surface of antigen presenting cells. Such binding prevents the binding of those receptors by CD28, which activates the immune response. A human IgG1 antibody specific for CTLA-4, ipilimumab, has been approved for treating melanoma and in clinical studies for treating several other types of cancer. The treatment with ipilimumab has been associated with severe and potential fatal immunological side effects due to T cell activation and proliferation.

PD-1 is expressed on the surface of activated T cells. If PD-1 is blocked by its ligand, PD-L1, the T cell becomes inactive. This is a way that the body regulates the immune system to avoid an overreaction of immune responses. Many cancer cells make PD-L1 and thereby disarm the T cells and inhibit them from attacking the cancer cells. Two human antibodies against PD-1, pembrolizumab and nivolumab, have been approved for treating unresectable or metastatic melanoma, which no longer respond to other drugs, and squamous non-small cell lung cancer. An anti-PD-L1 antibody, MPDL3280A, is now in Phase II or III clinical trials for triple-negative breast cancer, metastatic non-small cell lung cancer, bladder carcinoma, and renal cell carcinoma. A large number of anti-PD-1 and anti-PD-L1 antibodies are in research or early clinical trials.

Many researchers are exploring other targets, such as OX40, CD137, and CD27 on the activated T cells and their corresponding ligands, OX40L, CD137L, and CD137 the antigen-presenting cells or tumor cells for releasing the brakes of T cell activation. Those pathways are considered to be milder in T-cell activation strength than the CTLA-4 and PD-1 pathways.

While antibodies specific for PD-I or PD-L1 look very promising for treating several types of cancer, the current clinical development suggest that those antibodies will require the combination with chemotherapies, other antibodies, or targeted therapies. Also, the antibodies also cause a range of severe side effects. We rationalize that if the antibodies specific for immune checkpoints were carried to the targeted tumor site, better therapeutic efficacy could be achieved, and fewer side effects would occur.

II-(iv) Vascular Endothelial Growth Factor as Targets

Vascular endothelial growth factor A (VEGF-A) is essential for angiogenesis (blood vessel formation) as the tumor grows. The blood circulation is required for oxygen and nutrient supplies, waste disposal and many other functions. Antibodies specific for VEGF-A, such as bevacizumab specific for VEGF-A, are effective as a monotherapy or in combination with chemotherapy in treating a few forms of cancer. However, bevacizumab is associated with a range of side effects, including hypertension and heightened risk of bleeding, bowel perforation, and necrotizing fasciitis.

II-(v) Immunoregulatory Cytokines as Cancer Therapeutic Agents

The immunoregulatory cytokines referred to in this invention are those that are known to be stimulatory and are major drivers in activating immune responses. These cytokines include interleukin-2 (IL-2), interferon-α (IFN-α), interferon-γ (IFN-γ), and TNF-α. Among them, IFN-α, which is a strong activator of T cells, has been approved for use in hairy-cell leukemia, AIDS-related Kaposi's sarcoma, follicular lymphoma, chronic myeloid leukemia and melanoma. However, clinical studies so far have not established major therapeutic utilities of those immunoregulatory cytokines in treating tumors, mainly because the therapeutic doses of those cytokines in systematic administrations are limited by the side effects of the cytokines. In general, cytokines act mainly in the microenvironment of the lymphoid system.

PART I Molecular Constructs for Treating Tumors

In the broad sense of the Fc-based configuration, immunoglobulin antibody can serve as the base of a targeting or effector element, and its corresponding effector or targeting element can be incorporated at the C-terminal of its two heavy γ chains in the form of scFv domains. For a typical "Fc-based" configuration, two-chain IgG.Fc is used as the base of the molecular platform. Each of the polypeptide chain is fused with one or two targeting and one or two effector elements, for a total of two to three elements on each chain. The T-E molecule with an Fc-based configuration will have a total of four to six elements (e.g., scFv, growth factor, or cytokines). Optionally, the Fc portion of the molecular constructs also carries Fc-mediated effector functions, ADCC, and/or complement-mediated activation. While in certain other applications, such Fc-mediated effector functions are avoided.

A first aspect of the present disclosure is directed to an Fc-based molecular construct that has at least a pair of targeting elements and at least a pair of effector elements linked, directly or indirectly, to a CH2-CH3 domain of an immunoglobulin. By selecting the T-E elements of the present Fc-based molecular construct, the molecular construct can be used to treat various cellular proliferative diseases, including diffused tumor and solid tumors. The present disclosure is also advantageous in that, in some embodiments, it utilizes the linker unit according to embodiment of the present disclosure, which provides a facile means for controlling the amount of the cytotoxic drug payload of the present Fc-based molecular construct may take different configurations, which are discussed below, respectively.

I-(i) Molecular Constructs with Antibody as Targeting Elements and Drug Bundle as Effector Elements According to certain embodiments of the present disclosure, each effector element of the first pair of effector elements is a drug bundle, while each targeting element of the first pair of targeting elements is an antibody fragment specific for a cell surface antigen or a tumor associated antigen. In these cases, the Fc-based molecular constructs for treating tumors may have the configuration of molecular construct 1000A of FIG. 1A or molecular construct 1000B of FIG. 1B. As illustrated in FIG. 1A, the effector elements E1 (for example, drug bundles) are linked to the C-termini of the pair of CH2-CH3 segments 1010, whereas the targeting elements T1 (in this case, an scFv) are linked to the N-termini of the pair of CH2-CH3 segments 1010. According to alternative embodiments, the molecular construct 1000B (see, FIG. 1B) has a pair of targeting elements T1 that takes the form of a Fab 1030. Specifically, the Fab 1030 configuration comprises the $V_H$-CH1 domain 1020 and the $V_L$-CK domain 1025, and is linked to the N-termini of the pair of CH2-CH3 segments 1010, so that the Fc-based molecular construct 1000A adopts the IgG configuration. In this case, the pair of effector elements E1 is linked to the C-termini of the pair of CH2-CH3 chains 1010.

In some embodiments, the CH2-CH3 chains are adopted from human immunoglobulins γ1 or γ4. In general, γ1 is chosen, when Fc-mediated functions, such as antibody-dependent cellular cytotoxicity (ADCC) and complement-mediated activity (inflammatory activation or target cell lysis), are desired. In the case where Fc-mediated functions are avoided, γ4 is chosen for constructing the present Fc-based molecular constructs.

The drug bundle may be provided as a linker unit according to embodiments of the present disclosure (see, for example FIG. 4A to FIG. 4C below). Briefly, the drug bundle comprises a center core, a plurality of linking arms, and optionally, a coupling arm. The center core may be a compound having a plurality of amine groups or a polypeptide comprising a plurality of lysine (K) residues, according to various embodiments of the present disclosure. Each of the linking arms has one terminus that is linked to the center core by reacting with the amine groups of the compound core or the amine side chain of the K residues of the polypeptide core. The linking arm also carries a maleimide group at the free terminus thereof, wherein each of the molecules (e.g., molecules of cytotoxic drugs in this case, and/or TLR agonists, or chelator/radioactive nuclide complexes described below) is linked to the center core via connecting through the linking arm by reacting with the maleimide group. According to optional embodiments of the present disclosure, each of the effector elements E1 is a drug bundle with 3-5 cytotoxic molecules.

In the case where the center core is the polypeptide core, then the amino acid residue at the N- or C-terminus of the center core is a cysteine residue or has an azide group or an alkyne group. According to certain embodiments, for polypeptide cores with a terminal amino acid residue having the azide group, the drug bundle is linked to the peptide extension via the SPAAC reaction or CuAAC reaction occurred between said terminal residue and the C-terminus of the peptide extension. Alternatively, when the polypeptide cores has a terminal amino acid residue with the alkyne group, the drug bundle is linked to the peptide extension via the CuAAC reaction occurred between said terminal residue and the C-terminus of the peptide extension. Still alternatively, for polypeptide cores with a terminal residue that is cysteine or for compound cores, the drug bundle further comprises said coupling arm. Specifically, the coupling arm has one terminus linked to the center core by reacting with the cysteine residue of the polypeptide core or one amine group of the compound core. The coupling arm also carries an alkyne group, azide group, tetrazine group, or strained alkyne group at the free terminus thereof, so that the drug bundle is linked to the C-terminus of the peptide extension via the iEDDA reaction (for coupling arms with the tetrazine or cyclooctene group), SPAAC (for coupling arms with the azide or cyclooctyne group) reaction or CuAAC reaction (for coupling arms with the alkyne or azide group) occurred therebetween.

According to certain embodiments, the present Fc-based molecular construct for treating tumors further comprises a pair of peptide extensions 1050 (see, FIGS. 1A and 1B) respectively having the sequence of $(G_{2-4}S)_{2-8}C$ As illustrated, the pair of peptide extensions 1050 is linked to the C-termini of the pair of CH2-CH3 segments 1010. The cysteine residue at the C-terminus of the peptide extension is linked with a coupling arm 1055 via thiol-maleimide reaction occurred therebetween. Also, before being conjugated with the effector element E1 (in this case, a drug bundle), the free terminus of the conjugating arm (that is, the terminus that is not linked to the cysteine residue) is modified with an alkyne, azide, strained alkyne, or tetrazine group, so that the drug bundle is linked thereto via iEDDA reaction or the SPAAC or CUAAC reaction occurred therebetween.

For example, in FIG. 1A, the coupling arm 1040 of the effector element E1 (in this case, a drug bundle) is linked to the CH2-CH3 segment 1010 via iEDDA reaction. The ellipse 1045 as depicted in FIG. 1A represents the chemical bond resulted from the iEDDA reaction occurred between the peptide extension 1050 and the effector element E1. As could be appreciated, an iEDDA reaction is occurred between a tetrazine group and a cyclooctene group, such as a transcyclooctene (TCO) group.

Figure 1A:
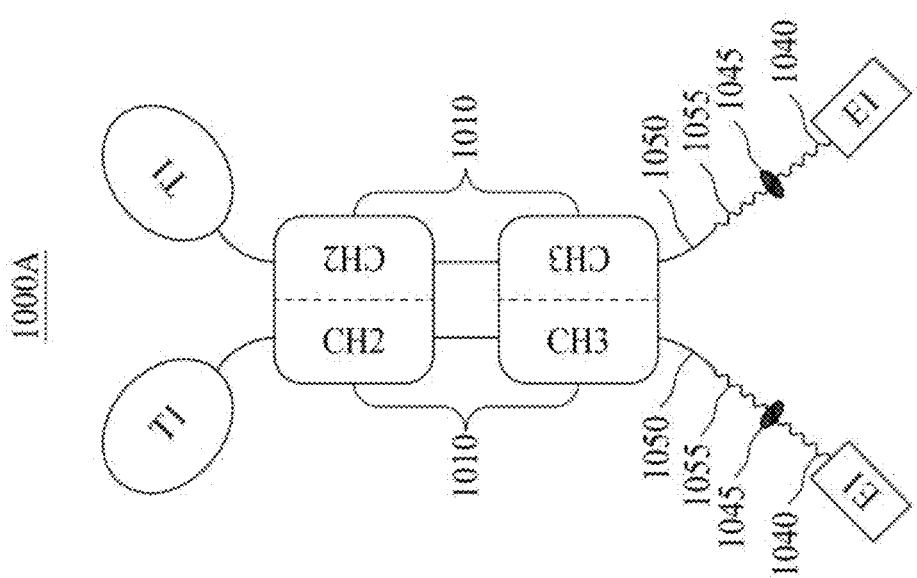

Alternatively, in FIG. 1B, the effector element E1 is linked to the CH2-CH3 segment 1010 via SPAAC reaction. The diamond 1045 as depicted in FIG. 1B represents the chemical bond resulted from the SPAAC reaction occurred between the peptide extension 1050 and the effector element E1. Specifically, an SPAAC reaction is occurred between an azide group and a strained alkyne group (e.g., a cyclooctyne group, including, dibenzocyclooctyne (DBCO), difluorinated cyclooctyne (DIFO), bicyclononyne (BCN), and dibenzocyclooctyne (DICO) group).

According to some optional embodiments of the present disclosure, the Fc-based molecular construct for treating tumors may further comprise a second pair of targeting elements. For example, the molecular construct 1000C of FIG. 1C comprises a first pair of targeting elements T1 and a second air of targeting elements T2, as well as effector elements E1. Specifically, the second pair of effector elements T2 is inked, in a tandem or diabody configuration, to the N-termini of the pair of elements T1 that is linked to the N-termini of the pair of CH2-CH3 segments 1010, thereby forming a pair of bispecific scFvs that is linked to the N-termini of the pair of CH2-CH3 segments 1010. Also, the pair of effector elements E1 is linked to the CH2-CH3 segment 1010 via iEDDA reaction by forming a chemical bond 1045 between the peptide extension 1050 and the effector element E1. However, the present disclosure is not limited thereto; rather, the effector elements E1 is linked to the CH2-CH3 segment 1010 via SPAAC reaction or CuAAC reaction in other embodiments.

Figure 1C:
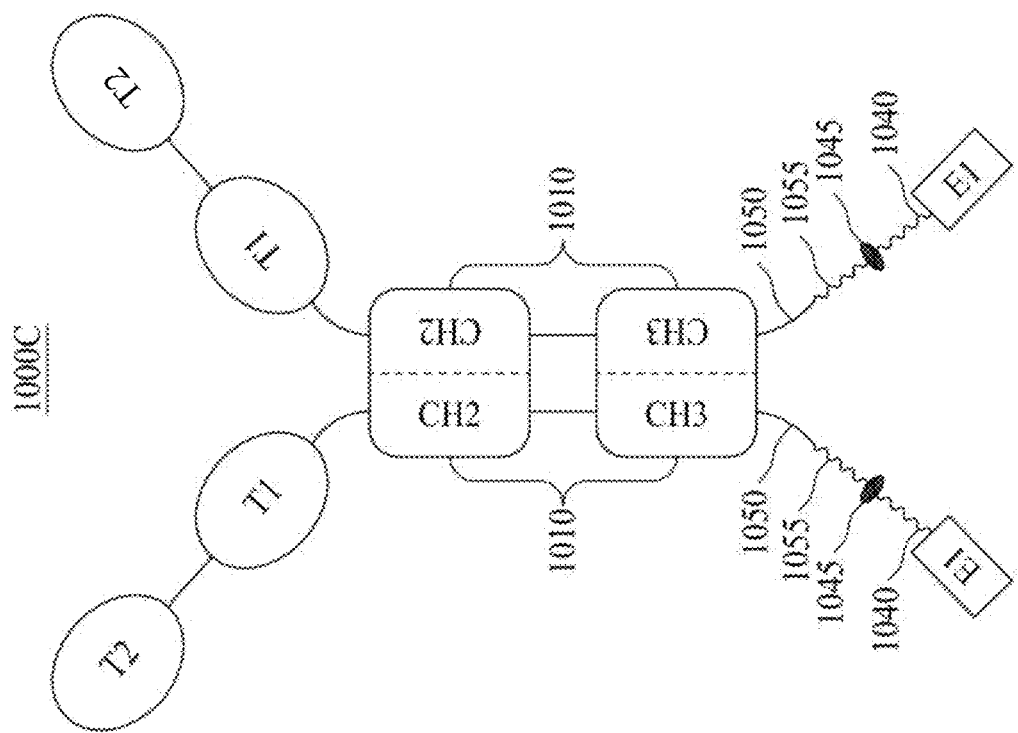

According to various embodiments of the present disclosure, the Fc-based molecular construct that has the configuration illustrated in any of FIG. 1A to FIG. 1C is applicable in the treatment of diffused tumors. For example, the drug bundle of such Fc-based molecular construct comprises a plurality of cytotoxic drug molecules, such as, auristatin, maytansine, doxorubicin, calicheamicin, and camptothecin. Also, the targeting elements of such Fc-based molecular construct may be an antibody fragment (e.g., scFv, Fab, or the like) specific for cell surface antigen selected from the group consisting of CD5, CD19, CD20, CD22, CD23, CD30, CD33, CD34, CD37, CD38, CD43, CD78, CD79a, CD79b, CD138, and CD319.

According to other embodiments of the present disclosure, the Fc-based molecular construct that has the configuration illustrated in any of FIG. 1A to FIG. 1C is applicable in the treatment of solid tumors, including malignant and/or metastatic solid tumors. In some cases, the drug bundle for use as effector elements comprises multiple cytotoxic drug molecules, e.g., auristatin, maytansine, doxorubicin, calicheamicin, and camptothecin. Alternatively, the drug bundle comprises multiple molecules of TLR agonist, such as, LPS, monophosphoryl lipid A, motolimod, imiquimod, resiquimod, gardiquimod, CpG DON, lipoteichoic acid, β-glucan, and zymosan. Still alternatively, the drug bundle comprises multiple molecules of a chelator (e.g., DOTA, NOTA, NODA, and DTPA) complexed with a radioactive nuclide (e.g., $^{90}Y$, $^{111}In$, and $^{177}Lu$). On the other hand, the targeting elements of such Fc-based molecular construct may be an antibody fragment (e.g., scFv, Fab, or the like) specific for HER1, HER2, HER3, HER4, CA19-9, CA125, CEA, MUC1, MAGE, PSMA, PSCA; mucin-related Tn, Sialyl Tn, Globo H, SSEA-4, ganglioside GD2, or EpCAM.

In the cases where the of Fc-based molecular constructs have a second pair of targeting elements, the effector element of the first pair of effector elements is a drug bundle comprising multiple cytotoxic drug molecules, while the first and second pairs of targeting elements are scFvs specific for HER2 and scFvs specific for HER1, respectively.

Figure 2:
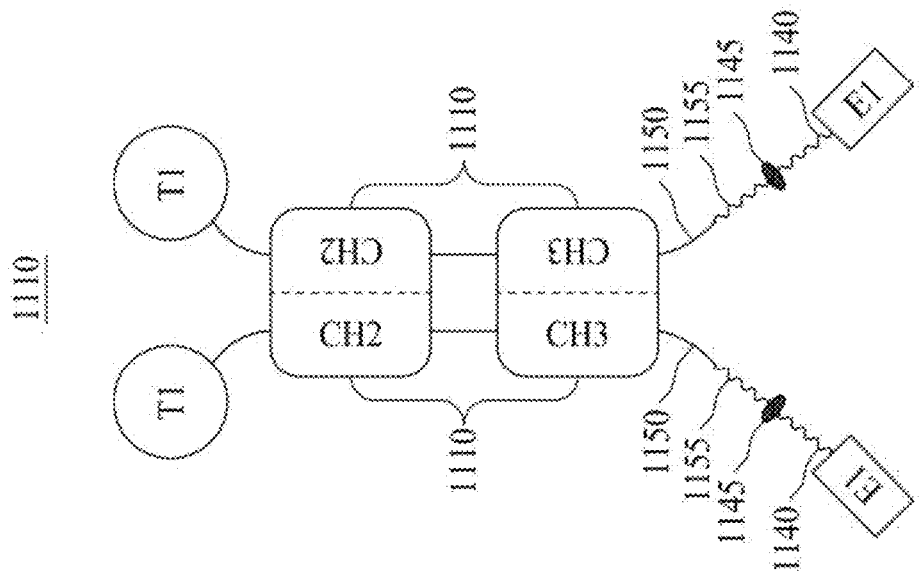
FIG. 2 is a schematic diagram illustrating Fc-based molecular constructs according to one embodiment of the present disclosure.

I-(ii) Molecular Constructs with Growth Factor/Peptide Hormone as Targeting Elements and Drug Bundle as Effector Elements According to certain embodiments of the present disclosure, each effector element of the first pair of effector elements is a drug bundle, while each targeting element of the first pair of targeting elements is a growth factor or a peptide hormone. In these cases, the Fc-based molecular constructs are suitable for treating solid tumors (including malignant and/or metastatic ones) may have the configuration of molecular construct 1100 of FIG. 2. As illustrated in FIG. 2, the effector elements E1 are linked to the C-termini of the pair of CH2-CH3 segments 1110, whereas the targeting elements T are linked to the N-termini of the pair of CH2-CH3 segments 1110.

Like the Fc-based molecular construct 1000A or 1000B, the present molecular construct 1100 further comprises a pair of peptide extensions 1150 respectively having the sequence of $(G_{2-4}S)_{2-8}C$, which is linked to the C-termini of the pair of CH2-CH3 segments 1110. Similarly, to facilitate the conjugation of the drug bundle, the cysteine residue is linked with a coupling arm 1155, and the drug bundle is linked to the coupling arm 1155 via iEDDA reaction, SPAAC reaction, or CuAAC reaction occurred therebetween (see the above discussion regarding FIG. 1A). For example, in FIG. 2, the coupling arm 1140 of the effector element E1 is linked to the coupling arm 1155 via iEDDA reaction, in which the ellipse 1145 represents the chemical bond resulted from the iEDDA reaction occurred between the coupling arm 1155 and the effector element E1. However, the present disclosure is not limited thereto; rather, the effector elements E1 is linked to the CH2-CH3 segment 1110 via SPAAC reaction or CuAAC reaction in other embodiments.

As could be appreciated, the discussions in Part I-(i) above regarding the Fc region and drug bundle of the Fc-based molecular constructs are also applicable here, and hence, detailed description regarding the same is omitted herein for the sake of brevity.

Since the present molecular construct (e.g., the molecular construct 1100) is applicable in the treatment of solid tumors, the drug bundle for use as effector elements comprises multiple cytotoxic drug molecules, e.g., auristatin, maytansine, doxorubicin, calicheamicin, and camptothecin, according to some embodiments. Alternatively, the drug bundle comprises multiple molecules of TLR agonist, such as, LPS, monophosphoryl lipid A, motolimod, imiquimod, resiquimod, gardiquimod, CpG DON, lipoteichoic acid, β-glucan, and zymosan. Still alternatively, the drug bundle comprises multiple molecules of a chelator (e.g., DOTA, NOTA, NODA, and DTPA) complexed with a radioactive nuclide (e.g., $^{90}$Y, $^{111}$In, and $^{177}$Lu).

On the other hand, targeting elements suitable for use in combination with the above-mentioned drug bundles are growth factors including, but not limited to EGF, mutant EGF, epiregulin, HB-EGF, VEGF-A, bFGF, and HGF. Other targeting elements combinable with the above-mentioned drug bundles are peptide hormones; illustrative examples of which include CCK, somastatin, and TSH.

I-(iii) Molecular Constructs with Growth Factor/Peptide Hormone as Targeting Elements and Antibody as Effector Elements According to other embodiments of the present disclosure, the Fc-based molecular construct comprises an antibody fragment as effector elements and a growth factor or peptide hormone as targeting elements. Such molecular constructs are applicable in the treatment of solid tumors (including malignant and/or metastatic ones).

Figure 3B:
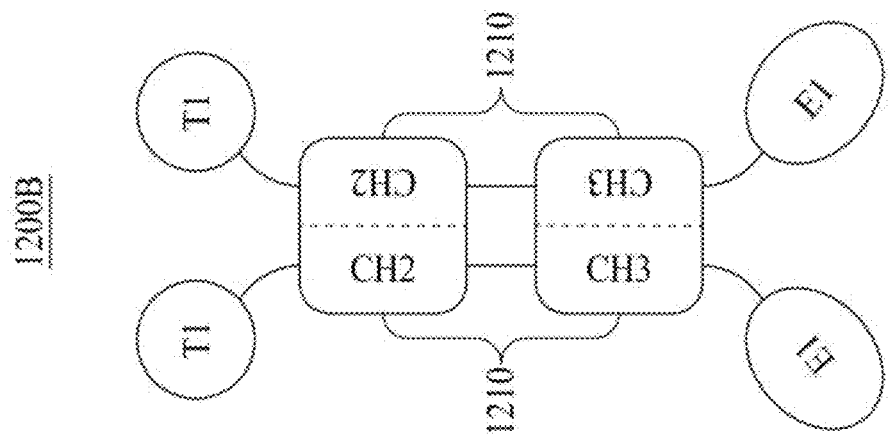
FIGS. 3A to 3C are schematic diagrams illustrating Fc-based molecular constructs according to various embodiments of the present disclosure.
Figure 3A:
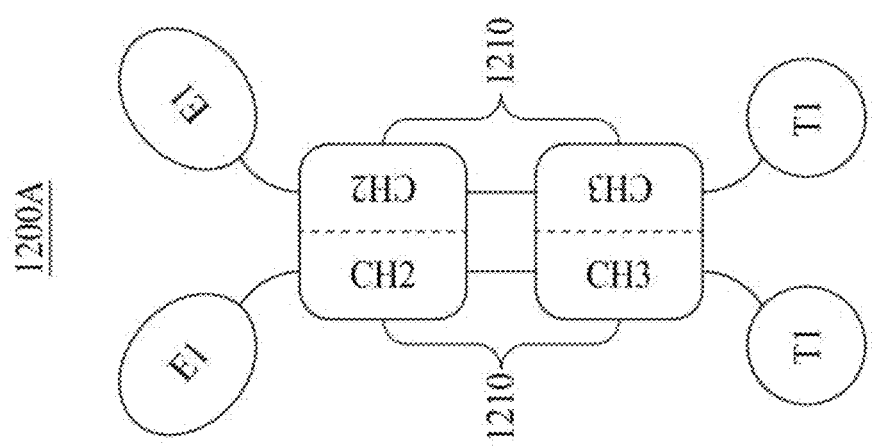

FIG. 3A illustrate a Fc-based molecular construct 1200A, in which the pair of effector elements E1 (in this case, scFvs) is linked to the N-termini of the pair of CH2-CH3 segments 1210, whereas the pair of targeting elements T1 is linked to the C-termini of the pair of CH2-CH3 segments 1210. As to the Fc-based molecular construct 1200B of FIG. 3B, the effector elements E1 and targeting elements T1 are respectively linked to the C- and N-termini of the pair of CH2-CH3 segments 1210.

Figure 3C:
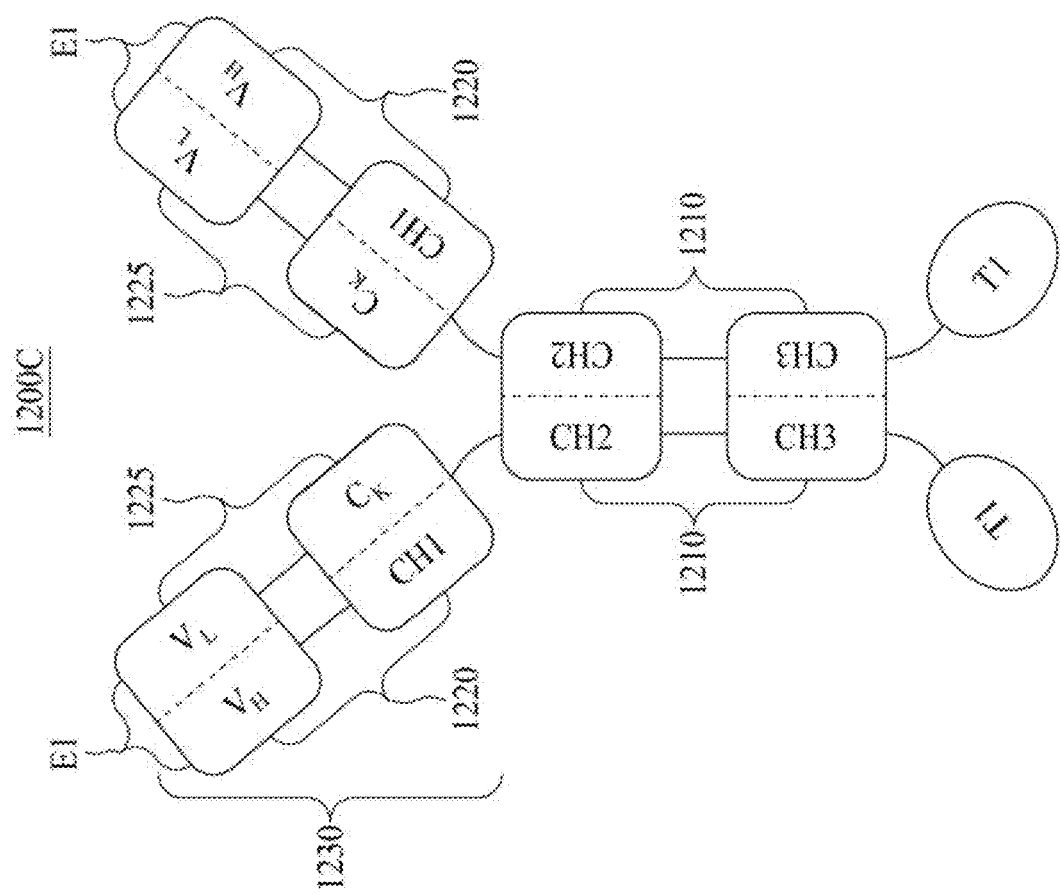

As could be appreciated, the antibody fragment may also take the form of a Fab, according to certain embodiments of the present disclosure. For example, the Fc-based molecular construct 1200C of FIG. 3C comprises a pair of effector elements E1 in the form of a Fab 1230. Specifically, the Fab 1230 configuration comprises the $V_H$-CH1 domain 1220 and the $V_L$-CK domain 1225; the Fab 1230 is linked to the N-termini of the pair of CH2-CH3 segments 1210 so that the Fc-based molecular construct 1200A adopts the IgG configuration. In this case, the pair of targeting elements T1 is linked to the C-termini of the pair of CH2-CH3 chains 1210.

According to various embodiments of the present disclosure, the antibody fragments suitable for use as the effector elements are those specific to cell surface antigens such as PD-1, PD-L1, CTLA-4, CD3, CD16a, CD28, and CD134. Another example of the effector element is the antibody fragment specific for the growth factor like EGF, mutant EGF, epiregulin, HB-EGF, VEGF-A, bFGF, and HGF. Antibody fragments specific for haptens are also suitable for use as effector elements, and illustrative examples of haptens include DNP, TNP, dansyl, penicillin, p-aminobenzoic acid, and a polypeptide having the amino acid sequence of SEQ ID NO: 20.

As to the targeting element suitable for use in this series of Fc-based molecular constructs, the targeting element may be a growth factor such as EGF, mutant EGF, epiregulin, HB-EGF, VEGF-A, bFGF, and HGF. Alternatively, the targeting element may be a peptide hormone like CCK, somastatin, and TSH.

The essence of this invention is the rationalization and conception of the specific combination or pairing of the targeting and effector elements. The adoption of Fc-fusion configuration in the molecular constructs is a preferred embodiment. It is conceivable for those skilled in the arts to link the pairs of targeting and effector elements of this invention employing other molecular platforms, such as peptides, proteins (e.g., albumin), polysaccharides, polyethylene glycol, and other types of polymers, which serve as a structural base for attaching multiple molecular elements.

PART II Uses of Molecular Constructs for Treating Tumors

By selecting the effector element(s) and the targeting element(s), the Fc-based molecular constructs of Part I above are also useful in the treatment of various tumors, including diffused tumors and solid tumors. In view of this, the present disclosure also covers method for treating tumors by using the Fc-based molecular construct in Part I. According to embodiments of the present disclosure, the method comprises the administration of the present Fc-based molecular construct or a pharmaceutical comprising the same in an effective amount to a subject in need of such treatment.

For a molecular construct targeting tumor cells, such as those targeting EGFR, HER2/neu, or CD20, the pharmacologic purpose is to lyse the targeted cells expressing those antigens. In general, it is desirable that the molecular construct bear Fc-mediated functions, such as ADCC or complement-mediated cytolysis. However, if the molecular construct can be joined with effector elements that elicit strong immune-destruction functions, such as scFv specific for CD3 or CD16a, or immunoregulatory functions, such as scFv specific for PD-1, PD-L1, CTLA-4, the Fc-mediated functions may not be crucial. The IgG molecules may also be linked at the termini of the two heavy chains with bundles of cytotoxic molecules, LPS molecules, or chelating groups for radioactive nuclides.

Fc region (paired CH2-CH3 domains) of human IgG1 mediates antibody-dependent cellular cytotoxicity (ADCC) and complement-mediated cytolysis (CMC). The present invention rationalizes that those Fc-mediated functions can be maintained, while increasing the binding avidity of an antibody's binding ability. It is known that some proportions of cells in tumor, which express low densities of targeted antigens, are resistant to the targeting therapeutic antibodies. For example, cells expressing low levels of HER2/Neu in breast tumor or CD20 in B cell lymphoma are not killed by trastuzumab or rituximab, respectively. The molecular conjugates of this invention with much higher binding avidity may bind sufficiently strongly to those cells and mediate cytolytic mechanism on them.

Different Fc receptors for different subclasses of IgG are on different sets of effector cells, which mediate different sets of immune mechanisms in conjunction with the IgG subclasses. FcγRI (CD64), FcγRIIa (CD32), and FcγRIIIb (CD16b) are on macrophages, neutrophils, and eosinophils, and mediate phagocytosis of IgG-coated particles and microbes. FcγRIIIa (CD16a) is mainly on NK cells and macrophages in some tissues and mediates ADCC. When FcγRIIIa on NK cells are bound by IgG1 and clustered, the NK cells secrete cytotoxic granules and death-causing factors that lyse the IgG-bound cells. A preferred embodiment of this invention is to conjugate scFv of antibodies specific for FcγRIIIa to multi-arm linkers, which are conjugated with scFv for various antigenic targets (e.g., CD20, EGFR) and tumor-associated antigens expressed on various cell targets. It is shown in a recent paper that a bi-specific antibody with one Fab specific for HER2/Neu and one Fab specific for FcγRIIIa is superior to anti-HER2/Neu antibody trastuzumab in lysing tumor cells expressing low density of HER2 antigen. The molecular construct of this invention has higher avidity for both HER2/Neu and should have higher lytic activities toward tumor cells expressing very low HER2/Neu.

To treat diffused tumors, such as B lymphocyte-derived lymphoma or leukemia, plasmacytoma, multiple myeloma, T-cell derived lymphoma or leukemia, and myelogenous leukemia, the present Fc-based molecular construct uses drug bundles comprising multiple cytotoxic drug molecules as effector elements, and antibody fragments specific for a suitable cell surface antigen as targeting elements.

According to certain embodiments, the present method is used to treat B lymphocyte-derived lymphoma or leukemia. In these cases, the cell surface antigens targeted by the present Fc-based molecular construct are cell surface antigens on human B lymphocytes, such as CD5, CD19, CD20, CD22, CD23, CD30, CD37 CD43, CD79a, and CD79b.

In other embodiments, the diffused tumor treatable by the present method is plasmacytoma or multiple myeloma, and the cell surface antigens targeted in these cases are those on human plasma cells, including CD38, CD78, CD138, and CD319.

Alternatively, the present method involves the treatment of T-cell derived lymphoma or leukemia using molecular constructs that target cell surface antigens on human T cells, such as CD5, CD30, and CD43.

When treating myelogenous leukemia according to some embodiments, the cell surface antigens targeted by the molecular construct used are those on human myeloid lineage leukocytes, like CD33 and CD34.

According to certain embodiments, the present Fc-based molecular construct uses drug bundles as effector elements and antibody fragments specific for a suitable tumor-associated antigen as targeting elements to treat solid tumors, such as melanomas, esophageal carcinomas, gastric carcinomas, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, and head and neck squamous cell carcinoma. In particular, the molecular constructs discussed above in Part III below are preferred in these embodiments.

According to some optional embodiments, the method for treating solid tumors further comprises the step of subjecting the subject to a blood dialysis procedure using an antibody fragment specific for one or more tumor-associated antigens to remove the tumor-associated antigens that are shed from the tumor into the circulation of the subject, prior to the administration of the molecular construct.

Alternatively, the method for treating solid tumors involves the use of Fc-based molecular construct with drug bundles or antibody fragments specific for cell surface antigens, growth factors or haptens as effector elements, and growth factors or peptide hormones as targeting elements. Illustrative examples of such molecular construct include those discussed above in Part I-(iii). The solid tumor treatable by these molecular constructs are melanomas, esophageal carcinomas, gastric carcinomas, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, or head and neck squamous cell carcinoma.

According to some embodiments, the molecular construct uses drug bundles of cytotoxic drug molecules as effector elements and EGF or its mutants as targeting elements.

According to other embodiments, the molecular construct uses scFvs specific for CD3, CD16a, PD-1, or VEGF as effector elements and EGF or its mutants as targeting elements.

According to some embodiments, the effector elements are antibody fragments specific for hapten. In these cases, the method further comprises the step of administering to the subject an immunoregulatory effector that is tagged with the same hapten after the administration of the molecule construct. For example, the immunoregulatory effector can be IFN-α, IL-2, TNF-α, and IFN-γ, and an IgG antibody specific for PD-1, PD-L1, CTLA-4, or CD3.

In some embodiments, the pair of CH2-CH3 segments is derived from human IgG heavy chain γ1, and the molecular construct uses drug bundles of cytotoxic drug molecules or LPS molecules as effector elements and EGF or its mutants, epiregulin, HB-EGF, VEGF-A, FGF, HGF, CCK, somastatin, or TSH as targeting elements.

In some embodiments, the pair of CH2-CH3 segments is derived from human IgG heavy chain γ1, and the molecular construct uses scFvs specific for human CD3, CD16a, PD-1, PD-L1, or VEGF-A as effector elements and EGF or its mutants, epiregulin, HB-EGF, VEGF-A, FGF, HGF, CCK, somastatin, or TSH as targeting elements.

PART III Drug Bundles Based on Multi-Arm Linkers

Embodiments of the present disclosure also pertains to linker units carrying a plurality of drug molecules; to facilitate the understanding of the present disclosure, such linker units are sometimes referred to as a "drug bundle" in the present disclosure. To form a T-E construct for use in the treatment of tumors, such drug bundle (as the effector element) can be conjugated with the Fc-based molecular construct (as the targeting element) discussed in Part I above.

According to some embodiments, the linker unit is a multi-arm linker comprising, (1) a center core that comprises 2-15 lysine (K) residues, and (2) 2-15 linking arms respectively linked to the K residues of the center core. The present center core is characterized in having or being linked with an azide group, an alkyne group, a tetrazine group, or a strained alkyne group at its N- or C-terminus.

In the preparation of the present linker unit, a PEG chain having a N-hydroxysuccinimydyl (NHS) group at one terminus and a maleimide group at the other terminus is linked to the K residue of the center core by forming an amide bond between the NHS group of the PEG chain and the amine group of the K residue. In the present disclosure, the PEG chain linked to the K residue is referred to as a linking arm, which has a maleimide group at the free-terminus thereof.

According to the embodiments of the present disclosure, the center core is a polypeptide that has 8-120 amino acid residues in length and comprises 2 to 15 lysine (K) residues, in which each K residue and the next K residue are separated by a filler sequence.

According to embodiments of the present disclosure, the filler sequence comprises glycine (G) and serine (S) residues; preferably, the filler sequence consists of 2-15 residues selected from G, S, and a combination thereof. For example, the filler sequence can be,

GS,

GGS,

GSG,

GGGS, (SEQ ID NO: 1)

GSGS, (SEQ ID NO: 2)

GGSG, (SEQ ID NO: 3)

GSGGS, (SEQ ID NO: 4)

SGGSG, (SEQ ID NO: 5)

GGGGS, (SEQ ID NO: 6)

GGSGS, (SEQ ID NO: 7)

GGSGGSG, (SEQ ID NO: 8)

SGSGGSGS, (SEQ ID NO: 9)

GSGGSGSGS, (SEQ ID NO: 10)

SGGSGGSGSG, (SEQ ID NO: 11)

GGSGGSGGSGS, (SEQ ID NO: 12)

SGGSGGSGSGGS, (SEQ ID NO: 13)

GGGGSGGSGGGGS, (SEQ ID NO: 14)

GGGSGSGSGSGGGS, or (SEQ ID NO: 15)

SGSGGGGSGGSGSG. (SEQ ID NO: 16)

The filler sequence placed between two lysine residues may be variations of glycine and serine residues in somewhat random sequences and/or lengths. Longer fillers may be used for a polypeptide with fewer lysine residues, and shorter fillers for a polypeptide with more lysine residues. Hydrophilic amino acid residues, such as aspartic acid and histidine, may be inserted into the filler sequences together with glycine and serine. As alternatives for filler sequences made up with glycine and serine residues, filler sequences may also be adopted from flexible, soluble loops in common human serum proteins, such as albumin and immunoglobulins.

According to certain preferred embodiments of the present disclosure, the center core comprises 2-15 units of the sequence of $G_{1-5}SK$. Alternatively, the polypeptide comprises the sequence of $(GSK)_{2-15}$; that is, the polypeptide comprises at least two consecutive units of the sequence of GSK. For example, the present center core may comprises the amino acid sequence of the following, Ac-CGGSGGSGGSKGSGSK, (SEQ ID NO: 17)

Ac-CGGSGGSGGSKGSGSKGSK, (SEQ ID NO: 18)

or

Ac-CGSKGSKGSKGSKGSKGSKGSKGSKGSK, (SEQ ID NO: 19)

in which Ac represents the acetyl group.

According to certain embodiments of the present disclosure, the center core is a polypeptide that comprises the sequence of $(X_{aa}\text{-}K)_n$, in which $X_{aa}$ is a PEGylated amino acid having 2 to 12 repeats of ethylene glycol (EG) unit, and n is an integral from 2 to 15.

As described above, the present center core is characterized in having or being linked with an azide group, an alkyne group, a tetrazine group, or a strained alkyne group at its N- or C-terminus. According to some embodiments of the present disclosure, the present center core comprises, at its N- or C-terminus, an amino acid residue having an azide group or an alkyne group. The amino acid residue having an azide group can be, L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine. For example, the present center core may have the sequence of, Ac-(GSK)$_{2-7}$-(G$_{2-4}$S)$_{1-8}$-A$^{AH}$,
Ac-A$^{AH}$-(SG$_{2-4}$)$_{1-8}$-(GSK)$_{2-7}$,
Ac-A$^{AH}$-(SG$_{2-4}$)$_{0-7}$-(GSK)$_{2-6}$-(G$_{2-4}$S)$_{1-8}$-C,
Ac-C-(SG$_{2-4}$)$_{0-7}$-(GSK)$_{2-6}$-(G$_{2-4}$S)$_{1-8}$-A$^{AH}$,
Ac-K-(Xaa$_{2-12}$-K)$_{2-4}$-Xaa$_{2-12}$-A$^{AH}$,
Ac-A$^{AH}$-Xaa$_{2-12}$-K-(Xaa$_{2-12}$-K)$_{2-4}$,
Ac-A$^{AH}$-Xaa$_{2-12}$-K-(Xaa$_{2-12}$-K)$_{1-3}$-Xaa$_{2-12}$-C, or
Ac-C-Xaa$_{2-12}$-K-(Xaa$_{2-12}$-K)$_{1-3}$-Xaa$_{2-12}$-A$^{AH}$, in which Xaa is a PEGylated amino acid having specified repeats of EG unit, Ac represents the acetyl group, and A$^{AH}$ represents the AHA residue.

Exemplary amino acid having an alkyne group includes, but is not limited to, L-homopropargylglycine (L-HPG), D-homopropargylglycine (D-HPG), or beta-homopropargylglycine (β-HPG). In this case, the present center core may have the sequence of, Ac-(GSK)$_{2-7}$-(G$_{2-4}$S)$_{1-8}$-G$^{HP}$,
Ac-G$^{HP}$-(SG$_{2-4}$)$_{1-8}$-(GSK)$_{2-7}$,
Ac-G$^{HP}$-(SG$_{2-4}$)$_{0-7}$-(GSK)$_{2-6}$-(G$_{2-4}$S)$_{1-8}$-C,
Ac-C-(SG$_{2-4}$)$_{0-7}$-(GSK)$_{2-6}$-(G$_{2-4}$S)$_{1-8}$-G$^{HP}$,
Ac-K-(Xaa$_{2-12}$-K)$_{2-4}$-Xaa$_{2-12}$-G$^{HP}$,
Ac-G$^{HP}$-Xaa$_{2-12}$-K-(Xaa$_{2-12}$-K)$_{2-4}$,
Ac-G$^{HP}$-Xaa$_{2-12}$-K-(Xaa$_{2-12}$-K)$_{1-3}$-Xaa$_{2-12}$-C, or
Ac-C-Xaa$_{2-12}$-K-(Xaa$_{2-12}$-K)$_{1-3}$-Xaa$_{2-12}$-G$^{HP}$, in which Xaa is a PEGylated amino acid having specified repeats of EG unit, Ac represents the acetyl group, and G$^{HP}$ represents the HPG residue.

It is noted that many of the amino acids containing an azide or alkyne group in their side chains and PEGylated amino acids are available commercially in t-boc (tert-butyloycarbonyl)- or Fmoc (9-fluorenylmethyloxycarbonyl)-protected forms, which are readily applicable in solid-phase peptide synthesis.

According to some working examples of the present disclosure, the center core may comprise the sequence of, Ac-G$^{HP}$GGSGGSGGSKGSGSK, (SEQ ID NO: 21)

Ac-G$^{HP}$GGSGGSGGSKGSGSKGSK, (SEQ ID NO: 22)

Ac-A$^{AH}$GGSGGSGGSKGSGSKGSK, (SEQ ID NO: 23)

Ac-G$^{HP}$GGSGGSGGSKGSGSKGSGSC, (SEQ ID NO: 24)

Ac-C-Xaa$_2$-K-Xaa$_2$-K-Xaa$_2$-K, (SEQ ID NO: 25)
or

Ac-C-Xaa$_6$-K-Xaa$_6$-K-Xaa$_6$-K-Xaa$_6$-K-Xaa$_6$-K, (SEQ ID NO: 26)

in which Xaa is a PEGylated amino acid having specified repeats of EG unit, Ac represents the acetyl group, A$^{AH}$ represents the AHA residue, and G$^{HP}$ represents the HPG residue.

Alternatively, the present center core is linked with a coupling arm, which has a functional group (e.g., an azide group, an alkyne group, a tetrazine group, or a strained alkyne group) at the free-terminus thereof (that is, the terminus that is not linked to the center core). In these cases, the present center core comprises a cysteine residue at its N- or C-terminus. To prepare a linker unit linked with a coupling arm, a PEG chain having a maleimide group at one terminus and a functional group at the other terminus is linked to the cysteine residue of the center core via thiol-maleimide reaction occurred between the maleimide group of the PEG chain and the thiol group of the cysteine residue. In the present disclosure, the PEG chain linked to the cysteine residue of the center core is referred to as the coupling arm, which has a functional group at the free-terminus thereof.

Preferably, the coupling arm has a tetrazine group or a strained alkyne group at the free-terminus thereof. These coupling arms have 2-12 EG units. According to the embodiments of the present disclosure, the tetrazine group is 1,2,3,4-tetrazine, 1,2,3,5-tetrazine, 1,2,4,5-tetrazine, or derivatives thereof. Example of strained alkyne group includes, but is not limited to, trans-cyclooctene (TCO), dibenzocyclooctyne (DBCO), difluorinated cyclooctyne (DIFO), bicyclononyne (BCN), dibenzocyclooctyne (DICO). According to some embodiments of the present disclosure, the tetrazine group is 6-methyl-tetrazine.

Example of the present center core linked with the coupling arm includes, but is not limited to, Ac-(GSK)$_{2-7}$-(G$_{2-4}$S)$_{1-8}$-C-Xaa$_{2-12}$-tetrazine,
Ac-(GSK)$_{2-7}$-(G$_{2-4}$S)$_{1-8}$-C-Xaa$_{2-12}$-strained alkyne,
Ac-K-(Xaa$_{2-12}$-K)$_{2-4}$-Xaa$_{2-12}$-C-Xaa$_{2-12}$-tetrazine,
Ac-K-(Xaa$_{2-12}$-K)$_{2-4}$-Xaa$_{2-12}$-C-Xaa$_{2-12}$-strained alkyne,
Tetrazine-Xaa$_{2-12}$-C(Ac)-(SG$_{2-4}$)$_{1-8}$-(GSK)$_{2-7}$,
Stained alkyne-Xaa$_{2-12}$-C(Ac)-(SG$_{2-4}$)$_{1-8}$-(GSK)$_{2-7}$,
Tetrazine-Xaa$_{2-12}$-C(Ac)-Xaa$_{2-12}$-K-(Xaa$_{2-12}$-K)$_{2-4}$, and
Strained alkyne-Xaa$_{2-12}$-C(Ac)-Xaa$_{2-12}$-K-(Xaa$_{2-12}$-K)$_{2-4}$.

Alternatively, the center core has an azide or alkyne group at one terminus and a coupling arm with tetrazine or strained alkyne group at the other terminus. Examples are the following:

Ac-A$^{AH}$-(SG$_{2-4}$)$_{0-7}$-(GSK)$_{2-6}$-(G$_{2-4}$S)$_{1-8}$-C-Xaa$_{2-12}$-tetrazine,
Ac-A$^{AH}$-(SG$_{2-4}$)$_{0-7}$-(GSK)$_{2-6}$-(G$_{2-4}$S)$_{1-8}$-C-Xaa$_{2-12}$-strained alkyne,
Tetrazine-Xaa$_{2-12}$-C(Ac)-(SG$_{2-4}$)$_{0-7}$-(GSK)$_{2-6}$-(G$_{2-4}$S)$_{1-8}$-A$^{AH}$,
Strained alkyne-Xaa$_{2-12}$-C(Ac)-(SG$_{2-4}$)$_{0-7}$-(GSK)$_{2-6}$-(G$_{2-4}$S)$_{1-8}$-A$^{AH}$,
Ac-A$^{AH}$-Xaa$_{2-12}$-K-(Xaa$_{2-12}$-K)$_{1-3}$-Xaa$_{2-12}$-C-Xaa$_{2-12}$-tetrazine,
Ac-A$^{AH}$-Xaa$_{2-12}$-K-(Xaa$_{2-12}$-K)$_{1-3}$-Xaa$_{2-12}$-C-Xaa$_{2-12}$-strained alkyne,
Tetrazine-Xaa$_{2-12}$-C(Ac)-Xaa$_{2-12}$-K-(Xaa$_{2-12}$-K)$_{1-3}$-Xaa$_{2-12}$-A$^{AH}$,
Strained alkyne-Xaa$_{2-12}$-C(Ac)-Xaa$_{2-12}$-K-(Xaa$_{2-12}$-K)$_{1-3}$-Xaa$_{2-12}$-A$^{AH}$,
Ac-G$^{HP}$-(SG$_{2-4}$)$_{0-7}$-(GSK)$_{2-6}$-(G$_{2-4}$S)$_{1-8}$-C-Xaa$_{2-12}$-tetrazine,
Ac-G$^{HP}$-(SG$_{2-4}$)$_{0-7}$-(GSK)$_{2-6}$-(G$_{2-4}$S)$_{1-8}$-C-Xaa$_{2-12}$-strained alkyne,
Tetrazine-Xaa$_{2-12}$-C(Ac)-(SG$_{2-4}$)$_{0-7}$-(GSK)$_{2-6}$-(G$_{2-4}$S)$_{1-8}$-G$^{HP}$,
Strained alkyne-Xaa$_{2-12}$-C(AC)-(SG$_{2-4}$)$_{0-7}$-(GSK)$_{2-6}$-(G$_{2-4}$S)$_{1-8}$-G$^{HP}$,
Ac-G$^{HP}$-Xaa$_{2-12}$-K-(Xaa$_{2-12}$-K)$_{1-3}$-Xaa$_{2-12}$-C-Xaa$_{2-12}$-tetrazine,
Ac-G$^{HP}$-Xaa$_{2-12}$-K-(Xaa$_{2-12}$-K)$_{1-3}$-Xaa$_{2-12}$-C-Xaa$_{2-12}$-strained alkyne,
Tetrazine-Xaa$_{2-12}$-C(Ac)-Xaa$_{2-12}$-K-(Xaa$_{2-12}$-K)$_{1-3}$-Xaa$_{2-12}$-G$^{HP}$, and
Strained alkyne-Xaa$_{2-12}$-C(Ac)-Xaa$_{2-12}$-K-(Xaa$_{2-12}$-K)$_{1-3}$-Xaa$_{2-12}$-G$^{HP}$.

The polypeptide may also be synthesized using recombinant technology by expressing designed gene segments in bacterial or mammalian host cells. It is preferable to prepare the polypeptide as recombinant proteins if the core has high numbers of lysine residues with considerable lengths. As the length of a polypeptide increases, the number of errors increases, while the purity and/or the yield of the product decrease, if solid-phase synthesis was adopted. To produce a polypeptide in bacterial or mammalian host cells, a filler sequence ranges from a few amino acid residues to 10-20 residues may be placed between two K residues. Further, since AHA and HPG are not natural amino acids encoded by the genetic codes, the N-terminal or C-terminal residue for those recombinant polypeptides is cysteine. After the recombinant proteins are expressed and purified, the terminal cysteine residue is then reacted with short bifunctional cross-linkers, which have maleimide group at one end, which reacts with SH group of cysteine residue, and alkyne, azide, tetrazine, or strained alkyne at the other end.

The synthesis of a polypeptide using PEGylated amino acids involves fewer steps than that with regular amino acids such as glycine and serine resides. In addition, PEGylated amino acids with varying lengths (i.e., numbers of repeated ethylene glycol units) may be employed, offering flexibility for solubility and spacing between adjacent amino groups of lysine residues. Other than PEGylated amino acids, the center cores may also be constructed to comprise artificial amino acids, such as D-form amino acids, homo-amino acids, N-methyl amino acids etc. Preferably, the PEGylated amino acids with varying lengths of polyethylene glycol (PEG) are used to construct the center core, because the PEG moieties contained in the amino acid molecules provide conformational flexibility and adequate spacing between conjugating groups, enhance aqueous solubility, and are generally weakly immunogenic. The synthesis of PEGylated amino acid-containing center core is similar to the procedures for the synthesis of regular polypeptides.

Optionally, for stability purpose, the present center has an acetyl group to block the amino group at its N-terminus.

As could be appreciated, the number of the linking arms linked to the center core is mainly determined by the number of lysine resides comprised in the center core. Since there are at least two lysine residues comprised in the present center core, the present linker unit may comprise a plurality of linking arms.

Figure 4A:
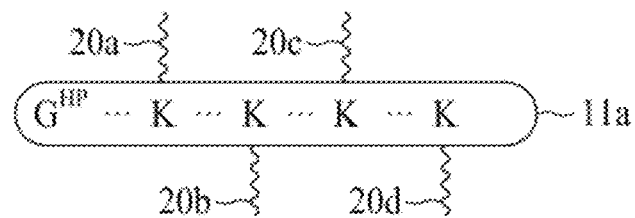
FIGS. 4A to 4K are schematic diagrams illustrating linker units according to certain embodiments of the present disclosure.

Reference is now made to FIG. 4A. As illustrated, the linker unit 10A comprises a center core 11a comprising one HPG ($G^{HP}$) residue and four lysine (K) residues respectively separated by filler sequences (denoted by the dots throughout the drawings). The filler sequences between the HPG residue and K residue or between any two K residues may comprise the same or different amino acid sequences. In this example, four linking arms 20a-20d are linked to the lysine residues by forming an amide linkage between the NHS group and the amine group of the lysine reside, respectively. As could be appreciated, certain features discussed above regarding the linker unit 10A or any other following linker units are common to other linker units disclosed herein, and hence some or all of these features are also applicable in the following examples, unless it is contradictory to the context of a specific embodiment. However, for the sake of brevity, these common features may not be explicitly repeated below.

Figure 4B:
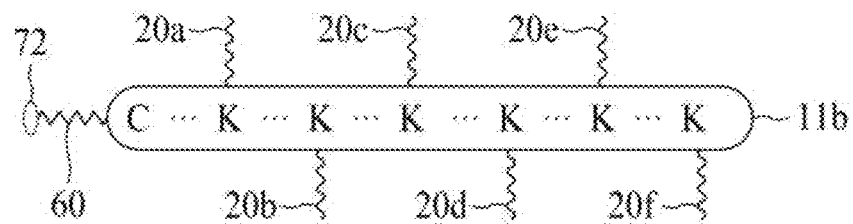

FIG. 4B provides a linker unit 10B according to another embodiment of the present disclosure. The center core 11b comprises one cysteine (C) residue and six lysine (K) residues respectively separated by the filler sequences. In this example, the linker unit 10A comprises six linking arms 20a-20f that are respectively linked to the lysine residues. According to the embodiments of the present disclosure, the linking arm is a PEG chain having 2-20 repeats of EG units.

Unlike the liker unit 10A of FIG. 4A, the linker unit 10B further comprises a coupling arm 60. As discussed above, a PEG chain having a maleimide group at one end and a functional group at the other end is used to form the coupling arm 60. In this way, the coupling arm 60 is linked to the cysteine residue of the center core 11b via thiol-maleimide reaction. In this example, the functional group at the free terminus of the coupling arm 60 is a tetrazine group 72. According to the embodiments of the present disclosure, the coupling arm is a PEG chain having 2-12 repeats of EG units.

When the release of effector elements at the targeted site is required, a cleavable bond can be installed in the linking arm. Such a bond is cleaved by acid/alkaline hydrolysis, reduction/oxidation, or enzymes. One embodiment of a class of cleavable PEG chains that can be used to form the coupling arm is NHS-PEG$_{2-20}$-S-S-maleimide, where S—S is a disulfide bond that can be slowly reduced, while the NHS group is used for conjugating with the amine group of the center core, thereby linking the PEG chain onto the center core. The maleimide group at the free terminus of the linking arm may be substituted by an azide, alkyne, tetrazine, or strained alkyne group.

According to certain embodiments of the present disclosure, the linking arm that is linked to the K residue of the center core has a maleimide group at its free terminus. In this way, a functional element (such as, an effector element) having a thiol group may react with the maleimide group of the linking arm via the thiol-maleimide reaction so that the functional element is linked to the linking arm. For the sake of illustration, the functional elements linked to the linking arms are referred to as the first elements. As could be appreciated, the number of the first elements carried by the present linker unit depends on the number of K residues of the center core (and thus, the number of the linking arms).

Accordingly, one of ordinary skill in the art may adjust the number of the first elements of the linker unit as necessary, for example, to achieve the desired targeting or therapeutic effect.

Figure 4C:
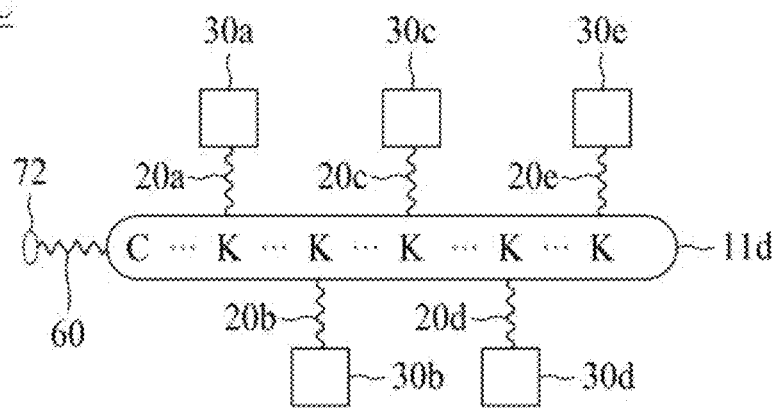

An example of a linker unit 10C having the first elements is illustrated FIG. 4C. Other than the features disused hereafter, FIG. 4C is quite similar to FIG. 4B. First, there are five K residues in the center core 11d, and accordingly, five linking arms 20a-20e are linked thereto, respectively. Second, the linker unit 10C has five first elements 30a-30e linked to each of the linking arms 20a-20e. As disused below, the optional tetrazine group 72 allows for the conjugation with an additional functional element, another molecular construct (e.g., those disclosed in Part I above). In particular, the first elements are effector elements such as drug molecules for treating tumors. Examples of drug molecules suitable for use in embodiments of the present disclosure include, but are not limited to, those disclosed above in Part I.

In order to increase the intended or desired effect (e.g., the therapeutic effect), the present linker unit may further comprise a second element in addition to the first element. In optional embodiments of the present disclosure, the first element is an effector element, while the second element may be another effector element, which works additively or synergistically with or independently of the first element. Alternatively, the first element is an effector element, and the second element is an element capable of improving the pharmacokinetic property of the linker unit, such as solubility, clearance, half-life, and bioavailability.

According to an alternative embodiment of the present disclosure, the first element is the effector element and the second element is the targeting element. For example, in the treatment of autoimmune disease, the present linker unit may comprise one targeting element that specifically targets the tissue-associated extracellular matrix protein (e.g., α-agrecan, collagen I, collagen II, collagen III, collagen V, collagen VII, collagen IX, and collagen XI) and a plurality of effector elements that produce an therapeutic effect on the lesion site.

Structurally, the second element is linked to the azide, alkyne, tetrazine, or strained alkyne group at the N- or C-terminus of the center core. Specifically, the second element may be optionally conjugated with a short PEG chain (preferably having 2-12 repeats of EG units) and then linked to the N- or C-terminal amino acid residue having an azide group or an alkyne group (e.g., AHA residue or HPG residue). Alternatively, the second element may be optionally conjugated with the short PEG chain and then linked to the coupling arm of the center core.

According to some embodiments of the present disclosure, the center core comprises an amino acid having an azide group (e.g., the AHA residue) at its N- or C-terminus; and accordingly, a second element having an alkyne group is linked to the N- or C-terminus of the center core via the CuAAC reaction. According to other embodiments of the present disclosure, the center core comprises an amino acid having an alkyne group (e.g., the HPG residue) at its N- or C-terminus; and a second element having an azide group is thus capable of being linked to the N- or C-terminus of the center core via the "Copper(I)-catalyzed alkyne-azide cycloaddition (CuAAC)" reaction (or the "click" reaction for short) as exemplified in Scheme 1.

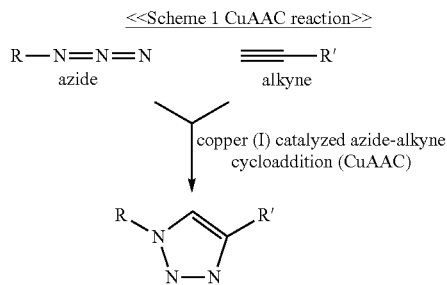

<<Scheme 1 CuAAC reaction>>

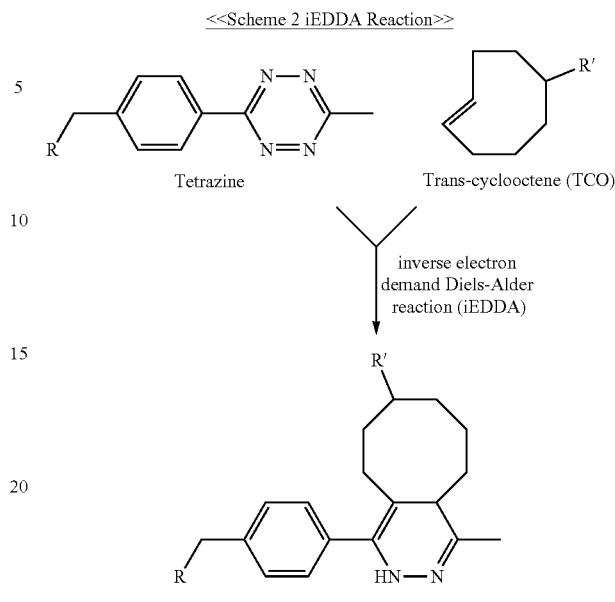

<<Scheme 2 iEDDA Reaction>>

The CuAAC reaction yields 1,5 di-substituted 1,2,3-triazole. The reaction between alkyne and azide is very selective and there are no alkyne and azide groups in natural biomolecules. Furthermore, the reaction is quick and pH-insensitive. It has been suggested that instead of using copper (I), such as cuprous bromide or cuprous iodide, for catalyzing the click reaction, it is better to use a mixture of copper (II) and a reducing agent, such as sodium ascorbate to produce copper (I) in situ in the reaction mixture. Alternatively, the second element can be linked to the N- or C-terminus of the present center core via a copper-free reaction, in which pentamethylcyclopentadienyl ruthenium chloride complex is used as the catalyst to catalyze the azide-alkyne cycloaddition.

Figure 4D:
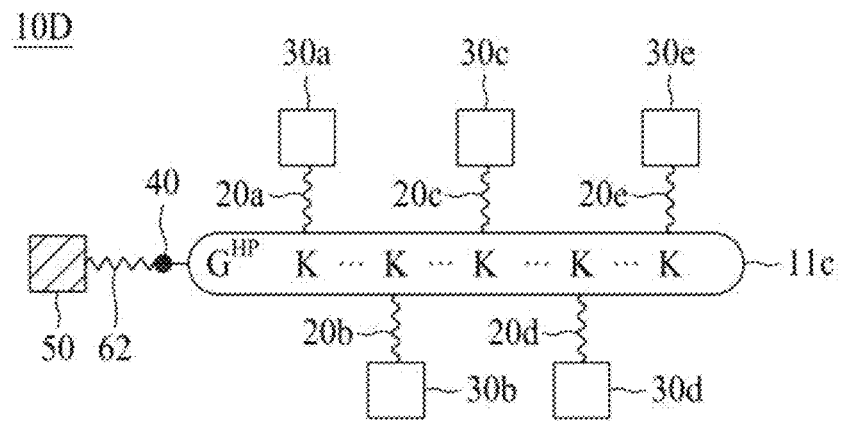

FIG. 4D provides an example of the present linker unit carrying a plurality of first elements and one second element. In this example, the center core 11c comprises one HPG ($G^{HP}$) residue and five lysine (K) residues. Five linking arms 20a-20e are respectively linked to the five K residues of the center core 11c; and five first elements 30a-30e are respectively linked to said five linking arms 20a-20e via the thiol-maleimide reaction. In addition to the first elements, the linker unit 10D further comprises an Fc-based molecular construct 50 (e.g., those discussed above in Part I of the present disclosure) that is linked to one end of a short PEG chain 62. Before being conjugated with the center core 11c, the other end of the short PEG chain 62 has an azide group. In this way, the azide group may reacted with the HPG residue that having an alkyne group via CuAAC reaction, so that the Fc-based molecular construct 50 is linked to the center core 11c. The solid dot 40 depicted in FIG. 4D represents the chemical bond resulted from the CuAAC reaction occurred between the HPG residue and the azide group.

Alternatively, the second element is linked to the center core via a coupling arm. According to certain embodiments of the present disclosure, the coupling arm has a tetrazine group, which can be efficiently linked to a second element having a TCO group via the inverse electron demand Diels-Alder (iEDDA) reaction (see, scheme 2). According to other embodiments of the present disclosure, the coupling arm has a TCO group, which is capable of being linked to a second element having a tetrazine group via the iEDDA reaction. In the iEDDA reaction, the strained cyclooctenes that possess a remarkably decreased activation energy in contrast to terminal alkynes is employed, and thus eliminate the need of an exogenous catalyst.

Figure 4E:
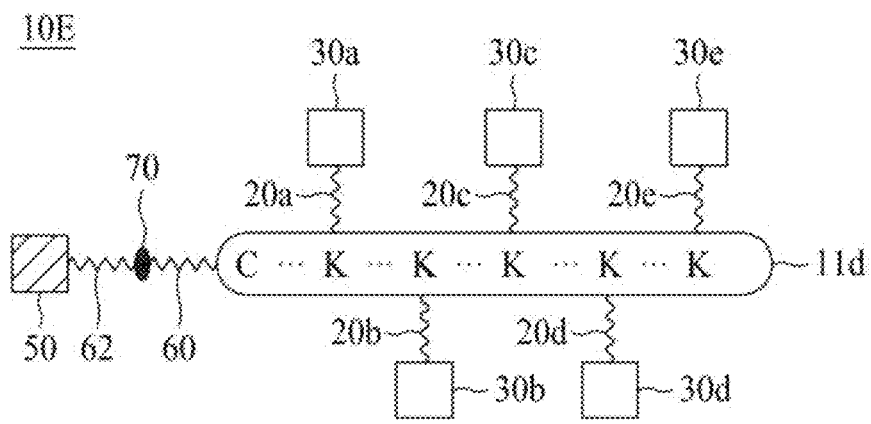

Reference is now made to FIG. 4E, in which the center core 11d comprises a terminal cysteine (C) residue and five lysine (K) residues. As depicted in FIG. 4E, five linking arms 20a-20e are respectively linked to the five K residue of the center core 11d, and then five first elements 30a-30e are respectively linked to the five linking arms 20a-20e via thiol-maleimide reactions. The cysteine residue is linked to the coupling arm 60, which, before being conjugated with the second element, comprises a tetrazine group or a TCO group at its free-terminus. In this example, a Fc-based molecular construct 50 linked with a short PEG chain 62 having a corresponding TCO or tetrazine group can be linked to the coupling arm 60 via the iEDDA reaction. The ellipse 70 as depicted in FIG. 4E represents the chemical bond resulted from the iEDDA reaction occurred between the coupling arm 60 and the short PEG chain 62.

According to other embodiments of the present disclosure, before the conjugation with a second element, the coupling arm has an azide group. As such, the coupling arm can be linked to the second element having a strained alkyne group (e.g., the DBCO, DIFO, BCN, or DICO group) at the free-terminus of a short PEG chain via SPAAC reaction (see, scheme 3), and vice versa.

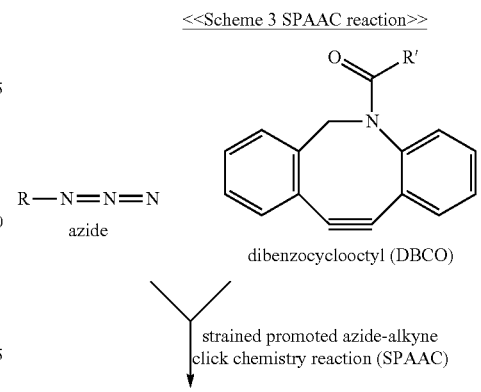

<<Scheme 3 SPAAC reaction>>

-continued

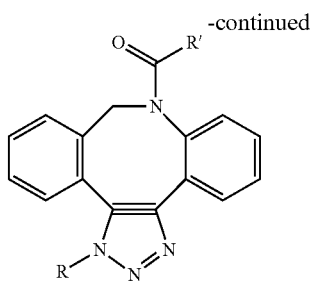

Scheme 4 is a scheme illustrating the coupling of the effector element with the polypeptide core, in which the linking arm is first linked to the center core, and then the effector element (i.e., the drug) is linked to the linking arm via the thiol-maleimide reaction. In the alternative method of scheme 5, the effector element (i.e., the drug) is coupled to the linking arm so as to produce a linking arm-effector conjugate (i.e., PEG-drug); next, the linking arm-effector conjugate is linked to the center core via forming an amide linkage between the lysine residues and the NHS esters.

<<Scheme 4 Method of coupling of effector element with polypeptide core through linking to linking arms>>

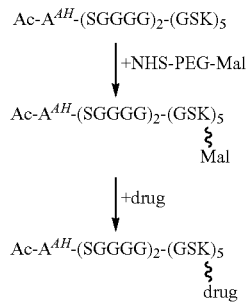

<<Scheme 5 Alternative Method of coupling of effector element with polypeptide core by first conjugating with PEG chain and then linking to amino groups of lysine residues>>

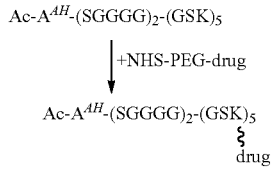

Figure 4F:
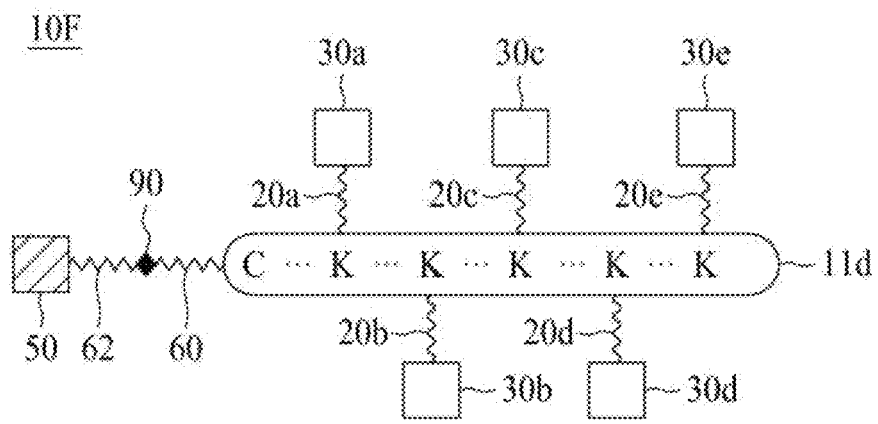

Reference is now made to FIG. 4F, in which the linker unit 10F has a structure similar to the linker unit 10E of FIG. 4E, except that the coupling arm 60 comprises an azide or a strained alkyne group (e.g., the DBCO, DIFO, BCN, or DICO group), instead of the tetrazine or TCO group. Accordingly, the Fc-based molecular construct 50 linked with a short PEG chain 62 may have a corresponding strained alkyne (e.g., DBCO, DIFO, BCN, or DICO) or azide group, so that it can be linked to the coupling arm 60 via the SPAAC reaction. The diamond 90 as depicted in FIG. 4F represents the chemical bond resulted from the SPAAC reaction occurred between the coupling arm 60 and the short PEG chain 62.

PEGylation is a process, in which a PEG chain is attached or linked to a molecule (e.g., a drug or a protein). It is known that PEGylation imparts several significant pharmacological advantages over the unmodified form, such as improved solubility, increased stability, extended circulating life, and decreased proteolytic degradation. According to one embodiment of the present disclosure, the second element is a PEG chain, which has a molecular weight of about 20,000 to 50,000 daltons.

Figure 4G:
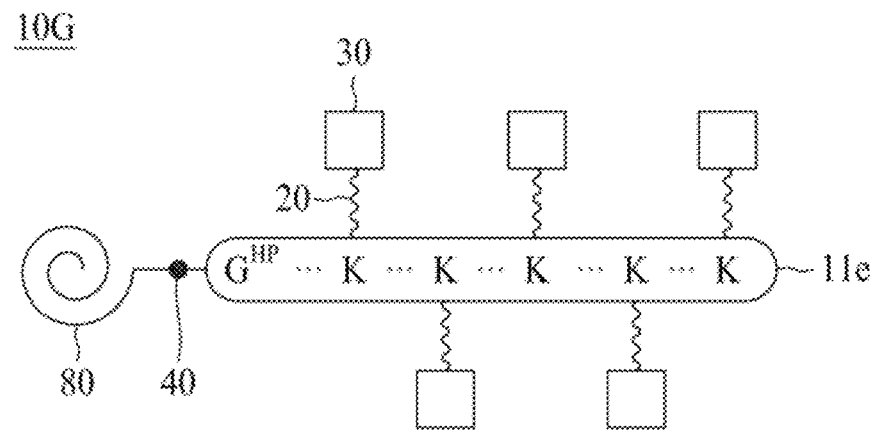

FIG. 4G provides an alternative example of the present linker unit (linker unit 10G), in which five first elements 30 are respectively linked to the lysine residues via the linking arms 20 and the AHA ($A^{AH}$) residue of the center core 11e is linked with a PEG chain 80 via the CuAAC reaction. The solid dot 40 depicted in FIG. 4G represents the chemical bond resulted from the CuAAC reaction occurred between the AHA residue and the PEG chain 80.

Figure 4H:
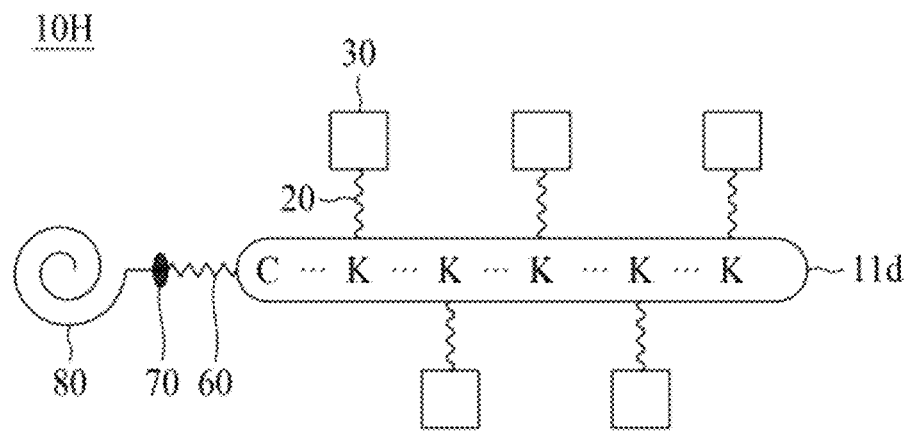

FIG. 4H provides another example of the present disclosure, in which the N-terminus of the center core 13 is a cysteine residue that is linked to a coupling arm 60. A PEG chain 80 can be efficiently linked to the coupling arm 60 via the iEDDA reaction. The ellipse 70 of the linker unit 10H represents the chemical bond resulted from the iEDDA reaction occurred between the coupling arm 60 and the PEG chain 80.

Figure 4I:
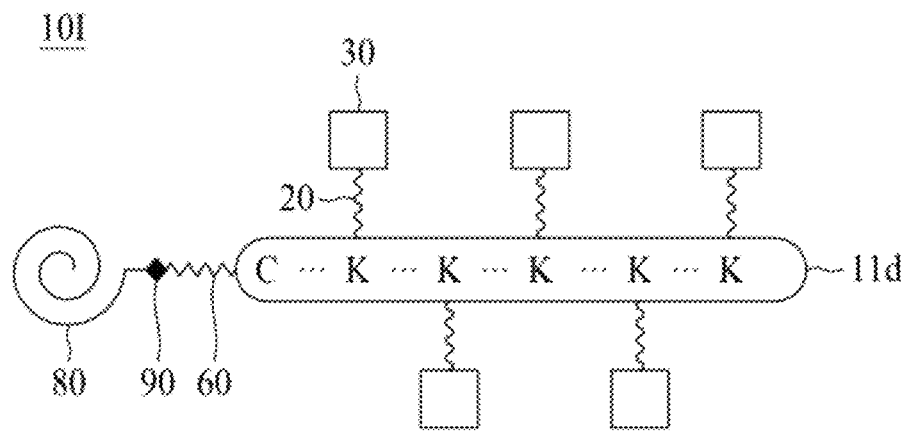

FIG. 4I provides an alternative example of the present linker unit, in which the linker unit 10I has a structure similar to the linker unit 10G of FIG. 4G, except that the PEG chain 80 is linked to the coupling arm 60 via the SPAAC reaction. The diamond 90 depicted in FIG. 4I represents the chemical bond resulted from the SPAAC reaction occurred between the coupling arm 60 and the PEG chain 80.

According to some embodiments of the present disclosure, in addition to the first and second elements, the present linker unit further comprises a third element. In this case, one of the N- and C-terminus of the center core is an amino acid having an azide group or an alkyne group, while the other of the N- and C-terminus of the center core is a cysteine residue. The lysine residues of the center core are respectively linked with the linking arms, each of which has a maleimide group at its free terminus; whereas the cysteine residue of the center core is linked with the coupling arm, which has a tetrazine group or a strained alkyne group at its free terminus. As described above, the first element is therefore linked to the linking arm via the thiol-maleimide reaction, and the second element is linked to the coupling arm via the iEDDA reaction. Further, a third element is linked to the terminal amino acid having an azide group or an alkyne group via the CuAAC reaction or SPAAC reaction.

Optionally, the first, second, and third elements are different. According to one embodiment of the present disclosure, the linker unit may have two different kinds of targeting elements and one kind of effector element, two different kinds of effector elements and one kind of targeting element, or one kind of targeting element, one kind of effector element, and one element capable of improving the pharmacokinetic property of the linker unit, such as solubility, clearance, half-life, and bioavailability.

Figure 4J:
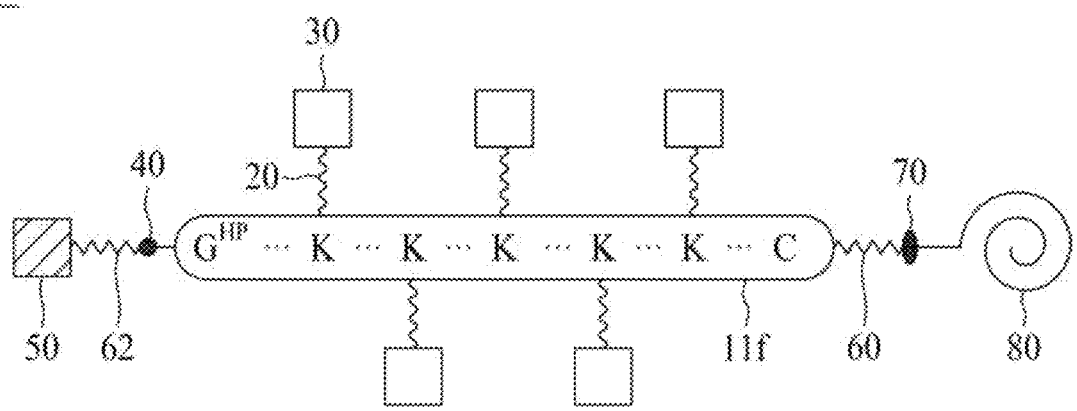

Reference is now made to the linker unit 10J of FIG. 4J, in which the center core 11f has an HPG ($G^{HP}$) residue at the N-terminus thereof and a cysteine residue at the C-terminus thereof. The linking arms 20 and the coupling arm 60 are respectively linked to the lysine (K) residues and the cysteine (C) residue of the center core 11f. Further, five first elements 30 are respectively linked to the five linking arms 20, the second element (i.e., the PEG chain) 80 is linked to the coupling arm 60 via the short PEG chain 62, and the Fc-based molecular construct 50 is linked to the HPG residue. The solid dot 40 indicated the chemical bond resulted from the CuAAC reaction occurred between the HPG residue and the short PEG chain 62; while the ellipse 70 represents the chemical bond resulted from the iEDDA reaction occurred between the coupling arm 60 and the PEG chain 80.

Figure 4K:
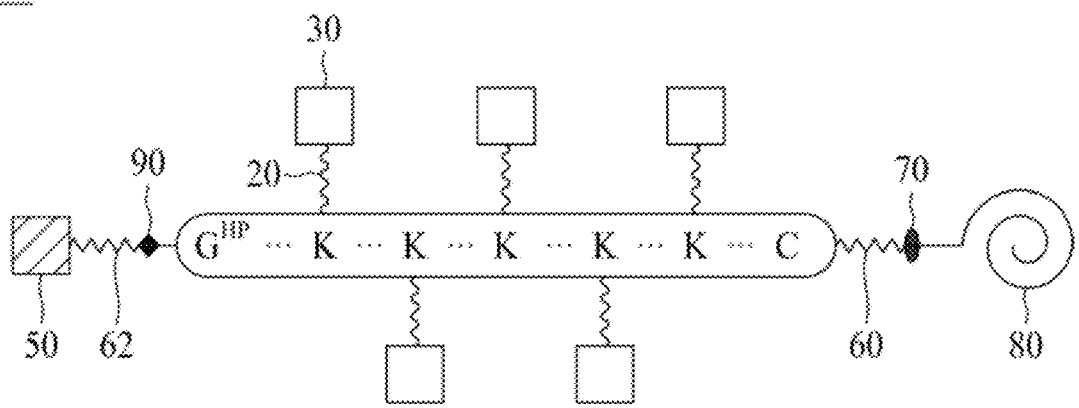

FIG. 4K provides another embodiment of the present disclosure, in which the linker unit 10K has the similar structure with the linker unit 10J of FIG. 4J, except that the short PEG chain 62 is linked with the HPG residue via the SPAAC reaction, instead of the iEDDA reaction. The diamond 90 in FIG. 4K represents the chemical bond resulted from the SPAAC reaction occurred between the short PEG chain 62 and the HPG residue.

In the preferred embodiments of this disclosure, the linking arms have a maleimide group in the free terminus for conjugating with first elements having the sulfhydryl group via the thiol-maleimide reaction. Also, there is one cysteine residue or an amino acid residue with an azide or alkyne group at a terminus of the peptide core for attaching a coupling arm for linking a second element.

In addition to the linker unit described above, also disclosed herein is another linker unit that employs a compound, instead of the polypeptide, as the center core. Specifically, the compound is benzene-1,3,5-triamine, 2-(aminomethyl)-2-methylpropane-1,3-diamine, tris(2-aminoethyl)amine, benzene-1,2,4,5-tetraamine, 3,3',5,5'-tetraamine-1,1'-biphenyl, tetrakis(2-aminoethyl)methane, tetrakis-(ethylamine)hydrazine, N,N,N',N',-tetrakis(aminoethyl)ethylenediamine, benzene-1,2,3,4,5,6-hexaamine, 1-N,1-N,3-N,3-N,5-N,5-N-hexakis(methylamine)-benzene-1,3,5-triamine, 1-N,1-N,2-N,2-N,4-N,4-N,5-N,5-N,-octakis(methylamine)-benzene-1,2,4,5-triamine, benzene-1,2,3,4,5,6-hexaamine, or N,N-bis[(1-amino-3,3-diaminoethyl)pentyl]-methanediamine. Each of these compounds has 3 or more amine groups in identical or symmetrical configuration. Therefore, when one of the amine groups of a compound is conjugated with a coupling arm, all of the molecules of the compound have the same configuration.

Similar to the mechanism of linkage described above, each compound listed above comprises a plurality of amine groups, and thus, a plurality of PEG chains having NHS groups can be linked to the compound via forming an amine linkage between the amine group and the NHS group; the thus-linked PEG chain is designated as linking arm, which has a maleimide group at the free-terminus thereof. Meanwhile, at least one of the amine groups of the compound core is linked to another PEG chain, which has an NHS group at one end, and a functional group (e.g., an azide, alkyne, tetrazine, or strained alkyne group) at the other end; the thus-linked PEG chain is designated as coupling arm, which has a functional group at the free-terminus thereof.

Accordingly, two different elements can be respectively linked to the linking arm and/or coupling arm via the thiol-maleimide reaction (the linkage between the element and the linking arm) and the CuAAC reaction, SPAAC reaction or the iEDDA reaction (the linkage between the element and the coupling arm).

According to some embodiments of the present disclosure, the linking arm is a PEG chain having 2-20 repeats of EG units; and the coupling arm is a PEG chain having 2-12 repeats of EG unit. In one embodiment, both the linking and coupling arms have 12 repeats of EG unit, in which one terminus of the coupling arm is an NHS group, and the other terminus of the coupling arm is an alkyne group.

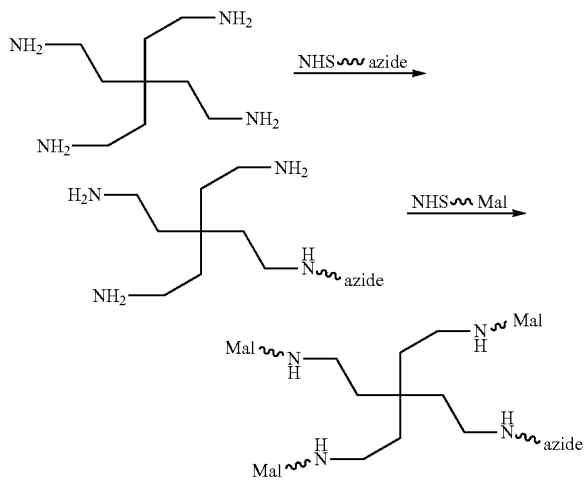

<<Scheme 6 Linkage of linking and coupling arms respectively having maleimide group and azide group to center core>>

Schemes 6 and 7 respectively depict the linkages between the center core, and the linking arm and the coupling arm, in which NHS represents NHS ester, Mal represents maleimide group, azide represents azide group, and alkyne represents alkyne group.

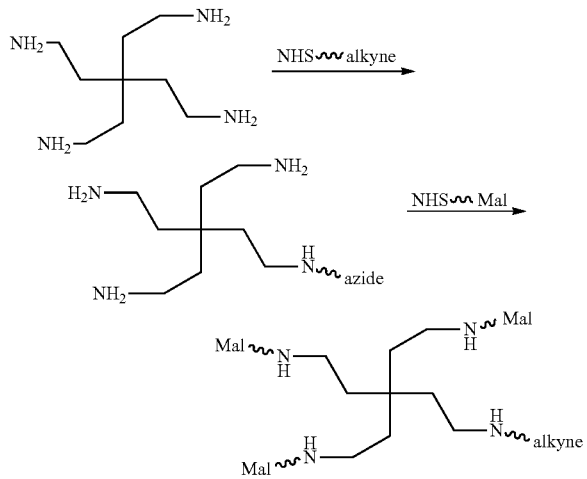

<<Scheme 7 Linkage of linking and coupling arms respectively having maleimide group and alkyne group to center core>>

The requirement of having multiple $NH_2$ groups exist in a symmetrical and identical orientation in the compound serving as the center core is for the following reason: when one of the $NH_2$ group is used for connecting a bifunctional linker arm with N-hydroxysuccinimide (NHS) ester group and alkyne, azide, tetrazine, or strained alkyne group, the product, namely, a core with a coupling arm having alkyne, azide, tetrazine or strained alkyne, is homogeneous and may be purified. Such a product can then be used to produce multi-arm linker units with all other $NH_2$ groups connected to linking arms with maleimide or other coupling groups at the other ends. If a compound with multiple $NH_2$ groups in non-symmetrical orientations, the product with one bifunctional linking arm/coupling arms is not homogeneous.

Some of those symmetrical compounds can further be modified to provide center cores with more linking arms/coupling arms. For example, tetrakis(2-aminoethyl)methane, which can be synthesized from common compounds or obtained commercially, may be used as a core for constructing linker units with four linking arms/coupling arms. Tetrakis(2-aminoethyl)methane can react with bis(sulfosuccinimidyl)suberate to yield a condensed product of two tetrakis (2-aminoethyl)methane molecules, which can be used as a core for constructing linker units having six linking arms/coupling arms. The linker units, respectively having 3 linking arms/coupling arms, 4 linking arms/coupling arms and 6 linking arms/coupling arms, can fulfill most of the need for constructing targeting/effector molecules with joint-linker configuration.

As would be appreciated, the numbers of the linking arm and/or the coupling arm and the element linked thereto may vary with the number of amine groups comprised in the center core. In some preferred embodiments, the numbers of the linking arm/coupling arm and the corresponding linking element linked thereto ranges from about 1-7.

Figure 5:
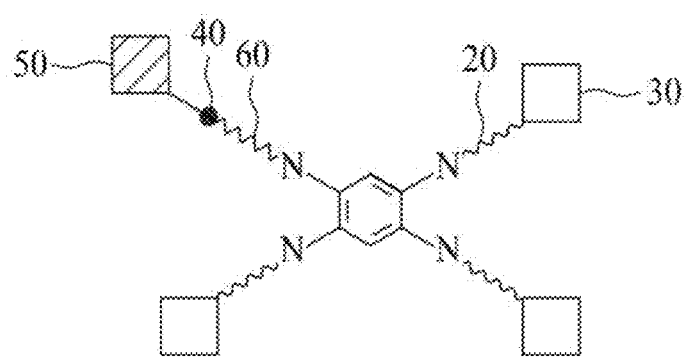
FIG. 5 is a schematic diagram illustrating a linker unit having a compound core.

Reference is now made to FIG. 5, in which benzene-1,2,4,5-tetraamine having 4 amine groups is depicted. Three of the amine groups are respectively linked to the linking arms 20, and one of the amine group is linked to the coupling arm 60, which has an azide group at its free-terminus. Three first elements 30 are then respectively linked to the three linking arms 20 via the thiol-maleimide reactions, and one Fc-based molecular construct 50 is linked to the coupling arm 60 via the CuAAC reaction. The solid dot 40 as depicted in FIG. 5 represents the chemical bond resulted from the CuAAC reaction occurred between the coupling arm 60 and the Fc-based molecular construct 50.

It is conceivable for those skilled in the arts that variations may be made. A conjugating group, other than maleimide, such as azide, alkyne, tetrazine, or strained alkyne may be used for the free terminus of the linking arms, for linking with first elements with a CuAAC, iEDDA, or SPAAC reaction. Also the cysteine residue (or an amino acid residue with an azide or alkyne group) of the peptide core needs not to be at the N- or C-terminus. Furthermore, two or more of such residues may be incorporated in the peptide core to attach multiple coupling arms for linking a pleural of second elements.

Compared with previously known therapeutic constructs, the present linker unit discussed in Part I is advantageous in two points:

(1) The number of the functional elements may be adjusted in accordance with the needs and/or applications. The present linker unit may comprise two elements (i.e., the first and second elements) or three elements (i.e., the first, second, and third elements) in accordance with the requirements of the application (e.g., the disease being treated, the route of administration of the present linker unit, and the binding avidity and/or affinity of the antibody carried by the present linker unit). For example, when the present linker unit is directly delivered into the tissue/organ (e.g., the treatment of eye), one element acting as the effector element may be enough, thus would eliminate the need of a second element acting as the targeting element. However, when the present linker unit is delivered peripherally (e.g., oral, enteral, nasal, topical, transmucosal, intramuscular, intravenous, or intraperitoneal injection), it may be necessary for the present linker unit to simultaneously comprise a targeting element that specifically targets the present linker unit to the lesion site; and an effector element that exhibits a therapeutic effect on the lesion site. For the purpose of increasing the targeting or treatment efficacy or increasing the stability of the present linker unit, a third element (e.g., a second targeting element, a second effector element, or a PEG chain) may be further included in the present linker unit.

(2) The first element is provided in the form of a bundle. As described in Part III of the present disclosure, the number of the first element may vary with the number of lysine residue comprised in the center core. If the number of lysine residue in the center core ranges from 2 to 15, then at least two first elements may be comprised in each linker unit. Thus, instead of providing one single molecule (e.g., cytotoxic drug and antibody) as traditional therapeutic construct or method may render, the present linker unit is capable of providing more functional elements (either as targeting elements or as effector elements) at one time, thereby greatly improves the therapeutic effect.

EXPERIMENTAL EXAMPLES

Example 1: Synthesis of Peptide 1 (SEQ ID NO: 17), Peptide 2 (SEQ ID NO: 18), and Peptide 3 (SEQ ID NO: 19) as Peptide Cores, and Conjugation of SH Group of Cysteine Residue with Maleimide-PEG$_3$-Transcyclooctene (TCO) as Conjugating Arm Peptides 1 to 3 were synthesized by solid-phase peptide synthesis method and purified with reverse phase high-performance liquid chromatography (HPLC) using Shimadzu Nexera-i LC-2040C 3D HPLC system to 95% purity. The reverse phase HPLC used a Kromasil 100-5C18 column (250 mm×4.6 mm; 5 μm), with a mobile phase of acetonitrile and 0.1% trifluoroacetic acid, a linear gradient of 10% to 45% acetonitrile over 15 minutes, at a flow rate of 1.0 mL/min and a column temperature of 25° C.

Figure 6:
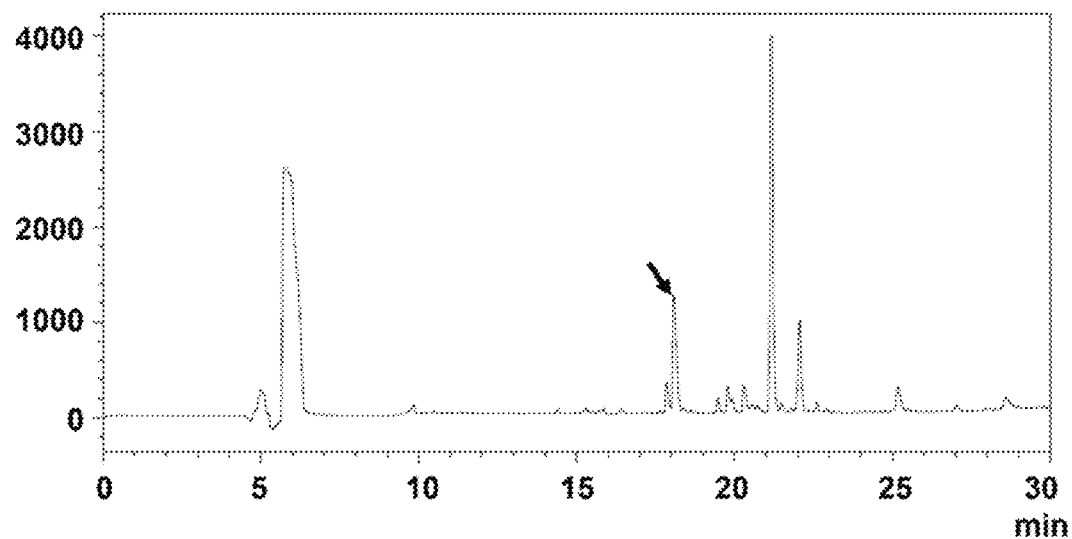
FIG. 6 shows the reverse phase HPLC elution profile for the purification of TCO-peptide 2. Peptide 2 is SEQ ID NO: 18.

The purified peptide was dissolved in 100 mM sodium phosphate buffer (pH 7.0) containing 50 mM NaCl and 5 mM EDTA at a final concentration of 2 mM. The dissolved peptide was reduced by 1 mM tris(2-carboxyethyl)phosphine (TCEP) at 25° C. for 2 hours. For conjugating the SH group of the cysteine residue with maleimide-PEG$_3$-TCO (Conju-probe Inc., San Diego, USA) to create a functional linking group TCO, the peptide and maleimide-PEG$_3$-TCO were mixed at a 1/10 ratio and incubated at pH 7.0 and 25° C. for 24 hours. TCO-conjugated peptides were purified by reverse phase HPLC on a Supelco C18 column (250 mm×10 mm; 5 μm), using a mobile phase of acetonitrile and 0.1% trifluoroacetic acid, a linear gradient of 0% to 100% acetonitrile over 30 minutes, at a flow rate of 1.0 mL/min and a column temperature of 25° C. FIG. 6 showed the reverse phase HPLC elution profile for the purification of TCO-peptide 2; with the peak of the TCO-peptide 2 being indicated with an arrow.

The identification of the three synthesized TCO-peptides (illustrated below) was carried out by mass spectrometry MALDI-TOF. Mass spectrometry analyses were performed by Mass Core Facility of Institute of Molecular Biology (IMB), Academia Sinica, Taipei, Taiwan. Measurements were performed on a Bruker Autoflex III MALDI-TOF/TOF mass spectrometer (Bruker Daltonics, Bremen, Germany).

The present TCO-peptide 1, as illustrated below, had a molecular weight (m.w.) of 1807.0 daltons.

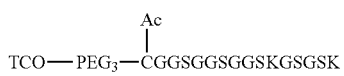

The present TCO-peptide 2, as illustrated below, had a m.w. of 2078.9 daltons.

The present TCO-peptide 3, as illustrated below, had a m.w. of 3380.8 daltons.

Example 2: Synthesis of Peptides 1 and 2 as Peptide Cores, and Conjugation of SH Group of Cysteine Residue with Maleimide-PEG$_4$-Tetrazine as Conjugating Arm Peptides 1 and 2 were prepared as in Example 1, and then dissolved in 100 mM sodium phosphate buffer (pH 7.0) containing 50 mM NaCl and 5 mM EDTA at 2 mM final concentration. The dissolved peptide was reduced by 1 mM TCEP at 25° C. for 2 hours. For conjugating the SH group of cysteine residue with maleimide-PEG$_4$-tetrazine (Conjuprobe Inc.) to create a functional linking group tetrazine, the peptide and maleimide-PEG$_4$-tetrazine were mixed at a 1/5 ratio and incubated at pH 7.0 and 4° C. for 24 hours. Tetrazine-conjugated peptides were purified by reverse phase HPLC on a Supelco C18 column (250 mm×10 mm; 5 μm), using a mobile phase of acetonitrile and 0.1% trifluoroacetic acid, a linear gradient of 0% to 100% acetonitrile over 30 minutes, at a flow rate of 1.0 mL/min and a column temperature of 25° C. The identification of said two synthesized tetrazine-peptides was carried out by mass spectrometry MALDI-TOF set forth in the preceding Example.

The present tetrazine-peptide 1, as illustrated below, had a m.w. of 1912.7 daltons.

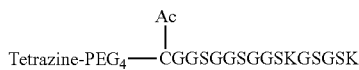

The present tetrazine-peptide 2, as illustrated below, had a m.w. of 2185.2 daltons.

Example 3: Synthesis of Peptides 1 and 2 as Peptide Cores, and Conjugation of SH Group of Cysteine Residue with Maleimide-PEG$_5$-DBCO as Conjugating Arm Peptides 1 and 2 were prepared as in the earlier Example. The peptide was dissolved in 100 mM sodium phosphate buffer (pH 7.0) containing 50 mM NaCl and 5 mM EDTA at 2 mM final concentration. The dissolved peptide was reduced by 1 mM TCEP at 25° C. for 2 hours. For conjugating the SH group of cysteine residue with dibenzylcyclooctyne (DBCO) to create a functional linking group of DBCO, the peptide and maleimide-PEG$_5$-DBCO (Conjuprobe Inc.) were mixed at a 1/5 ratio and incubated at pH 7.0 and the room temperature for 24 hours. DBCO-conjugated peptides were purified by reverse phase HPLC on a Supelco C18 column (250 mm×10 mm; 5 μm), using a mobile phase of acetonitrile and 0.1% trifluoroacetic acid, a linear gradient of 0% to 100% acetonitrile over 30 minutes, at a flow rate of 1.0 mL/min and a column temperature of 25° C. The identification of the two synthesized DBCO-peptides was carried out by mass spectrometry MALDI-TOF.

The present DBCO-peptide 1, as illustrated below, had a m.w. of 1941.8 daltons.

The present DBCO-peptide 2, as illustrated below, had a m.w. of 2213.9 daltons.

Example 4: Synthesis of Peptide 4 (SEQ ID NO: 21), Peptide 5 (SEQ ID NO: 22), and Peptide 6 (SEQ ID NO: 23) as Peptide Cores Peptides 4 to 6 were synthesized by solid-phase peptide synthesis method, and then purified by reverse phase HPLC to 95% purity. The unnatural amino acids, homopropagylglycine ($G^{HP}$) and azidohomoalanine ($A^{AH}$) contained an alkyne and an azide group, respectively. The reverse phase HPLC used a Supelco C18 column (250 mm×4.6 mm; 5 μm), with a mobile phase of acetonitrile and 0.1% trifluoroacetic acid, a linear gradient of 2% to 90% acetonitrile over 30 minutes, at a flow rate of 1.0 mL/min and a column temperature of 25° C.

The identification of said three synthesized peptides was carried out by mass spectrometry MALDI-TOF. The present peptide 4 (Ac-$G^{HP}$GGSGGSGGSKGSGSK; SEQ ID NO: 21) had a molecular weight of 1317.0 daltons; the present peptide 5 (Ac-$G^{HP}$GGSGGSGGSKGSGSKGSK; SEQ ID NO: 22) had a m.w. of 1589.9 daltons; while the present peptide 6 (Ac-$A^{AH}$GGSGGSGGSKGSGSKGSK; SEQ ID NO: 23) had a m.w. of 1634.66 daltons.

Example 5: Synthesis of Peptide 7 (SEQ ID NO: 24) as Peptide Core and Conjugation of SH Group of Cysteine Residue with Maleimide-PEG$_3$-TCO or Maleimide-PEG$_4$-Tetrazine as Conjugating Arm Peptide 7 (Ac-$G^{HP}$GGSGGSGGSKGSGSKGSGSC; SEQ ID NO: 24) was synthesized, and the conjugation of the crosslinkers was performed as described in above examples. The synthesized TCO-peptide 7 and tetrazine-peptide 7 were examined using MALDI-TOF.

The present TCO-peptide 7, as illustrated below, had a m.w. of 1736.78 daltons.

Ac-G$^{HP}$-GGSGGSGGSKGSGSKGSGSC-PEG$_3$-TCO

The present tetrazine-peptide 7, as illustrated below, had a m.w. of 1820.62 daltons.

Ac-G$^{HP}$-GGSGGSGGSKGSGSKGSGSC-PEG$_3$-Tetrazine

Example 6: Synthesis of Peptide 8 (SEQ ID NO: 25) as Peptide Core, and Conjugation of SH Group of Cysteine Residue with Maleimide-PEG$_3$-TCO, Maleimide-PEG$_4$-Tetrazine or Maleimide-PEG$_5$-DBCO as Conjugating Arm Peptide 8 (Ac-C-Xaa-K-Xaa-K-Xaa-K; wherein Xaa was a PEGylated amino acid with 2 EG units; SEQ ID NO: 25) was synthesized by solid-phase peptide synthesis method and then purified using reverse phase HPLC to 95% purity. The reversed phase HPLC was conducted using a Kromasil 100-5C18 column (250 mm×4.6 mm; 5 µm), with a mobile phase of water and 0.1% TFA, a linear gradient of 10% to 40% acetonitrile over 12 minutes, at a flow rate of 1.0 mL/min and a column temperature of 25° C.

The identification of the synthesized peptide 8 was carried out by mass spectrometry ESI-MS. High resolution and high mass accuracy experiments were done on a LTQ Orbitrap XL ETD mass spectrometer (Thermo Fisher Scientific, San Jose, Calif.) equipped with standard ESI ion source. Mass ESI-TOF analyses were performed by GRC Mass Core Facility of Genomics Research Center, Academia Sinica, Taipei, Taiwan. The sample of the synthesized peptide showed a strong molecular ion at 981.9, corresponding to [M−H]$^−$, indicating that the actual molecular weight of the PEGylated peptide was 983.0 daltons.

The conjugation of the crosslinkers was performed as described in above examples, and mass spectrometry ESI-MS was used to examine the products (illustrated below, in which the Xaa$_2$ denotes a PEGylated amino acid with two EG units).

The present TCO-peptide 8, as illustrated below, had a m.w. of 1478.87 daltons.

TCO-PEG$_5$-C-(Xaa$_2$-K)$_3$

The present tetrazine-peptide 8, as illustrated below, had a m.w. of 1584.92 daltons.

Tetrazine-PEG$_4$-C-(Xaa$_2$-K)$_3$

The present DBCO-peptide 8, as illustrated below, had a m.w. of 1613.8 daltons

DBCO-PEG$_5$-C-(Xaa$_2$-K)$_3$

Example 7: Synthesis of Peptide 9 (SEQ ID NO: 26) as Peptide Core, and Conjugation of SH Group of Cysteine Residue with Maleimide-PEG$_3$-TCO as Conjugating Arm Peptide 9 (Ac-C-Xaa-K-Xaa-K-Xaa-K-Xaa-K-Xaa-K; wherein Xaa was a PEGylated amino acid with 6 EG units; SEQ ID NO: 26) was prepared as set forth in an earlier Example. The identification of the synthesized peptide 9 was carried out by mass spectrometry ESI-MS. The sample of the synthesized peptide showed a strong molecular ion at 828.0, corresponding to [M+3H]$^{3+}$, indicating that the actual molecular weight of the PEGylated peptide was 2480.7 daltons.

The conjugation of the crosslinker was performed as set forth in above examples, and then examined with mass spectrometry ESI-MS. The present TCO-peptide 9, as illustrated below, had a m.w. of 2975 daltons.

TCO-PEG$_3$-C-(Xaa$_6$-K)$_5$

Example 8: Synthesis of Linker Unit by Conjugating NHS-PEG$_{12}$-Maleimide to NH$_2$ Groups of TCO-Peptides 1 and 2

Figure 7:
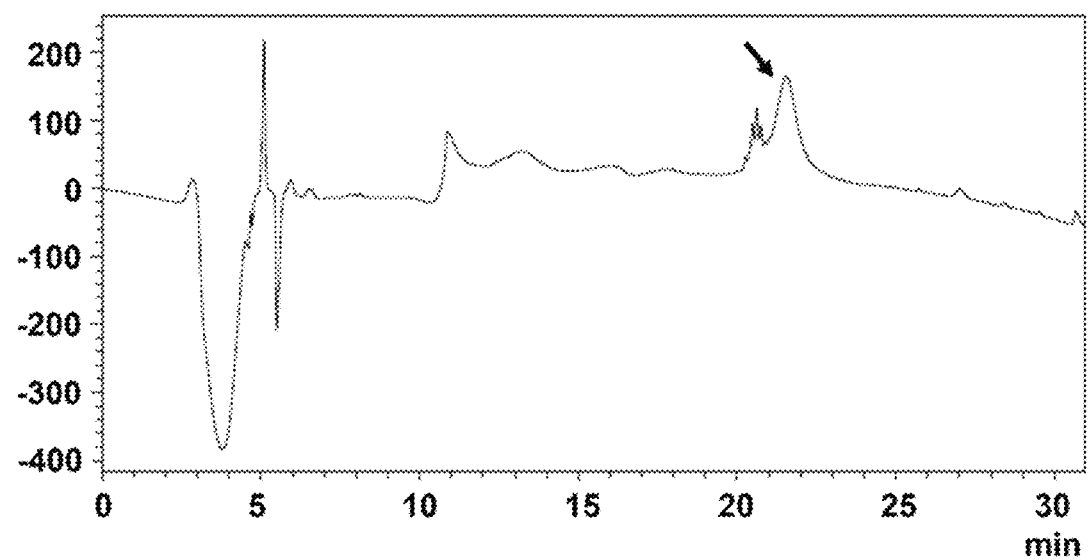
FIG. 7 shows the reverse phase HPLC profile for the purification of $PEG_{12}$-maleimide-conjugated TCO-peptide 2.

Two linking arms of PEG$_{12}$-maleimide were attached to the peptide core TCO-peptide 1; while three linking arms of PEG$_{12}$-maleimide were attached to the peptide core TCO-peptide 2. The crosslinker, NHS-PEG$_{12}$-maleimide (succinimidyl-[(N-maleimido-propionamido)-dodecaethyleneglycol] ester, was purchased from Thermo Fisher Scientific Inc. (Waltham, USA). The conjugation procedure was performed per the manufacturer's instruction; the peptide with lysine residues was dissolved in the conjugation buffer, phosphate buffered saline (PBS, pH 7.5) at 100 mM. NHS-PEG$_{12}$-maleimide crosslinker was added to the dissolved peptide at 1 mM final concentration (20-fold molar excess over 0.1 mM peptide solution). The reaction mixtures were incubated for 18 hours at room temperature. PEG$_{12}$-maleimide-conjugated TCO-peptide 1 and peptide 2 were purified by reverse phase HPLC on a Supelco C18 column (250 mm×4.6 mm; 5 µm), using a mobile phase of acetonitrile and 0.1% trifluoroacetic acid, a linear gradient of 0% to 100% acetonitrile over 30 minutes, at a flow rate of 1.0 mL/min and a column temperature of 25° C. FIG. 7 showed the reverse phase HPLC profile for the purification of PEG$_{12}$-maleimide-conjugated TCO-peptide 2, with the peak being indicated with an arrow.

The identification of the PEG$_{12}$-maleimide-conjugated TCO-peptide 1 and peptide 2 was carried out by mass spectrometry MALDI-TOF.

The present PEG$_{12}$-maleimide-conjugated TCO-peptide 1, as illustrated below, was a peptide core-based linker unit carrying one coupling arm with a TCO group and two PEG linking arms with maleimide groups. The result of mass spectrometry MALDI-TOF indicated that the present molecular construct had a m.w. of 3330.7 daltons.

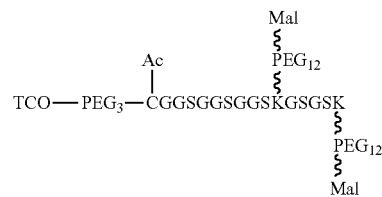

Figure 8:
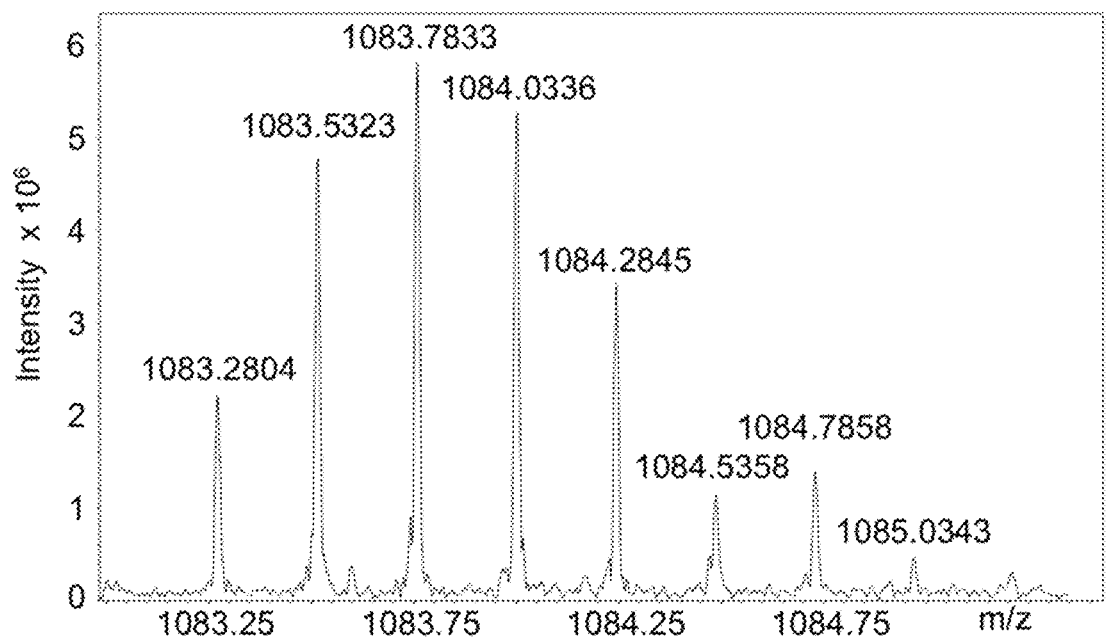
FIG. 8 shows the mass spectrometry MALDI-TOF result of $PEG_{12}$-maleimide-conjugated TCO-peptide 2.

The present PEG$_{12}$-maleimide-conjugated TCO-peptide 2, as illustrated below, was a peptide core-based linker unit carrying one coupling arm with a TCO group and three PEG linking arms with maleimide groups. FIG. 8 showed the mass spectrometry MALDI-TOF result, indicating that the present molecular construct had a m.w. of 4332 daltons; (ESI-TOF) m/z (z=4): [M+4H]$^+$; calculated for C$_{185}$H$_{313}$N$_{31}$O$_{83}$S$_1$ 1083.7829. found 1083.7833), corresponding to [M−Na]$^+$.

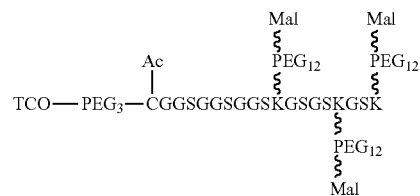

Example 9: Synthesis of Linker Unit by Conjugating NHS-PEG$_{12}$-Maleimide to NH$_2$ Groups of Tetrazine-Peptide 2 and DBCO-Peptide 1

Three linking arms of PEG$_{12}$-maleimide were attached to tetrazine-peptide 2, while two linking arms were attached to DBCO-peptide 1. The conjugation of NHS-PEG$_{12}$-maleimide to the NH$_2$ groups of the lysine residues of the peptide cores was performed as described in the earlier Examples, and the products were identified using mass spectrometry MALDI-TOF.

Figure 9A:
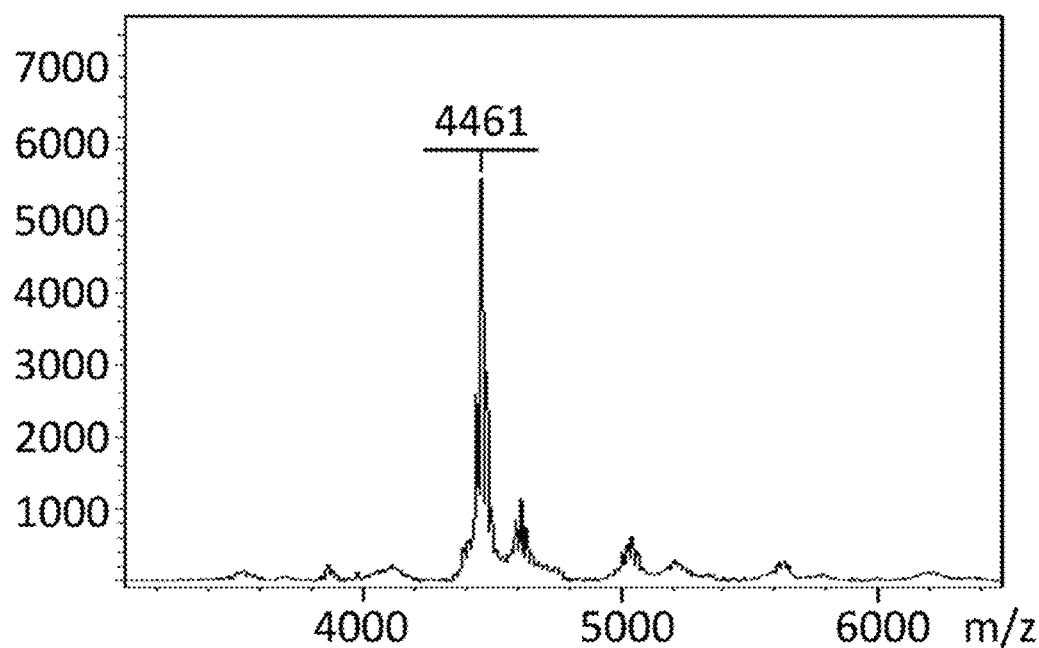
FIGS. 9A and 9B respectively show the mass spectrometry MALDI-TOF result of $PEG_{12}$-maleimide-conjugated tetrazine-peptide 2 and DBCO-peptide 2.

As illustrated below, the present PEG$_{12}$-maleimide-conjugated tetrazine-peptide 2 carried one coupling arm with a tetrazine group and three PEG linking arms with maleimide groups. FIG. 9A showed the mass spectrometry MALDI-TOF result, indicating that the construct had a m.w. of 4461 daltons.

```
                  Ac    Mal      Mal
                  |     §        §
                        PEG₁₂    PEG₁₂
                  |     §        §
Tetrazine-PEG₄—CGGSGGSGGSKGSGSKGSK
                               §
                               PEG₁₂
                               §
                               Mal
```

Figure 9B:
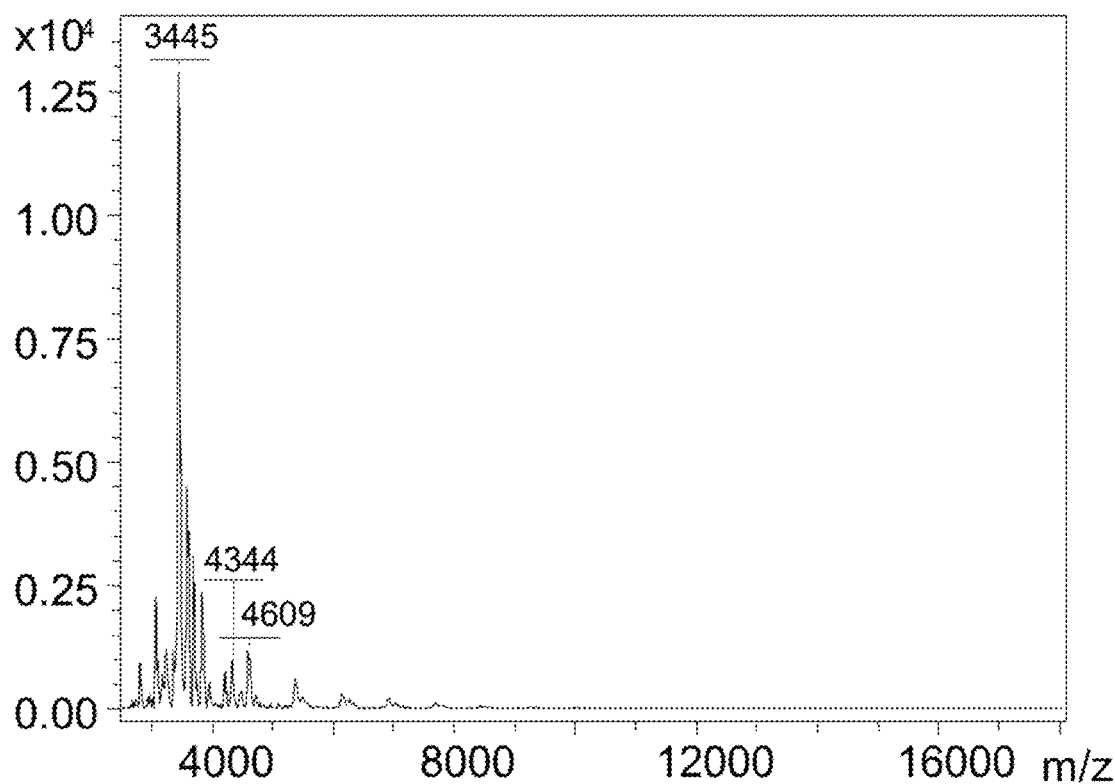

As illustrated below, the present PEG$_{12}$-maleimide-conjugated DBCO-peptide 1 carried one linking arm with a DBCO group and two PEG linking arms with maleimide groups. FIG. 9B showed the mass spectrometry MALDI-TOF result, indicating that the construct had had a m.w. of 3445 daltons.

```
                       Mal
                       §
                 Ac    PEG₁₂
                 |     §
DBCO—PEG₃—CGGSGGSGGSKGSGSK
                       §
                       PEG₁₂
                       §
                       Mal
```

Example 10: Synthesis of Linker Unit by Conjugating NHS-PEG$_{12}$-Maleimide to NH$_2$ Groups of Peptides 4 to 6

Two linking arms of PEG$_{12}$-maleimide were attached to the peptide 4; while three linking arms of PEG$_{12}$-maleimide were attached to the peptide 5 and peptide 6. The conjugation of NHS-PEG$_{12}$-maleimide to the NH$_2$ groups of the lysine residues of the peptide cores was performed as in the earlier Example, and the products were identified using mass spectrometry MALDI-TOF.

The present PEG$_{12}$-maleimide-conjugated peptide 4, as illustrated below, had a m.w. of 2817.3 daltons; it was a peptide core-based linker unit carrying one alkyne group and two PEG linking arms with maleimide groups.

The present PEG$_{12}$-maleimide-conjugated peptide 5 (illustrated below) had a m.w. of 3839.2 daltons; it was a peptide core-based linker unit carrying one alkyne group and three PEG linking arms with maleimide groups.

```
              Mal       Mal
              §         §
              PEG₁₂     PEG₁₂
              §         §
Ac—G^{HP}—GGSGGSGGSKGSGSKGSK
                        §
                        PEG₁₂
                        §
                        Mal
```

PEG$_{12}$-maleimide-conjugated peptide 6 (illustrated below) had a m.w. of 3811.5 daltons; it was a peptide core-based linker unit carrying one azide group and three PEG linking arms with maleimide groups.

```
              Mal       Mal
              §         §
              PEG₁₂     PEG₁₂
              §         §
Ac—A^{HA}—GGSGGSGGSKGSGSKGSK
                        §
                        PEG₁₂
                        §
                        Mal
```

Example 11: Synthesis of Linker Unit by Conjugating NHS-PEG$_{12}$-Maleimide to NH2 Groups of TCO-Peptide 7 and Tetrazine-Peptide 7

Two linking arms of PEG$_{12}$-maleimide were attached to a peptide core, the peptide 7 from the preceding Examples. The conjugation of NHS-PEG$_{12}$-maleimide to the NH$_2$ groups of the lysine residues of the peptide core was performed as described above, and the identification was carried out by mass spectrometry MALDI-TOF.

The present PEG$_{12}$-maleimide-conjugated TCO-peptide 7, as illustrated below, had a m.w. of 3237.63 daltons; it was a peptide core-based linker unit carrying one an alkyne group, one coupling arm with a TCO group, and two PEG linking arms with maleimide groups.

```
              Mal
              §
              PEG₁₂
              §
Ac—G^{HP}—GGSGGSGGSKGSGSKGSGSC—PEG₃—TCO
              §
              PEG₁₂
              §
              Mal
```

The present PEG$_{12}$-maleimide-conjugated tetrazine-peptide 7, as illustrated below, had a m.w. of 3342.98 daltons;

it was a peptide core-based linker unit carrying one alkyne group, one coupling arm with a tetrazine group, and two PEG linking arms with maleimide groups.

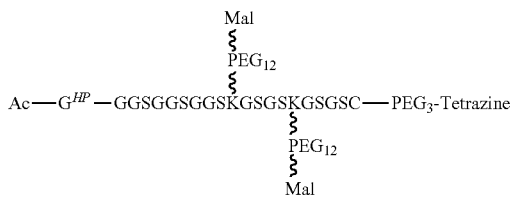

Example 12: Synthesis of Linker Unit by Conjugating NHS-PEG$_{12}$-Maleimide to NH2 Groups of TCO-Peptide 8 and Tetrazine-Peptide 8

Three linking arms of PEG$_{12}$-maleimide were attached to the peptide cores, TCO-peptide 8 and tetrazine-peptide 8. The conjugation of NHS-PEG$_{12}$-maleimide to the NH2 groups of the lysine residues of the peptide core was performed as in Example 8, and the identification was carried out by mass spectrometry MALDI-TOF.

The present PEG$_{12}$-maleimide-conjugated TCO-peptide 8 (illustrated below) had a m.w. of 3774.9 daltons; it was a linker unit based on PEGylated amino acid and lysine; it carried one coupling arm with a TCO group and three PEG linking arms with maleimide groups.

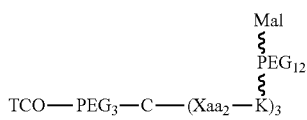

Figure 10:
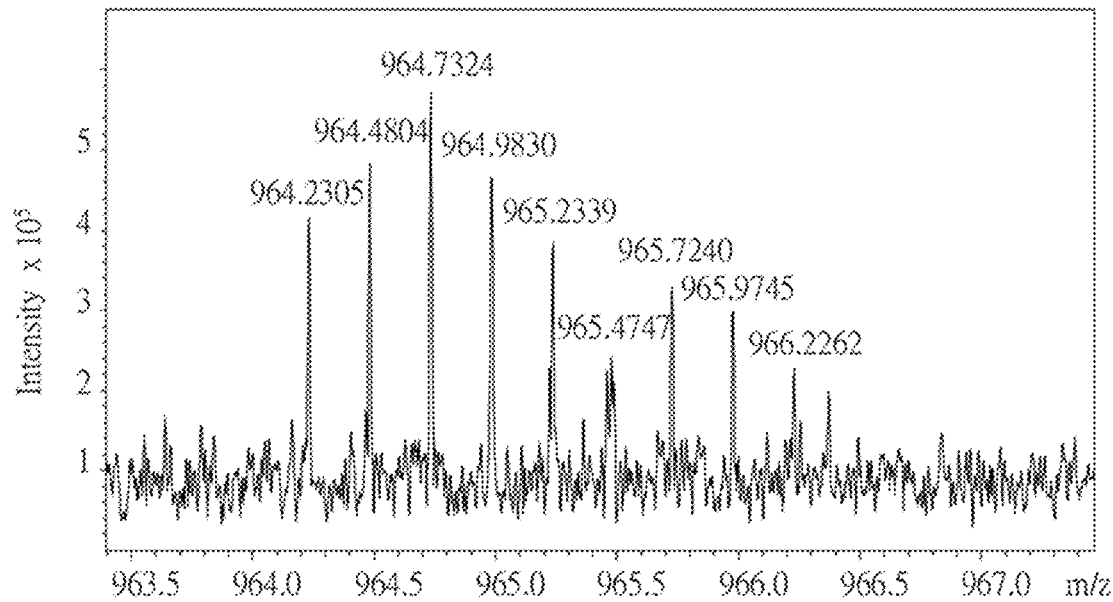
FIG. 10 shows the mass spectrometry ESI-TOF result of $PEG_{12}$-maleimide-conjugated tetrazine-peptide 8.

The present PEG$_{12}$-maleimide-conjugated tetrazine-peptide 8 (illustrated below) had a m.w. of 3856.94 daltons (FIG. 10; (ESI-TOF) m/z (z=4): [M+4H]$^+$ Calculated for C$_{171}$H$_{287}$N$_{23}$O$_{71}$S$_1$H$_3$Na 964.7363. Found 964.7324); it was a linker unit based on PEGylated amino acid and lysine; it carried one coupling arm with a tetrazine group and three PEG linking arms with maleimide groups.

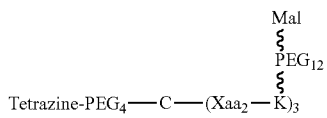

Example 13: Synthesis of Linker Unit by Conjugating NHS-PEG$_5$-Maleimide to NH2 Groups of TCO-Peptide 9

Five linking arms of PEG$_6$-maleimide were attached to the peptide cores, TCO-peptide 9. The conjugation of NHS-PEG$_6$-maleimide to the NH2 groups of the lysine residues of the peptide core was performed as in Example 8, the identification was carried out by mass spectrometry MALDI-TOF.

Figure 11:
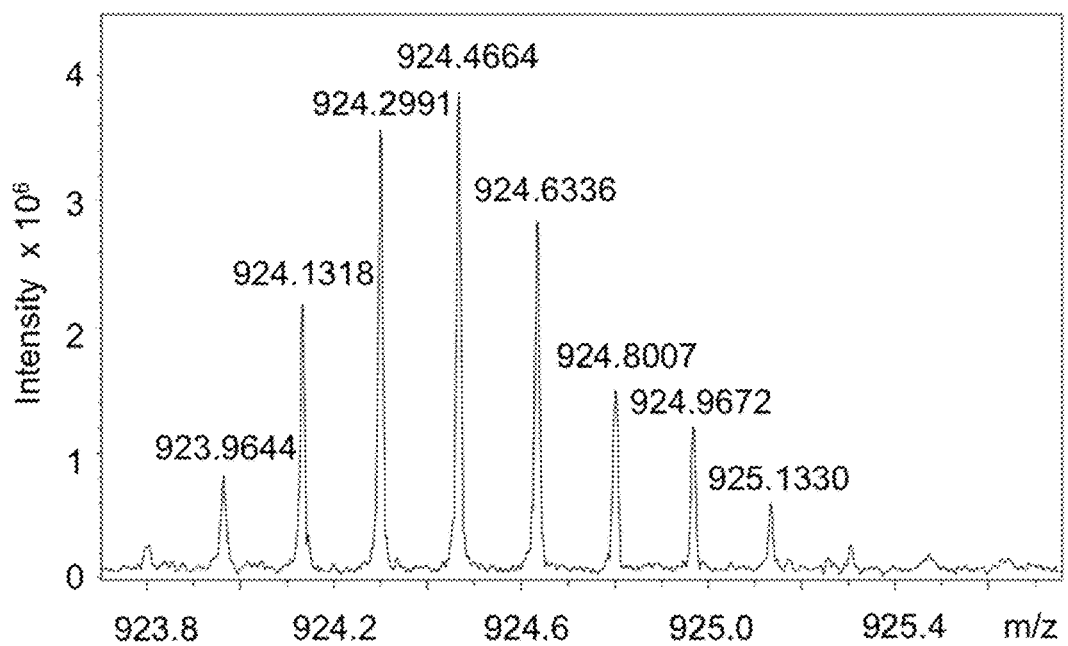
FIG. 11 shows the mass spectrometry ESI-TOF result of $PEG_{6}$-maleimide-conjugated TCO-peptide 9.

PEG$_6$-maleimide-conjugated TCO-peptide 9 (illustrated below) had a m.w. of 5543.78 daltons (FIG. 11; (ESI-TOF) m/z (z=6): [M+6H]$^+$ Calculated for C$_{244}$H$_{421}$N$_{29}$O$_{101}$S$_1$Na 924.297. Found 924.299); it was a linker unit based on PEGylated amino acid and lysine; it carried one coupling arm with a TCO group and five PEG linking arms with maleimide groups.

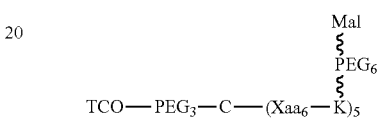

Example 14: Synthesis of Linker Unit with 1,3,5-Triaminobenzene Conjugated with 1 NHS-PEG$_{12}$-Alkyne Linking Arm and 2 NHS-PEG$_{12}$-Maleimide Linking Arms 1,3,5-triaminobenzene was purchased from BOC Sciences, Creative Dynamics Inc., NY, USA, and NHS-PEG$_{12}$-alkyne linking arm and NHS-PEG$_{12}$-maleimide from Thermo Fisher Scientific Inc. Waltham, Mass., USA. The conjugation of the linking arms employed a two-step procedure as shown in scheme 8. In step (i), 1,3,5-triaminobenzene was dissolved in the conjugation buffer (phosphate buffered saline, PBS, PH 7.2) at 1 mM and NHS-PEG$_{12}$-alkyne crosslinker was added to 1,3,5-triaminobenzene solution at 1 mM final concentration (1:1 molar ratio). Thereafter, 4 µl of the 250 mM NHS-PEG$_{12}$-alkyne stock solution was added to 1 ml of 1,3,5-triaminobenzene solution. The reaction mixtures were incubated for 1 hour at room temperature. In step (ii), NHS-PEG$_{12}$-maleimide crosslinker was added to the incubated solution in the step (i) at 10 mM final concentration (1:30 molar ratio). Next, 30 µl of the 250 mM NHS-PEG$_{12}$-maleimide stock solution was added to 125 µl of incubated solution; then 845 µl of the conjugation buffer was added to make the final solution 1 ml. The reaction mixtures were incubated for 2 hours at room temperature.

<<Scheme 8 Two-step synthesis of 1,3,5-triaminobenzene conjugated with one NHS-PEG$_{12}$-alkyne linking arm and two NHS-PEG$_{12}$-maleimide linking arms>>

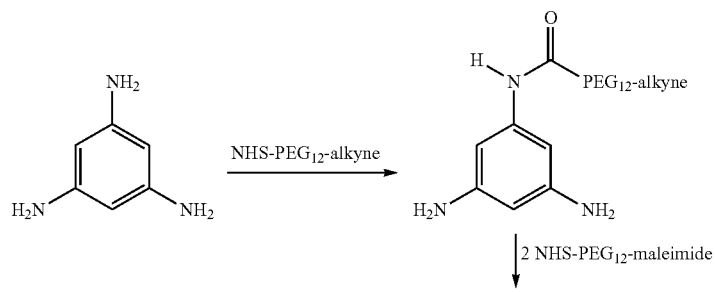

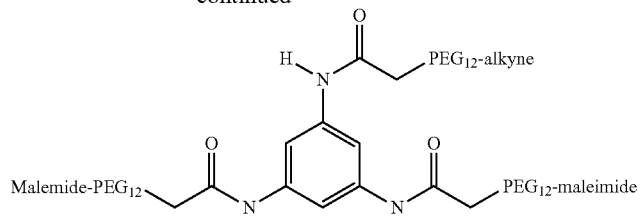

Figure 12:
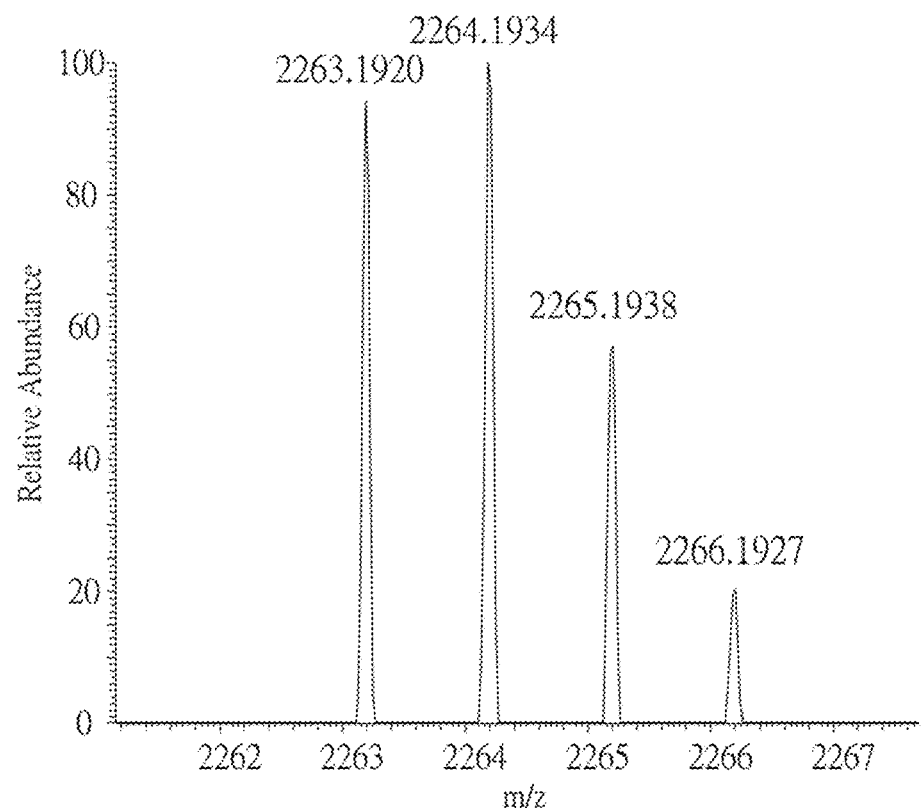
FIG. 12 shows the mass spectrometry ESI-TOF result of 1,3,5-triaminobenzene conjugated with one NHS-$PEG_{12}$-alkyne coupling arm and two NHS-$PEG_{12}$-maleimide linking arms.

The product, 1,3,5-triaminobenzene conjugated with one NHS-PEG$_{12}$-alkyne coupling arm and two NHS-PEG$_{12}$-maleimide linking arms, was purified by subjecting the reaction mixture through reverse phase HPLC column and collecting the fractions containing the linker unit. The product was analyzed by mass spectroscopy ESI (FIG. 12). The data showed (ESI-TOF) m/z: [M+H]$^+$—calculated for C$_{104}$H$_{180}$N$_7$O$_{46}$ 2263.1955. found 2263.1920. The three isotopic peaks were also visible in the MS spectrum at 2264.1934, 2265.1938 and 2266.1927, corresponding to [M+H+1]$^+$, [M+H+2]$^+$ and [M+H+3]$^+$.

Example 15: Conjugation of Five DM1-SMCC Molecules to TCO-Peptide 9

Figure 13:
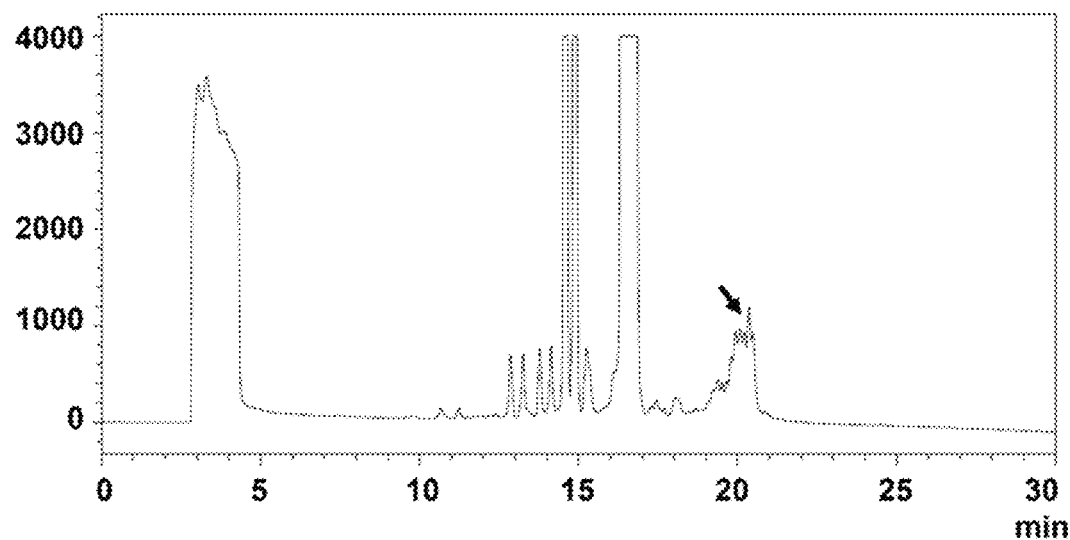
FIG. 13 shows the reverse phase HPLC profile for the purification of TCO-peptide 9 with 5 DM1-SMCC molecules.
Figure 14:
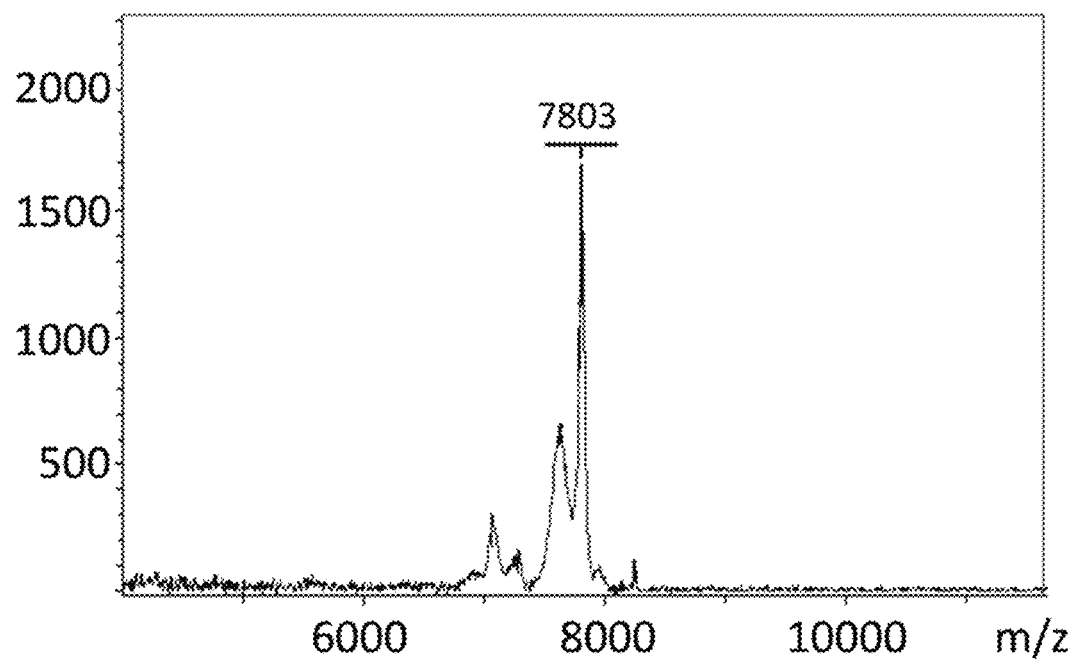
FIG. 14 shows the mass spectrometry result of TCO-peptide 9 with 5 DM1-SMCC molecules.

DM1-SMCC, which was N$_2$'-Deacetyl-N$_2$'-(3-mercapto-1-oxopropyl)-maytansine (DM1) modified by a linker, succinimidyl-4-(N-maleimidom-ethyl) cyclohexan-1-carboxylate (SMCC), was purchased from ALB Technology Inc., Hong Kong, China. TCO-peptide 9 with free amine groups was dissolved in 100 mM sodium phosphate buffered at pH 7.5. DM1-SMCC was added to the TCO-peptide 9 solution at 1 mM final concentration (25-fold molar excess over the 0.04 mM TCO-peptide 9 solution) by adding 4 µl of the 250 mM DM1-SMCC solution per milliliter of NH$_2$-containing TCO-peptide 9 solution. The reaction mixtures were incubated for 24 hours at room temperature. The reaction product was separated by HPLC and then lyophilized. The TCO-peptide 9 with five DM1-SMCC molecules was purified by reverse phase HPLC on a Supelco C18 column (250 mm×4.6 mm; 5 µm), using a mobile phase of acetonitrile and 0.1% trifluoroacetic acid, a linear gradient of 30% to 100% acetonitrile over 30 minutes, at a flow rate of 1.0 mL/min and a column temperature of 25° C. FIG. 13 showed the reverse phase HPLC profile for the purification of TCO-peptide 9 with five DM1-SMCC molecules (also referred to as a drug bundle); the peak being indicated with an arrow. The mass spectroscopic analysis of the thus-synthesized drug bundle, as provided in FIG. 14, indicated that the molecular construct had a m.w. of 7803 daltons.

The present drug bundle, as illustrated below, was composed of a linker unit with a free TCO functional group and a set of five DM1 molecules as effector elements.

Superdex 200 10/300 Tricon column (HR, GE Healthcare) in an AKTA Explorer FPLC system. The elution buffer, 50 mM HEPES, pH7.5, was used. The sample was injected and eluted isocratically at 0.5 mL/min and collected in 1-mL fractions. The fractions containing LPS were then dialyzed against MilliQ water using a 3500 MWCO membrane at 4° C. overnight. The dialyzed LPS were lyophilized for subsequent conjugation.

Figure 15:
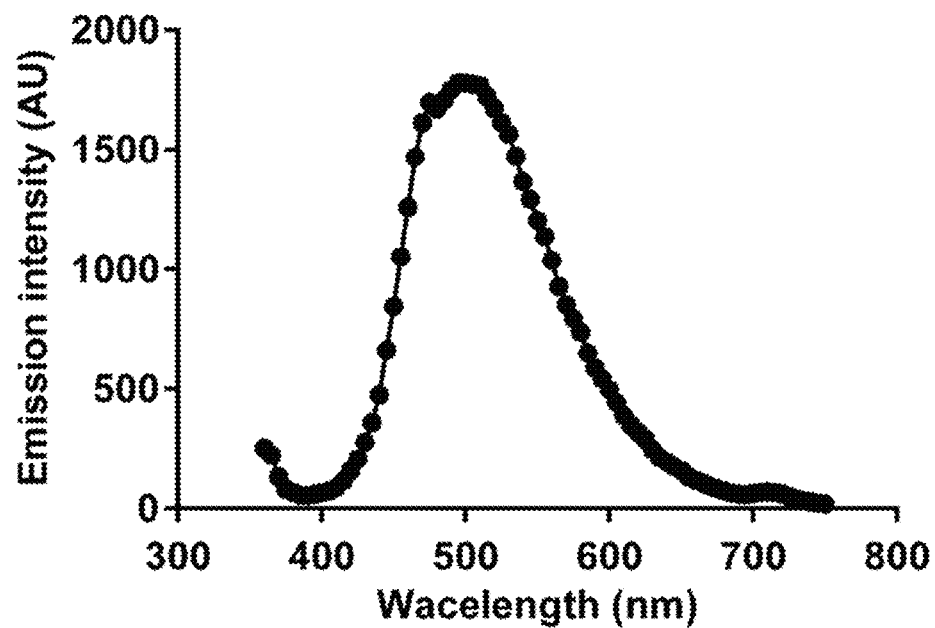
FIG. 15 shows that LPS, upon the reaction with dansyl hydrazine, exhibited an emission maximum at 495 nm in fluorescence spectrophotometric analysis.

Before the conjugation, the purified LPS was activated as follows. An amount of 1 ml of 2 mg/ml of an aqueous LPS solution was vortexed for 3 min and sonicated for 15 min at 25° C. Then, 1 ml of 4.5 mM sodium deoxycholate (NaDC) was added; 100 µl of 2.5 mM EDTA solution was added. The mixture was stirred for 30 minutes at 37° C., sonicated for 15 minutes, and stirred for another 30 minutes at 37° C. 40 µl of 100 mg/ml 1-cyano-4-dimethylaminopyridinium tetrafluoroborate (CDAP) in acetonitrile was added. After 30 seconds, 40 µl of 0.2M aqueous triethylamine (TEA) was added. The mixture was kept at 25° C. for further 150 seconds with stirring to allow activation of LPS by CDAP LPS derived from *Salmonella enterica* sv. Minnesota was reacted with dansyl hydrazine to introduce a hydrazine group for subsequent coupling with amine group on a linker unit. Briefly, 1 ml of 2.0 mg/ml dansyl hydrazine in 0.1 M sodium borate buffer, pH 9.3, was added to the CDAP-activated LPS. The mixture was left to react overnight in the dark at 25° C. under stirring. The reaction was quenched by adding 100 µl of ethanolamine. The unreacted dansyl hydrazine was removed by dialysis against Milli-Q water using a 3,500 MWCO dialysis membrane for 24 hours at 4° C. in the dark. The sample was characterized using fluorescence spectroscopy by measuring the emission spectra under the excitation at 325 nm. FIG. 15 showed that LPS, upon the reaction with dansyl hydrazine, exhibited an emission maximum at 495 nm in fluorescence spectrophotometric analysis.

The identification of the purified LPS and the dansyl-activated LPS was carried out by mass spectrometry MALDI-TOF. The purified LPS had a m.w. of 3143 daltons; the dansyl-activated LPS had a m.w. of 3651 daltons, indicating one LPS conjugated with two dansyl hydrazine molecules; one dansyl hydrazine molecule had a m.w. of 265 daltons.

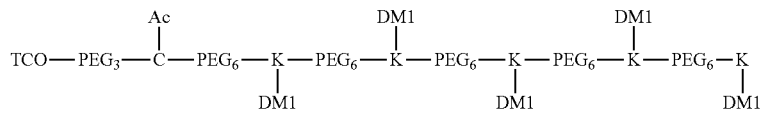

Example 16: Conjugation of LPS Molecules to TCO-Peptide 1

LPS from *Salmonella enterica* sv. Minnesota (Cat No. L2137, Sigma) was chromatographically purified on the The conjugation of LPS molecules to the NH$_2$ groups of the lysine residues of TCO-peptide 1 was performed. Briefly, 0.67 mole of the dansyl-activated LPS was mixed with 0.067 mole of TCO-peptide 1 in 0.1 M sodium bicarbonate buffer, pH 9.5, at room temperature overnight.

The present drug bundle, as illustrated below, was composed of a linker unit with a free TCO functional group and a set of two LPS molecules as effector elements.

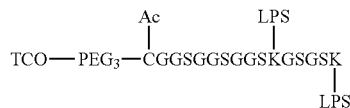

Example 17: Conjugation of a Imiquimod Molecule with NHS-PEG$_6$-Maleimide-Conjugated TCO-Peptide 9

Figure 16:
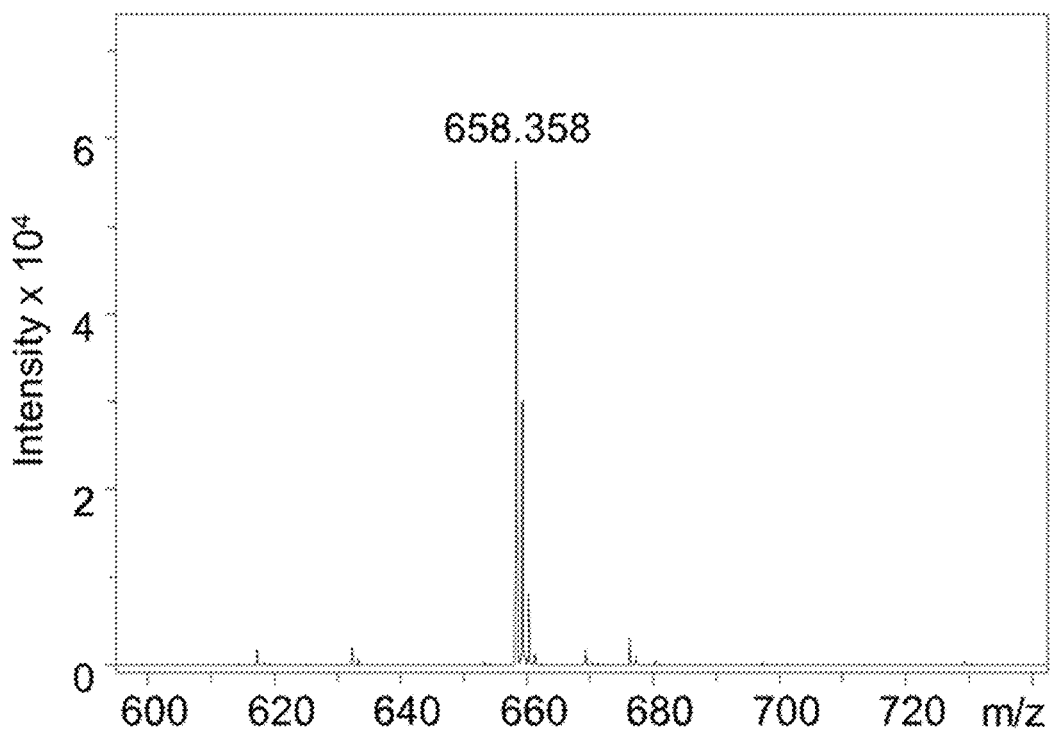
FIG. 16 shows mass spectrometric analysis of $PEG_{5}$-NHS conjugated with imiquimod.

The NH$_2$ group of the imiquimod molecule was reacted with a homo-bifunctional crosslinker, NHS-PEG$_5$-NHS (Conju-probe Inc.) at a 1:3.5 molar ratio. Mass spectrometric analysis showed that PEG$_5$-NHS conjugated with imiquimod had a m.w. of 658.36 daltons (FIG. 16).

The product, imiquimod-PEG$_5$-NHS, was purified by HPLC to remove the excess, unreacted crosslinkers. TCO-peptide 9 and imiquimod-PEG$_5$-NHS were then mixed in 100 mM sodium phosphate buffer at pH 7.5 at 25° C. for 18 hours. Mass spectrometric analysis showed that the drug bundle with imiquimod had a m.w. of 5135 daltons.

The present drug bundle, as illustrated below, was composed of a linker unit with a free TCO functional group and a set of five imiquimod molecules as effector elements.

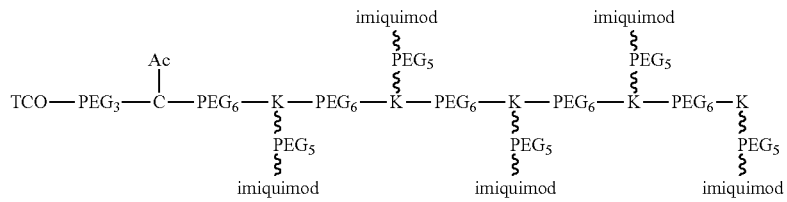

Example 18: Conjugation of DOTA-NHS to TCO-Peptide 9

DOTA-NHS (1,4,7,10-tetraazacyclododecane-1,4,7,10-tetraacetic acid N-hydroxy-succinimide ester) was purchased from Macrocyclics, Inc. Dallas, USA. Conjugation of DOTA-NHS to TCO-peptide 9 employed a two-step procedure as illustrated in Scheme 9. In the first step, TCO-peptide 9 was dissolved in the conjugation buffer (phosphate buffered saline, PBS, with 5 mM EDTA pH 7.0) at 1 mM. The reaction mixtures were incubated for overnight at room temperature. In the second step, the DOTA-NHS ester was added to the incubated solution at 100 mM final concentration (1:100 molar ratio or 1:20 equivalent ratio). Since the DOTA-NHS ester was acidic because of containing TFA, the pH of the solution was adjusted to 8.0 in order to activate the NHS ester-NH$_2$ coupling reaction. The reaction mixtures were incubated overnight at room temperature.

Figure 17A:
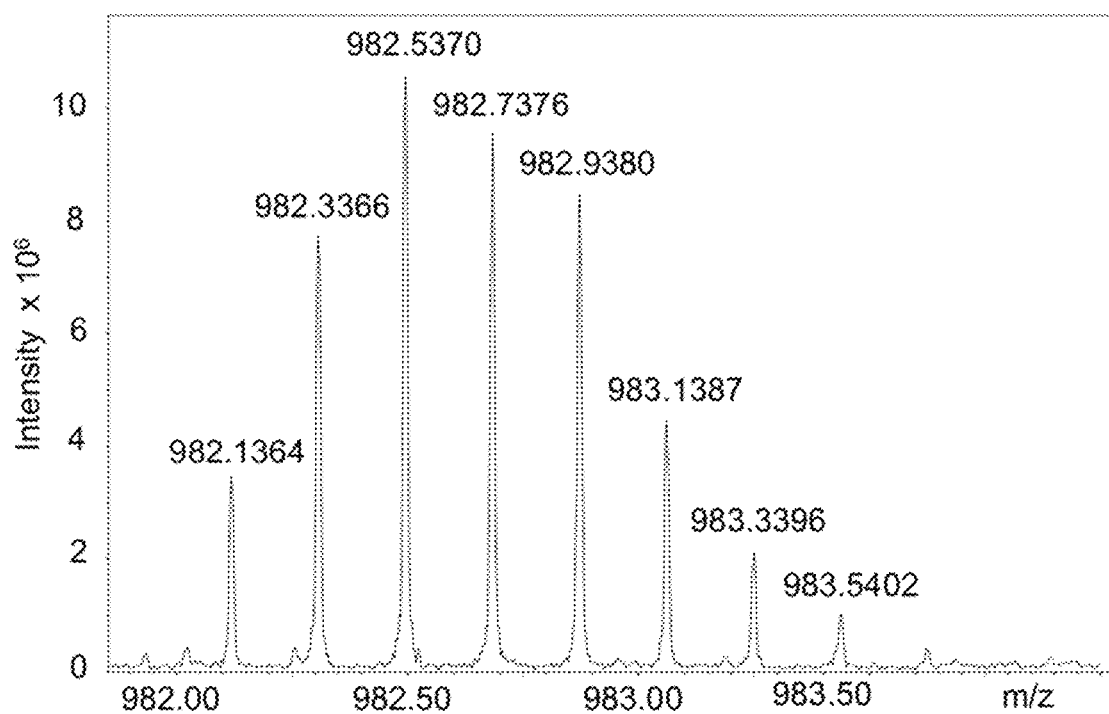
FIG. 17A shows mass spectrometry ESI-TOF result of DOTA-conjugated TCO-peptide 9.

According to the data in FIG. 17A, the present molecular construct had a m.w. of 4907.685; (ESI-TOF) m/z (z=5): [M+3H]$^+$; calculated for C$_{214}$H$_{38}$N$_{39}$O$_{86}$S$_1$ 982.5358. found 982.5370.

<<Scheme 9 Two-step procedure for conjugation of DOTA-NHS to TCO-peptide 9>>

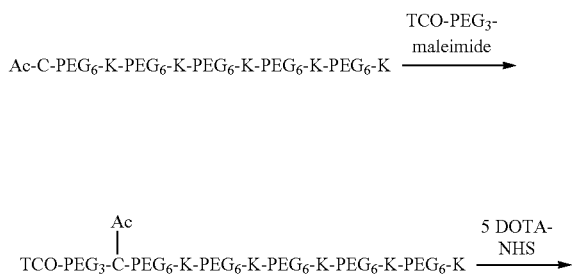

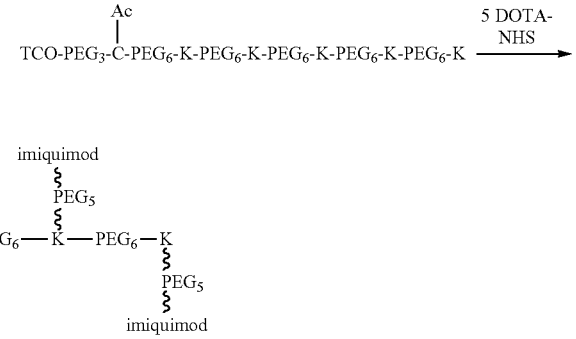

-continued

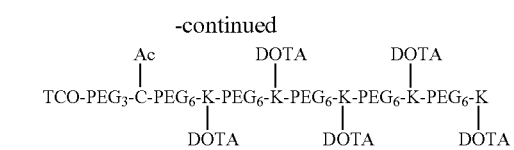

Example 19: Chelation of Yttrium Atoms by DOTA-Conjugated Linker Unit Based on TCO-Peptide 9

Scheme 10 showed the chelation of five Y$^{3+}$ ions by DOTA-conjugated TCO-peptide 9. Herein, Y(NO$_3$)$_3$ solution was added to the reaction mixtures at a 1:100 molar ratio, incubated for 2 hours at room temperature. Free DOTA-NHS and Y$^{3+}$ ions were removed from reaction mixtures by using NAP-10 Sephadex G-25 column.

<<Scheme 10 Chelation of Yttrium atom by DOTA-conjugated TCO-peptide 9>>

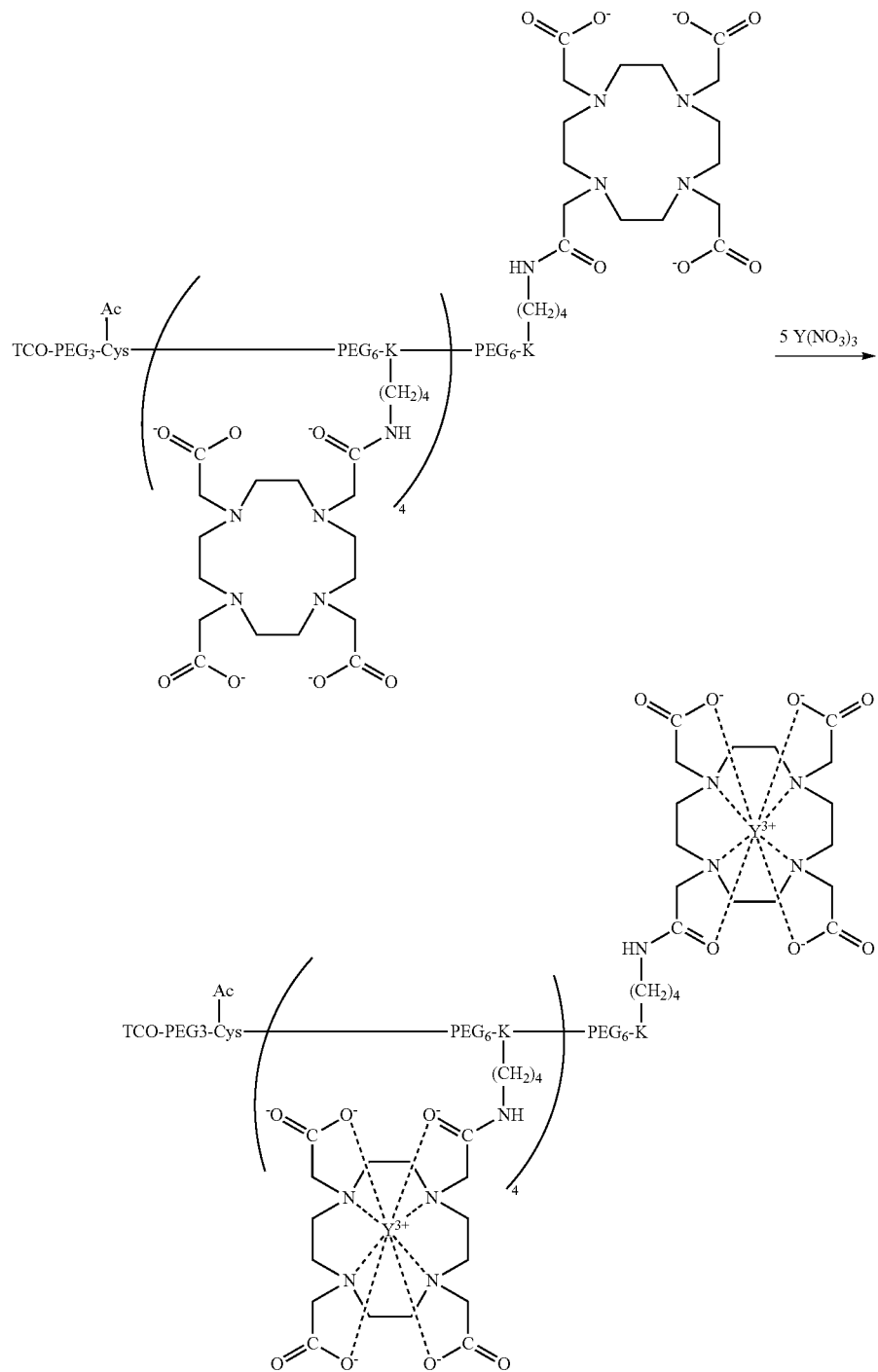

Figure 17B:
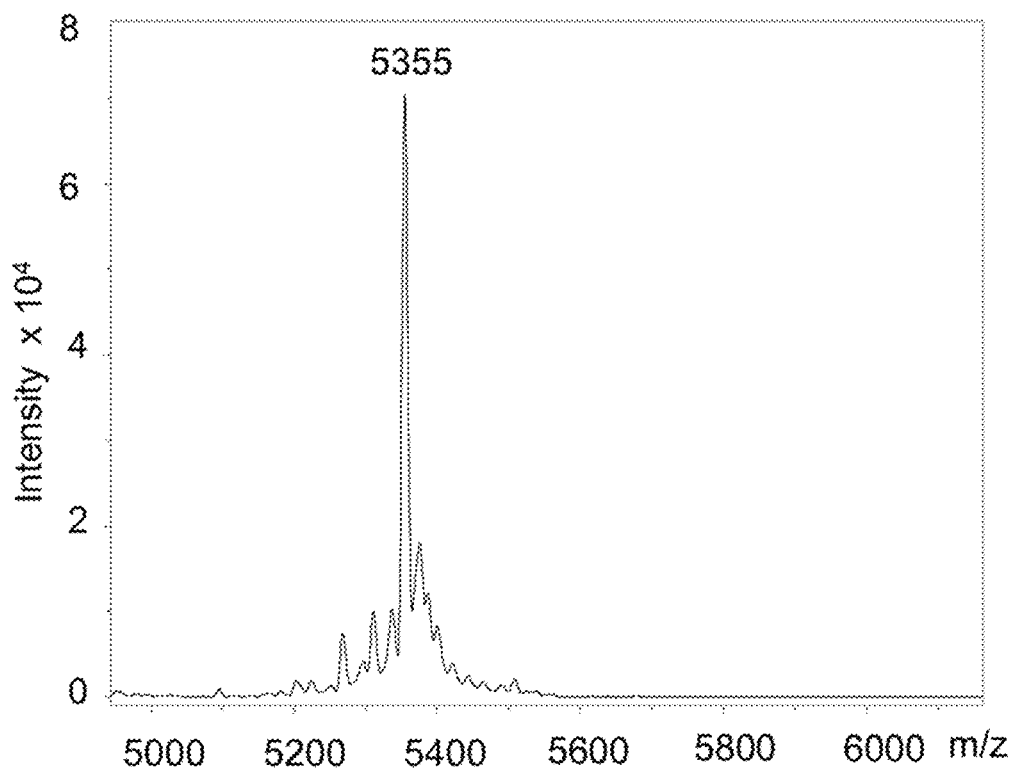
FIG. 17B shows the mass spectrometric result of $Y^{3+}$-chelated, DOTA-conjugated TCO-peptide 9.

DOTA-conjugated TCO-peptide 9 with bound $Y^{3+}$ ions was analyzed by mass spectroscopy MALDI-TOF. Mass spectrometric analysis showed that the sample of DOTA-conjugated TCO-peptide 9 with bound $Y^{3+}$ ions had a m.w. of 5355 daltons (FIG. 17B).

Illustrated below is the present drug bundle, which was composed of a linker unit with a free TCO functional group and a set of five DOTA groups respectively chelating an $Y^{3+}$ ion as effector elements.

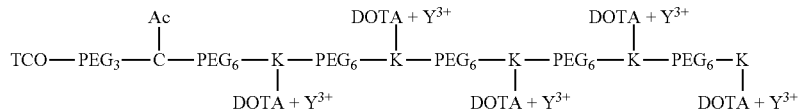

Example 20: Preparation of CCK Analogue

The peptide analogue of CCK (CGGGGSDY(SO$_4$H)L(N)GWL(N)DF-NH$_2$; SEQ ID NO: 27) was designed to be composed of an 8-amino acid segment of CCK with three unusual amino acid residues and a consecutive N-terminal extension of six amino acid residues (CGGGGS) with a cysteine residue at the terminal. The tyrosine residue (Y) was sulfated at its OH group on the aromatic ring and X was a norleucine residue. The cysteine residue provided an SH group for conjugation with PEG-maleimide linking arms of the linker unit according to the present disclosure. The peptide was custom-synthesized by Kelowna Inc., Taipei, Taiwan.

Example 21: Assay of Biological Activity of LPS Upon the Conjugation to Peptide Core Through Linking Arm To test the LPS biological activity of linker unit conjugated with LPS, TLR 4 stimulation cell-based assay was performed using HEK-Blue™ detection kit (InvivoGen, San Diego, USA) according to manufacturer's instruction. HEK-Blue™ hTLR4 cells express two human genes, TLR4 and MD-2/CD14 co-receptor genes, and contain the secreted embryonic alkaline phosphatase (SEAP) reporter gene for monitoring nuclear factor (NF)-κB activation. Upon interaction with the TLR4 agonist, TLR4 transduces a signal to trigger the activation of NF-κB and to express secreted alkaline phosphatase, which can be detected by using detection medium (HEK-Blue™ detection, a medium used for the quantification of secreted alkaline phosphatase; InvivoGen) and measured with a spectrophotometer.

Briefly, HEK-hTLR4 cells were cultured at a density of 2.5×10$^4$ cells in 96-well plates and maintained in complete DMEM with selective antibiotics, normocin. Cells were stimulated with different concentrations (2-fold dilutions from 100 μg/ml) of crude LPS, purified LPS, dansyl hydrazine modified LPS, and the LPS conjugated to peptide core for 18 hours. The activation of TLR4 was analyzed by measuring SEAP from the culture medium using a spectrophotometer at 620 nm.

Figure 18:
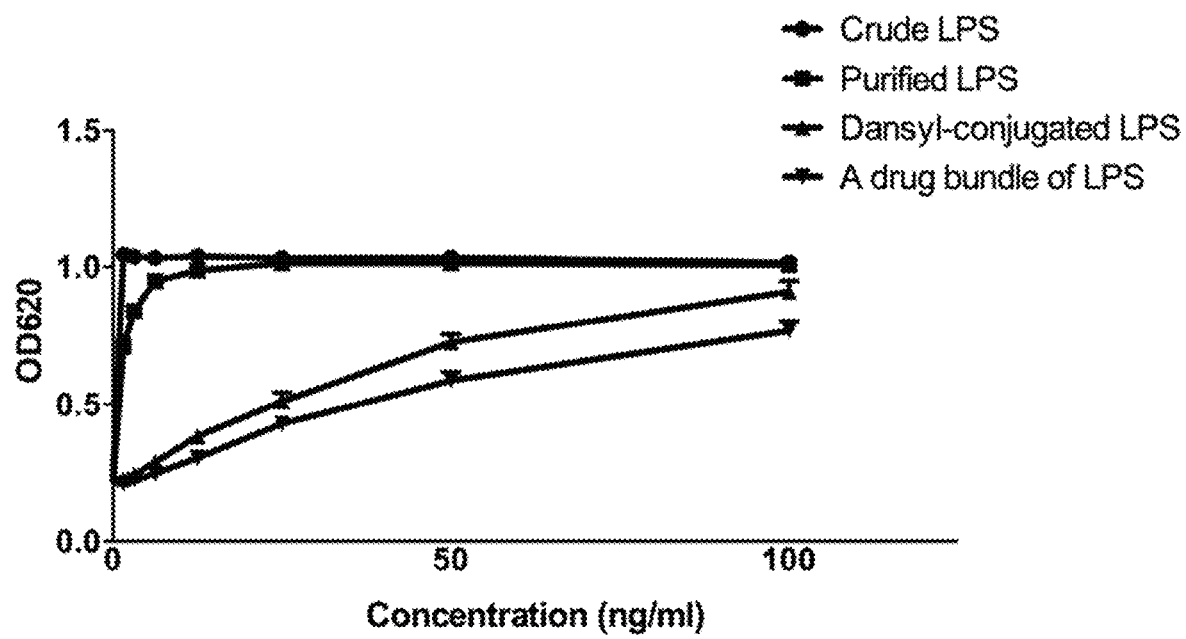
FIG. 18 shows the assay results of the biological activity of LPS, before and after modification with dansyl hydrazine.

FIG. 18 showed the assay results of the biological activity of LPS, before and after modification. The LPS fraction suitable for the modification with dansyl hydrazine was purified, which had a biological activity that was similar to the crude LPS. Dansyl hydrazine-modified LPS and the LPS conjugated to peptide core had comparable partial activities.

Example 22: Assay of Biological Activity Imiquimod Upon the Conjugation to Peptide Core Through Linking Arm To test the biological activity of PEG$_5$-NHS conjugated with imiquimod, TLR 7 stimulation cell-based assay was performed using HEK-Blue™ detection kit (InvivoGen, San Diego, USA) per the manufacturer's instruction. HEK-Blue™ hTLR7 cells express two human genes, TLR7 receptor gene and an secreted embryonic alkaline phosphatase (SEAP) reporter gene. Upon interaction with the TLR7 agonist, TLR7 transduces a signal to trigger the activation of NF-κB and to express secreted alkaline phosphatase, which can be detected by using detection medium (HEK-Blue™ detection, a medium used for the quantification of secreted alkaline phosphatase; InvivoGen) and measured with a spectrophotometer.

Briefly, HEK-hTLR7 cells were cultured at a density of 4×10$^4$ cells in 96-well plates and maintained in complete DMEM with selective antibiotics, normocin. Cells were stimulated with different concentrations (2-fold dilutions from 20 μg/ml) of imiquimod and the PEG$_5$-NHS conjugated with imiquimod for 18 hours. The activation of TLR7 was analyzed by measuring SEAP from the culture medium using a spectrophotometer at 620 nm.

Figure 19:
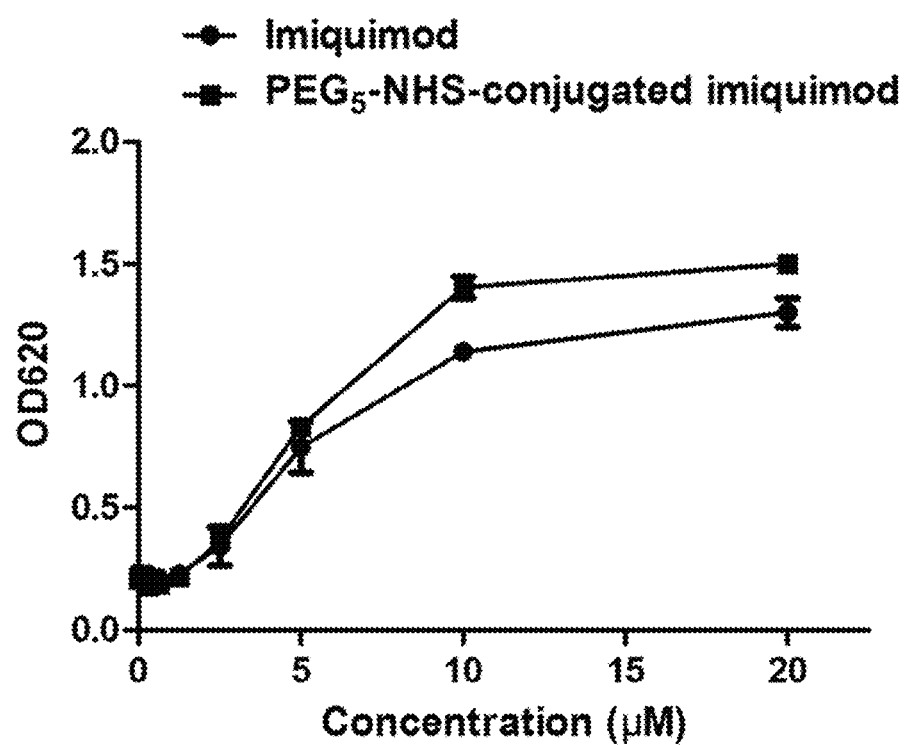
FIG. 19 shows the assay results of the biological activity of imiquimod upon the conjugation with PEG linking arm.

FIG. 19 showed the assay results of the biological activity of imiquimod upon the conjugation with linking arm, indicating that the imiquimod molecule conjugated with a linking arm had similar biological activity as the unmodified imiquimod.

Figure 20A:
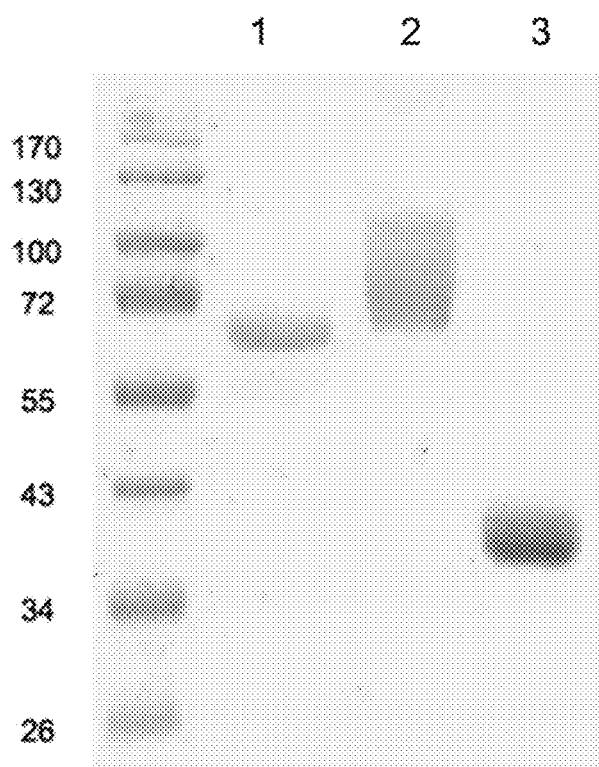
FIG. 20A shows the SDS-PAGE analysis of the 2-chain EGF-CH2-CH3 with a C-terminal extension and a cysteine residue and a 2-chain EGF-CH2-CH3-scFv of anti-PD1.

Example 23: Preparation of 2-Chain IgG1.Fc Fusion Protein Molecular Construct Containing EGF as Targeting Element and Bundles of Cytotoxic Molecules as Effector Elements The configuration illustrated below showed that 2-chain IgG1.Fc fusion protein was prepared by configuring EGF-CH2-CH3 (human γ1) in a recombinant chain. The C-terminal of the 53 a.a. EGF was linked to the N-terminal of CH2 via a linker, ASGGGGSGGGGS. The C-terminal of the CH3 was extended with GGGDC. The cysteine residue at the C-terminal was for coupling with the linker unit carrying a bundle of cytotoxic payload. The sequence of the recombinant peptide chain is shown in SEQ ID NO: 28. The purification of recombinant proteins were performed at 4° C. by protein A chromatography, and the purity of proteins was analyzed through Coomassie staining of 12% SDS-PAGE. FIG. 20A showed the SDS-PAGE analysis of the 2-chain EGF-CH2-CH3 with a C-terminal extension and a cysteine residue and a 2-chain EGF-CH2-CH3-scFv of anti-PD1, indicating EGF-CH2-CH3 with a C-terminal extension had a size of about 38 kDa and EGF-CH2-CH3-(scFv of anti-PD1) had a size of about 60-65 kDa, consistent with the expected sizes.

Illustrated below is the configuration of the present 2-chain EGF-hIgG1.Fc with a C-terminal extension and a cysteine residue.

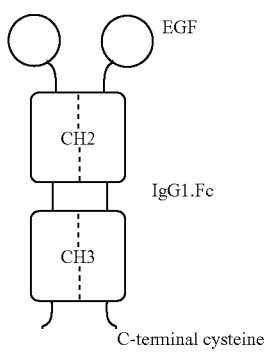

Example 24: The Coupling of a 2-Chain EGF-CH2-CH3 Fusion Protein with Two Drug Bundles of LPS Molecules Via SPACC Reaction The conjugation of tetrazine-PEG$_4$-Mal to the C-terminal cysteine residue of 2-chain EGF-CH2-CH3 was performed. An aliquot of 0.6 mole of the linker unit conjugated with LPS was mixed with 0.06 mole of 2-chain EGF-IgG1.Fc fusion protein in 0.1 M sodium phosphate buffer, pH 7.0, at room temperature overnight at 10:1 molar ratio ([linker]:[protein]). The SH group of the terminal cysteine was conjugated with maleimide-PEG$_4$-tetrazine. Mass MALDI-TOF analysis was performed for the identification of the formation of tetrazine-conjugated 2-chain IgG1.Fc fusion protein via SH-maleimide reaction. A mass spectrometric analysis showed that the tetrazine-conjugated 2-chain IgG1.Fc fusion protein had a m. w. of 68852.

The conjugation of a drug bundle (linker unit) with a free TCO group and 2 LPS molecules to the free tetrazine group of the 2-chain EGF-CH2-CH3 was further performed. An amount of 100 µl of 1 mg/ml of the drug bundle was added to the solution containing tetrazine-conjugated 2-chain EGF-CH2-CH3 at a molar ratio of 2:1 ([tetrazine]:[TCO]). The reaction mixtures were incubated for 16 hours at room temperature.

Figure 20B:
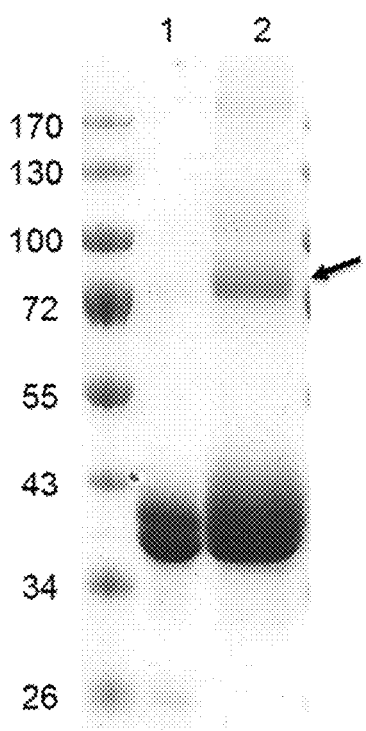
FIG. 20B shows SDS-PAGE analysis of 2-chain IgG1.Fc fusion protein conjugated with a linker unit with 2 LPS molecules.

FIG. 20B showed SDS-PAGE analysis of 2-chain IgG1.Fc fusion protein conjugated with a linker unit with two LPS molecules. The band in lane 1 was EGF-CH2-CH3 with a C-terminal linker and cysteine residue, and the arrow in lane 2 was EGF-CH2-CH3 conjugated with a drug bundle with two LPS molecules.

Illustrated below is 2-chain IgG1.Fc fusion protein conjugated with a linker unit with LPS.

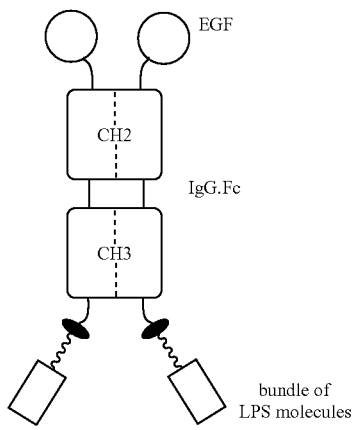

Example 25: Preparation of 2-Chain IgG1.Fc Fusion Molecular Constructs Containing EGF as Targeting Element and scFv Specific for PD1 as Effector Element The configuration illustrated below showed the configuration of 2-chain IgG1.Fc fusion protein molecular construct containing EGF as targeting element and scFv specific for PD-1 as effector element.

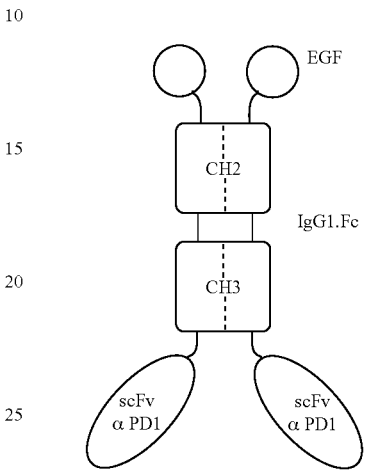

The 2-chain IgG1.Fc fusion protein, 2-chain EGF-hIgG1.Fc-(scFv α PD1) (SEQ ID NO: 29), was prepared by configuring EGF-CH2-CH3-(scFv α PD1) (human γ1) in a recombinant chain. The CH2-CH3 was part of human γ1 and the scFv was specific for human PD1. The V$_L$ and V$_H$ of the scFv specific for PD1 were those of V$_L$ and V$_H$ of nivolumab. The C-terminal of CH3 was connected with the anti-PD1 scFv with a flexible linker, (GGGGS)$_3$. The purification of recombinant proteins were performed at 4° C. by protein A chromatography.

Figure 21A:
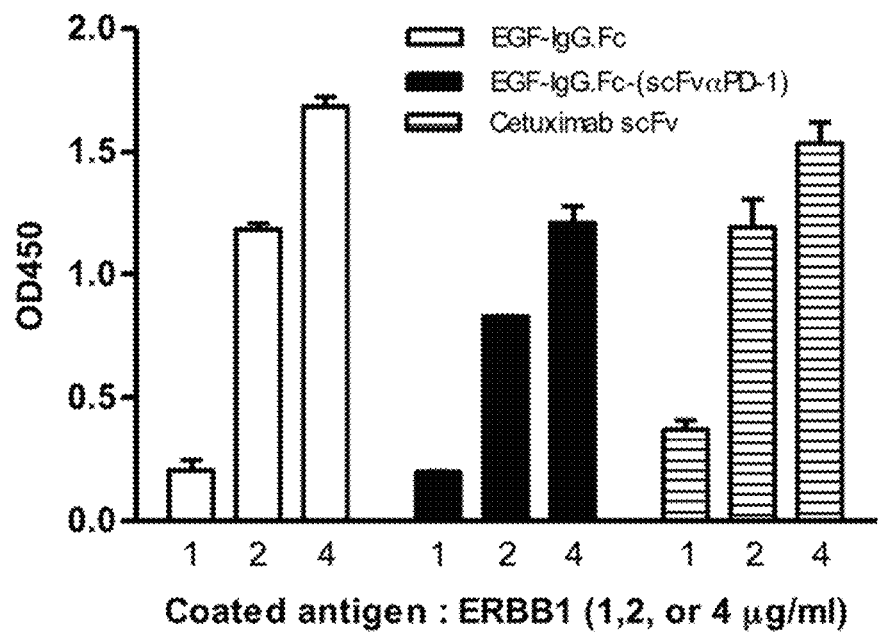
FIGS. 21A and 21B show the ELISA results examining EGF-IgG1.Fc-(scFv α PD1) in binding to various PD-1 and ERBB!.

To examine the binding ability of the recombinant 2-chain EGF-IgG1.Fc-(scFv α PD1) fusion protein to ERBB1, ELISA analysis was performed on the recombinant 2-chain EGF-IgG1.Fc fusion protein and EGF-IgG1 Fc-(scFv α PD1) fusion protein. ELISA plates were coated with 1 µg/mL, 2 µg/mL, and 4 µg/mL of recombinant ERBB1 protein. Cetuximab was a human IgG1 antibody against human EGFR, and cetuximab scFv was used as a positive control. ELISA results summarized in FIG. 21A showed that both EGF-IgG1.Fc fusion protein and EGF-IgG1.Fc-(scFv α PD1) fusion protein bound to ERBB1 ecto domain, and had a comparable binding ability with Cetuximab scFv. Each bar represented the mean OD450 value of duplicate samples.

Figure 21B:
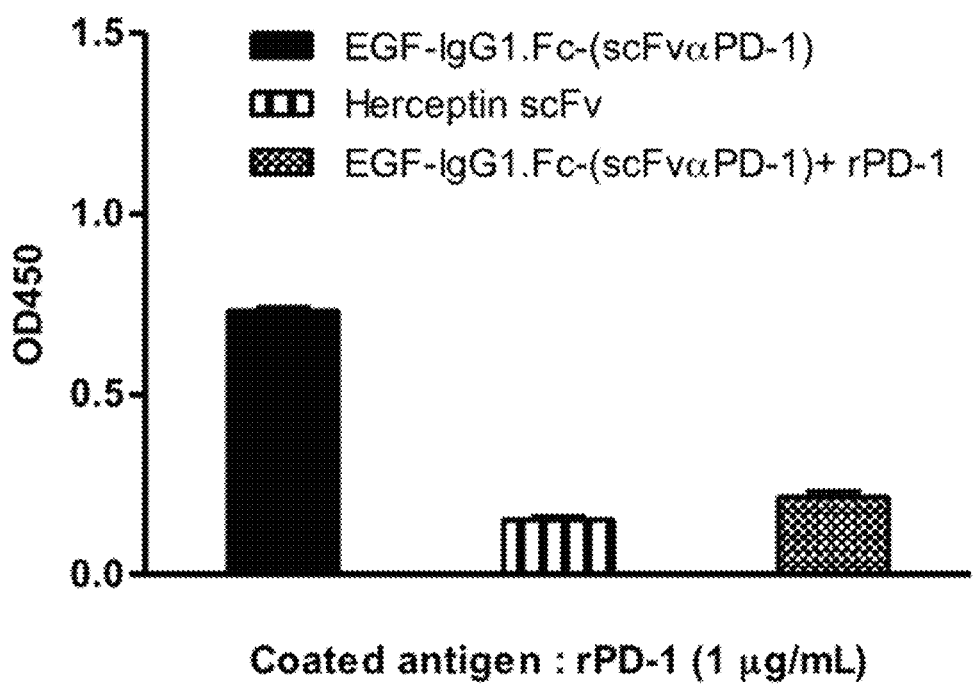

To examine the binding ability of recombinant 2-chain EGF-IgG1.Fc-(scFv α PD1) fusion protein to PD-1, ELISA plates were coated with 1 µg/mL of recombinant human PD-1 protein. Herceptin was a human IgG1 antibody against ERBB2, and Herceptin scFv was used as a negative control. Each bar represented the mean OD450 value of duplicate samples. ELISA results in FIG. 21B showed the positive binding of EGF-IgG1.Fc-(scFv α PD1) fusion protein to human PD-1 protein.

Figure 22A:
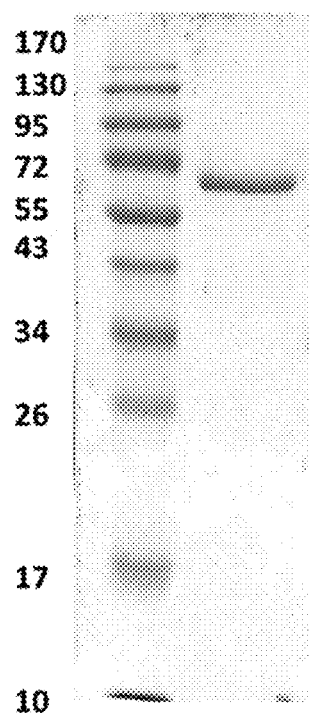
FIG. 22A shows the SDS-PAGE analysis of the 2-chain EGF-hIgG1.Fc-(scFv α CD3) molecular construct.

Example 26: Preparation of 2-Chain IgG1.Fc Fusion Molecular Constructs Containing EGF as Targeting Element and scFv Specific for CD3 as Effector Element In this example, the 2-chain IgG.Fc fusion protein was prepared by configuring EGF-CH2-CH3-(scFv α CD3) in a recombinant chain (SEQ ID NO: 30). The CH2-CH3 was part of human γ1 and the scFv was specific for human CD3. The $V_L$ and $V_H$ of the scFv specific for CD3 were those of $V_L$ and $V_H$ of teplizumab. The C-terminal of CH3 was connected with the anti-CD3 scFvs with a flexible linker, (GGGGS)$_3$. FIG. 22A showed the SDS-PAGE analysis of the 2-chain EGF-hIgG1.Fc-(scFv α CD3) molecular construct (illustrated in preceding Examples).

Figure 22B:
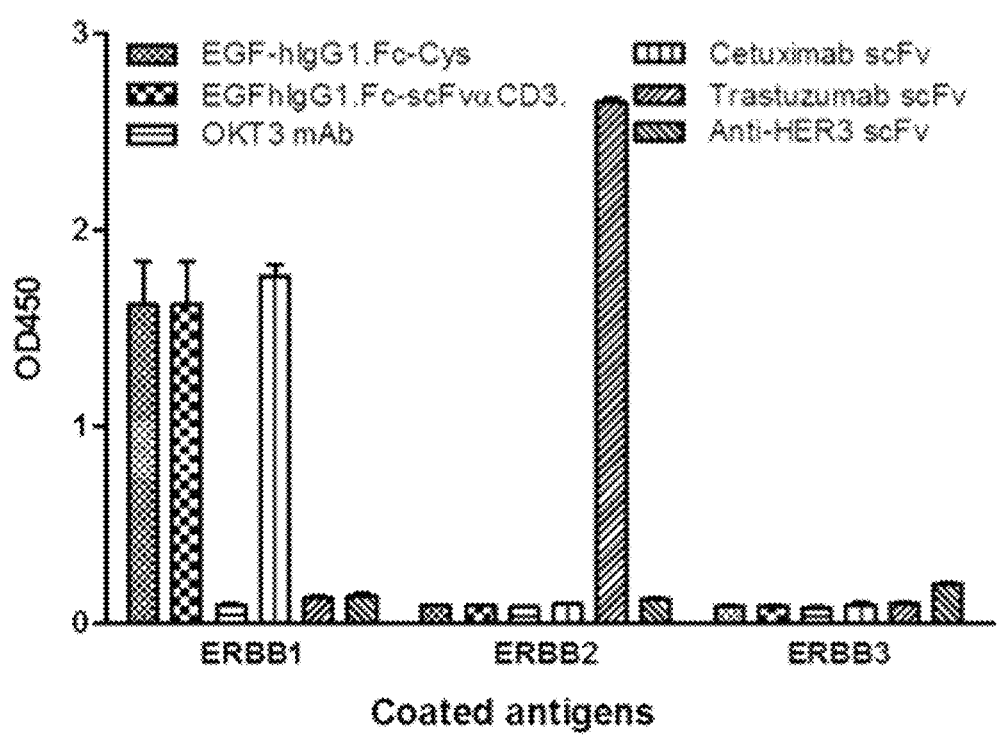
FIG. 22B shows the ELISA analysis examining 2-chain EGF-hIgG1.Fc-(scFv α CD3) in binding to ERBB!, ERBB2, and ERBB3.

To examine the binding ability of recombinant 2-chain EGF-hIgG1.Fc-(scFv α CD3) fusion protein to ERBB1, ERBB2 and ERBB3, ELISA analysis was performed. ELISA plates were coated with 1 μg/mL, 2 μg/mL and 4 μg/mL of recombinant ERBB1, ERBB2, or ERBB3 protein. ELISA results, as summarized in FIG. 22B, showed that the EGF-IgG1.Fc fusion protein and EGF-IgG1.Fc-(scFv α CD3) fusion protein bound to ERBB1 ecto domain, and had a comparable binding ability with Cetuximab scFv. Each bar represents the mean OD450 value of duplicate samples.

Illustrated below is the configuration of the present 2-chain EGF-hIgG1.Fc-(scFv α CD3).

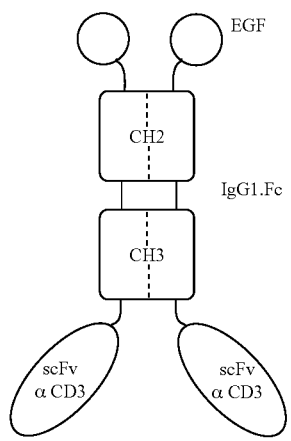

Example 27: Preparation of 2-Chain EGF(S2W/D3V)-IgG1.Fc, EGF(S2W/D3V)-IgG1.Fc-(scFv α PD1) and EGF(S2W/D3V)-IgG1.Fc-(scFv α CD3) Containing EGF Mutant, EGF(S2W/D3V) as Targeting Element It has been shown that replacement of only two amino acids in the linear N-terminal region of EGF (Ser-2 to Trp and Asp-3 to Val) was sufficient to make EGF binding for ERBB2/ERBB3 heterodimer and ERBB3 homodimer. EGF (S2W/D3V) represented the replacement of two amino acids (Ser-2 to Trp and Asp-3 to Val) in the N-terminal region of EGF. The 2-chain EGF(S2W/D3V)-IgG1.Fc, EGF(S2W/D3V)-IgG1.Fc-(scFv α PD1) and EGF(S2W/D3V)-IgG1.Fc-(scFv α CD3) fusion proteins containing EGF mutant EGF(S2W/D3V) were prepared and their binding to ERBB1 homodimer, ERBB2/ERBB3 heterodimer and ERBB3 homodimer was studied.

The sequence of the recombinant 2-chain EGF(S2W/D3V)-IgG1.Fc is shown in SEQ ID NO: 31. The C-terminal of CH3 of EGF(S2W/D3V)-IgG1.Fc-(scFv α PD1) (SEQ ID NO: 32) and EGF(S2W/D3V)-IgG1.Fc-(scFv α CD3) (SEQ ID NO: 33) were connected with anti-PD-1 and anti-CD3 scFv with a flexible linker, (GGGGS)$_3$, respectively.

Illustrated below is the configuration of the present 2-chain EGF(S2W/D3V)-hIgG1.Fc-(scFv α PD-1).

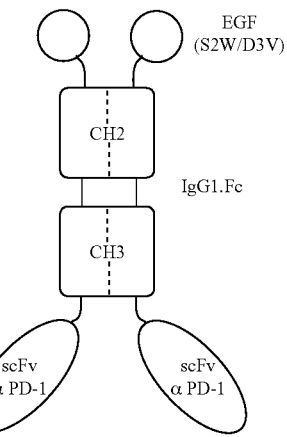

Illustrated below is the configuration of the present 2-chain EGF(S2W/D3V)-hIgG1.Fc-(scFv α CD3).

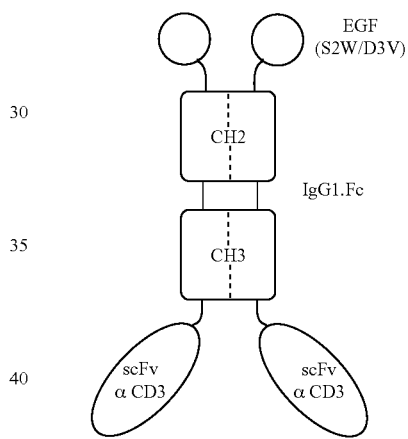

Figure 23A:
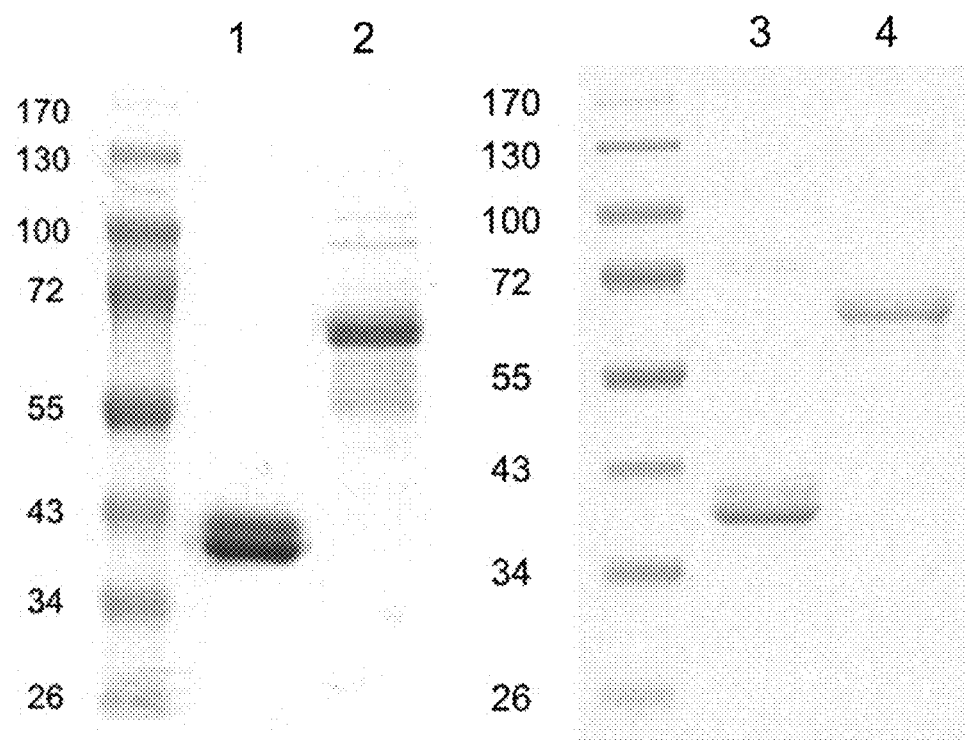
FIG. 23A shows SDS-PAGE analysis of EGF(S2W/D3V)-IgG1.Fc with C-terminal extension, EGF(S2W/D3V)-IgG1.Fc-(scFv α PD1), and EGF(S2W/D3V)-IgG1.Fc-(scFv α CD3).
Figure 23B:
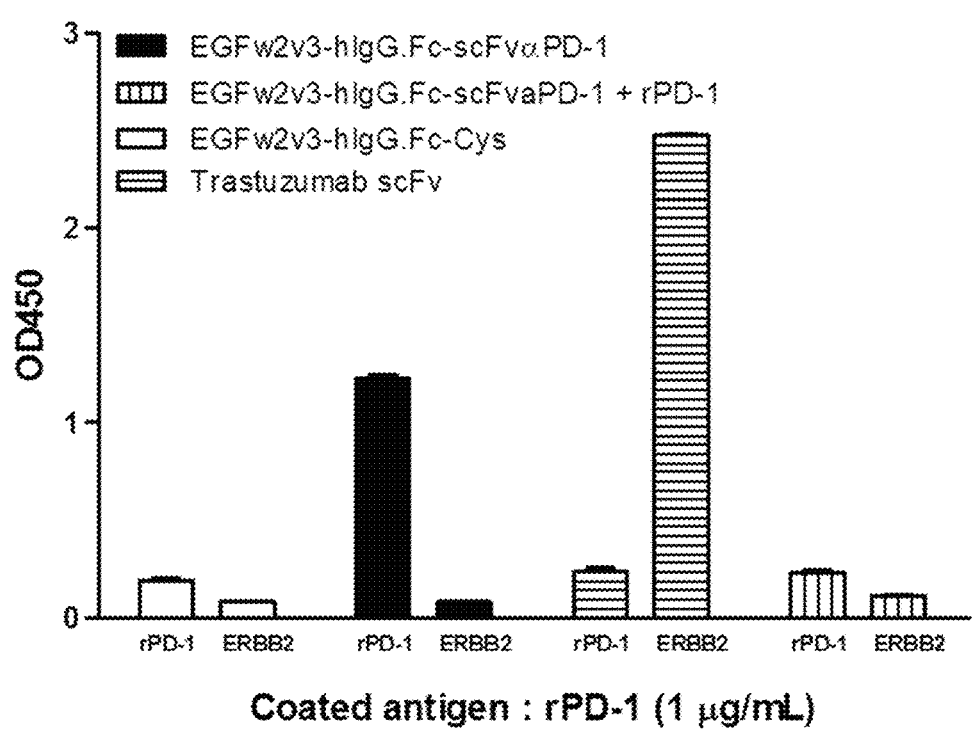
FIG. 23B to 23E show ELISA analyses of EGF(S2W/D3V)-IgG1.Fc-(scFv α PD1). and EGF(S2W/D3V)-IgG1.Fc-(scFv α CD3) in binding to PD-1 or CD3, and ERBB1, ERBB2, and ERBB3.
Figure 23C:
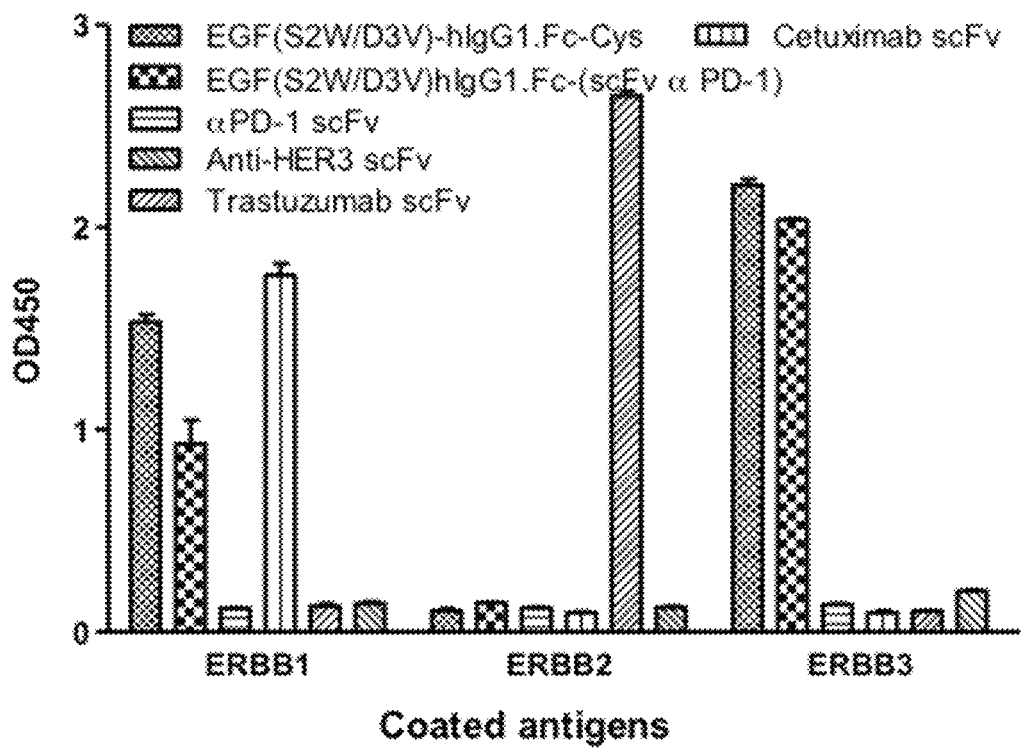
Figure 23D:
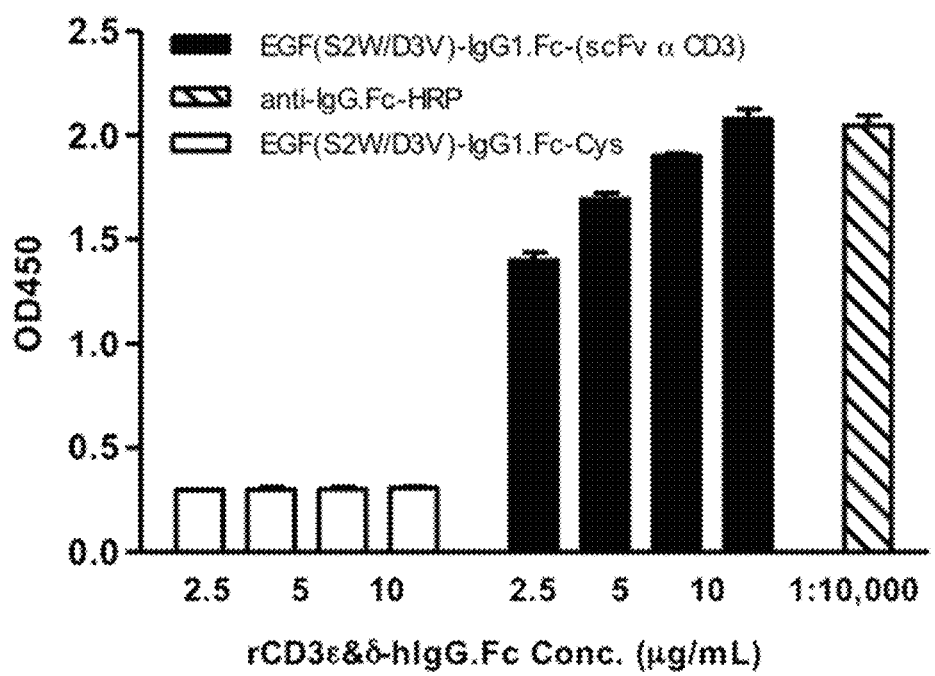
Figure 23E:
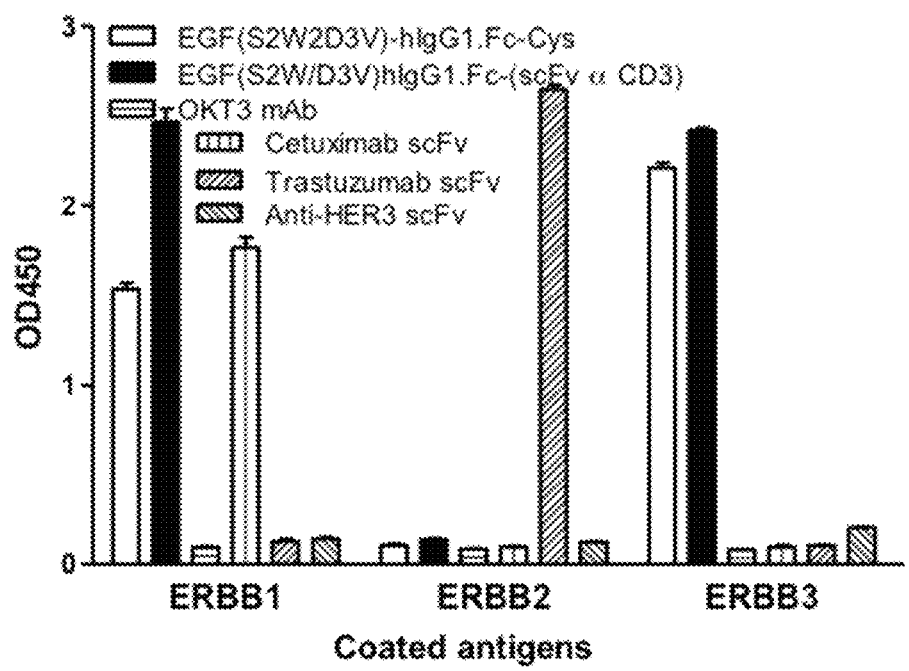

FIG. 23A showed SDS-PAGE analysis of EGF(S2W/D3V)-IgG1.Fc with C-terminal extension (lane 1 and 3), EGF(S2W/D3V)-IgG1.Fc-(scFv α PD1) (lane 2), and EGF (S2W/D3V)-IgG1.Fc-(scFv α CD3) (lane 4). The sizes of the products were consistent with expected sizes. FIGS. 23B and 23C were results of ELISA analyses of EGF(S2W/D3V)-IgG1.Fc-(scFv α PD1), while FIGS. 23D and 23E were results of ELISA analyses of EGF(S2W/D3V)-IgG1.Fc-(scFv α CD3) in binding to recombinant PD-1 or recombinant CD3-Fc fusion protein, and their binding to ERBB1, ERBB2, and ERBB3. The results showed that EGF(S2W/D3V)-IgG1.Fc-(scFv α PD1) could bind to recombinant PD-1, ERBB!, and ERBB3, and that EGF (S2W/D3V)-IgG1.Fc-(scFv α CD3) could bind to recombinant CD3, ERBB1, and ERBB3.

Figure 24:
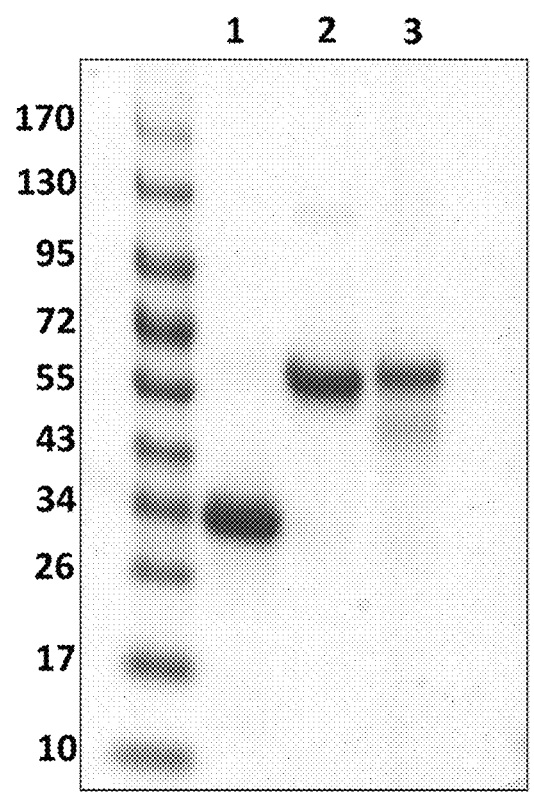
FIG. 24 shows SDS-PAGE analysis of somatostatin-hIgG1.Fc, somatostatin-hIgG1.Fc-(scFv α CD3), and somatostatin-hIgG1.Fc-(scFv α PD-1).

Example 28: Preparation of 2-Chain IgG1.Fc Fusion Protein Molecular Construct Containing Somatostatin as Targeting Element The 2-chain IgG.Fc fusion protein was prepared by configuring somatostatin-CH2-CH3 (human γ1) in a recombinant chain. The C-terminal of the 14 a.a. somatostatin was linked to the N-terminal of CH2 via a linker, ASGGGGSGGGGS. The C-terminal of the CH3 was extended with GGGDC. The cysteine residue at the C-terminal was for coupling with a bundle of drug. The sequence of the recombinant peptide chain containing somatostatin and IgG.Fc is shown in SEQ ID NO: 34. The two molecular constructs with scFv α PD-1 and scFv α CD3 were also prepared. FIG. 24 showed SDS-PAGE (10%) of somatostatin-hIgG1.Fc (lane 1), somatostatin-hIgG1.Fc-(scFv α CD3) (lane 2), and somatostatin-hIgG1.Fc-(scFv α PD-1) (lane 3). The results showed that the sizes of the three constructs were consistent with the expected sizes.

Because of the very small size of somatostatin, SDS-PAGE analysis was not suitable to determine that somatostatin was incorporated into the Fc-fusion protein. Tandem mass spectrometric analysis of trypsin-digested 2-chain somatostatin-hIgG1.Fc-(scFv α PD-1) and 2-chain somatostatin-hIgG1.Fc-(scFv α CD3) was performed for the identification of somatostatin in the molecular constructs. All mass spectrometry experiments were done using a Bruker Autoflex III MALDI TOF/TOF mass spectrometer (Bremen, Germany) equipped with a 200 Hz SmartBean Laser in positive ion mode with delayed extraction in the reflectron mode. Data acquisition was done manually with FlexControl 3.4, and data processing was performed with Flex-Analysis 3.4 (both Bruker Daltonik).

To identify the peptide by molecular mass searching of protein fragment in protein database using Mascot search engine, the m/z value of a protein fragment in MS/MS spectrum, corresponding to 741.37 daltons, was matched to the amino acid sequence of somatostatin fragment (NFFWK). The m/z values of two protein fragments in MS/MS spectrum, corresponding to 835.45 and 1286.69 daltons, were matched to the amino acid sequence of two peptide fragments in the human IgG Fc region, DTLMISR and EPQVYTLPPSR.

Illustrated below is the configuration of the present 2-chain somatostatin-hIgG1.Fc-(scFv α PD-1) (SEQ ID NO: 35).

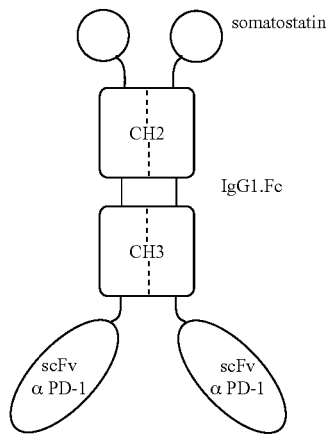

Illustrated below is the configuration of the present 2-chain somatostatin-hIgG1.Fc-(scFv α CD3) (SEQ ID NO: 36).

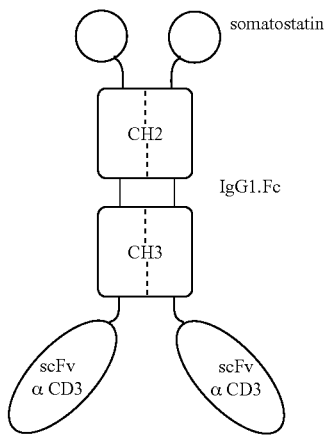

Example 29: Staining Analysis to Examine the Binding of 2-Chain EGF-IgG1.Fc, 2-Chain EGF-IgG1.Fc-(scFv α PD1), 2-Chain EGF-IgG1.Fc-(scFv α CD3), 2-Chain EGF(S2W/D3V)-IgG1.Fc-(scFv α PD1) and 2-Chain EGF(S2W/D3V)-IgG1.Fc-(scFv α CD3) Fusion Proteins to EGFR-Expressing Tumor Cell Line Five molecular constructs were analyzed for their ability to bind to EGFR on tumor cell line A431. A431 was a human epidermoid carcinoma cell line, expressing high levels of EGFR. The assay was performed by incubating 1×10$^5$ EGFR-expressing A431 cells with 10 μg/ml of each construct in PBS, 1% BSA on ice for 30 min, using Cetuximab scFv-FITC as a positive control. Cells were washed and incubated with FITC-conjugated goat anti-human IgG.Fc (Caltag, Buckingham, UK), diluted 1:200 in PBS/BSA, at 4° C. for 20 minutes in the dark. The a20, a mouse monoclonal antibody specific for a membrane-anchoring segment of human membrane-bound IgE, and OKT3, a mouse monoclonal antibody specific for human CD3, were used as negative controls. The staining of cells was analyzed by FACS (FACSCanto II; BD Biosciences) using FITC-conjugated rabbit anti-mouse IgG or goat anti-human IgG.Fc.

Figure 25:
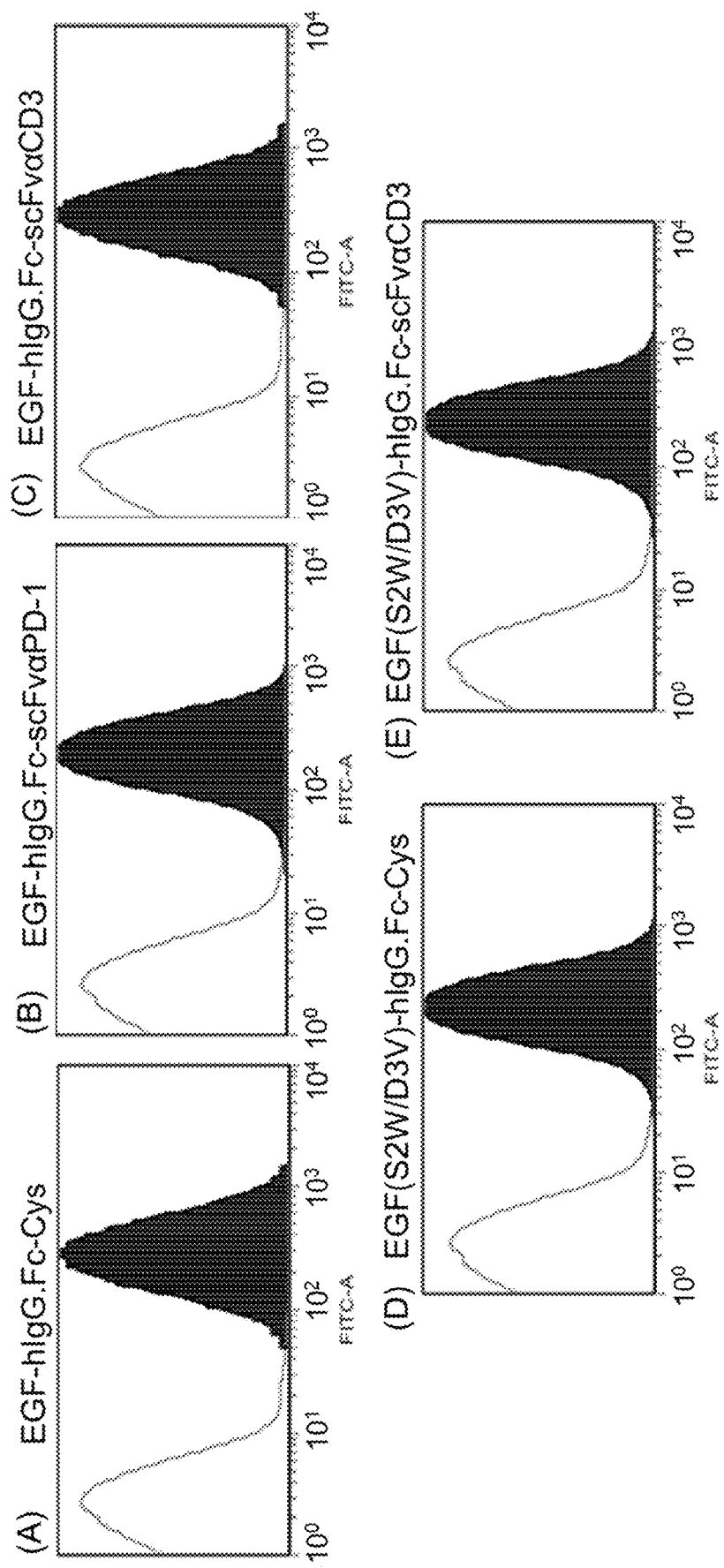
FIG. 25 shows the cell staining analysis of EGF-IgG1.Fc, EGF-IgG1.Fc-(scFv α PD1), EGF-IgG1.Fc-(scFv α CD3), EGF(S2W/D3V)-IgG1.Fc, and EGF(S2W/D3V)-IgG1.Fc-(scFv α CD3) on EGFR-expressing A431 cells.

FIG. 25 showed results of the cell staining analysis of EGF-IgG1.Fc, EGF-IgG1.Fc-(scFv α PD1), EGF-IgG1.Fc-(scFv α CD3), EGF(S2W/D3V)-IgG1.Fc, and EGF(S2W/D3V)-IgG1.Fc-(scFv α CD3) on EGFR-expressing A431 cells. All those five constructs bound to A431 cells positively in a substantial level.

Figure 26:
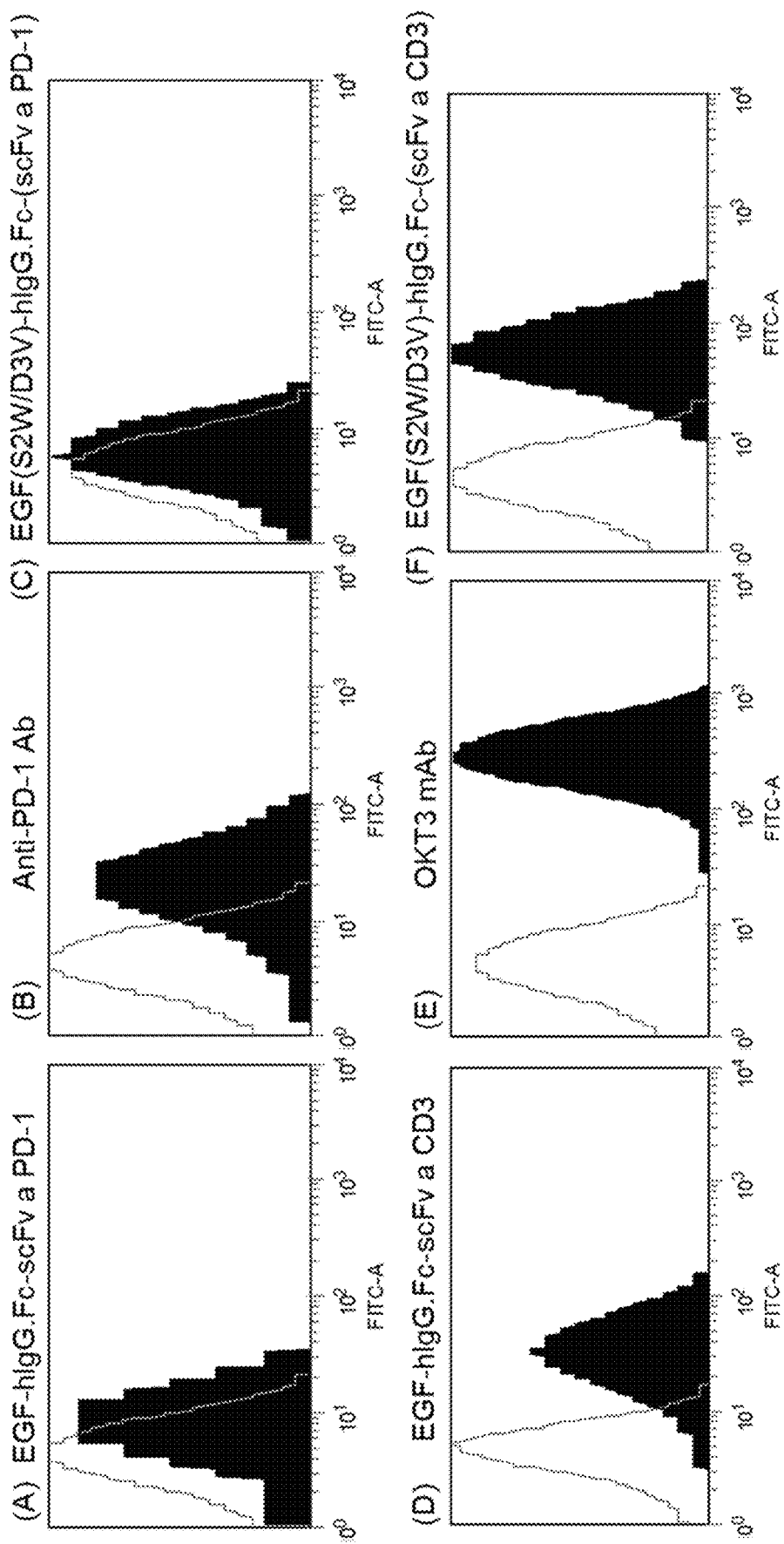
FIG. 26 shows the staining analysis of EGF-IgG1.Fc-(scFv α PD1) and EGF(S2W/D3V)-IgG1.Fc-(scFv α PD1) on T cells in comparison with anti-PD-1 mAb (panels A to C), as well as the staining analysis of EGF-IgG1.Fc-(scFv α CD3) and EGF(S2W/D3V)-IgG1.Fc-(scFv α CD3) on T cells in comparison with anti-CD3 mAb (panels D to F).

Example 30: Staining Analysis Showing Binding of 2-Chain EGF-IgG1.Fc, 2-Chain EGF-IgG1.Fc-(scFv α PD1), 2-Chain EGF-IgG1.Fc-(scFv α CD3), 2-Chain EGF(S2W/D3V)-IgG1.Fc-(scFv α PD1) and 2-Chain EGF(S2W/D3V)-IgG1.Fc-(scFv α CD3) to Human T-Lymphocytes The ability of the various EGF-IgG.Fc-scFv constructs to bind to human T lymphocytes expressing CD3 and PD-1 was studied with fractionated human peripheral blood T lymphocytes. Peripheral blood mononuclear cells (PBMCs) were isolated from buffy coats from healthy donors (Taiwan Blood Service Foundation) by centrifugation over a Ficoll-Paque PLUS (GE Healthcare) density gradient and cryopreserved in 90% FBS/10% DMSO. Human T cells were prepared from PBMCs by depletion of non-T cells (negative selection) using the human Pan T cell Isolation kit (Miltenyl Biotech, Auburn, Calif., USA). 10 µg/ml of EGF-IgG1.Fc and EGF-IgG1.Fc-(scFv α PD1), EGF-IgG1.Fc-(scFv α CD3), EGF(S2W/D3V)-IgG1.Fc-(scFv α PD1) and EGF (S2W/D3V)-IgG1.Fc-(scFv α CD3) were incubated with $1 \times 10^5$ T cells in PBS, 1% BSA on ice for 20 minutes. Anti-PD-1 and OKT3 were used as positive controls and EGF-IgG1.Fc and EGF(S2W/D3V)-IgG1.Fc as negative controls. Cells were washed and incubated with FITC-conjugated goat anti-human IgG.Fc (Caltag) or rabbit anti-mouse IgG.Fc (AbD Serotec), diluted 1:200 in PBS/BSA, at 4° C. for 20 minutes in the dark. Samples were analyzed by FACS analysis (FACSCanto II; BD Biosciences). FIG. 26, panels A to C, showed that EGF-IgG1.Fc-(scFv α PD1) and EGF(S2W/D3V)-IgG1.Fc-(scFv α PD1) bound to T cells as anti-PD-1 antibody did. FIG. 26, panels D to F showed that EGF-IgG1.Fc-(scFv α CD3) and EGF(S2W/D3V)-IgG1.Fc-(scFv α CD3) also bound to T cells as OKT3 antibody.

Example 31: T Cell-Mediated Cytotoxicity Assay of 2-Chain EGF(S2W/D3V)-IgG1.Fc-(scFv α CD3) on MDA-MB-231 and A431 Tumor Cell Lines Human peripheral blood T cells were used as the source of T cells. The T cells were prepared as in the preceding example. T cells were cultured in the presence of 10 p/ml of recombinant human IL-2 (PeproTech, Rocky Hill, USA). Anti-DNP ANO2 mAb was used as an isotype-matched control.

Aliquots of 5,000 A431 target cells in 100 µl complete RPMI medium were coated with recombinant EGF-hIgG.Fc-Cys, EGF-hIgG.Fc-scFv α CD3, EGF(S2W/D3V)-IgG1.Fc-(scFv α CD3), or isotype-matched controls for 30 minutes at 37° C. in a 5% $CO_2$ atmosphere, and then combined with human T cells at different E:T ratios of 20, 10 or 5. After 24 hours of incubation, the cytotoxicity was assayed by a luminescent method using the aCella-Tox kit (Cell Technology, Mountain View, Calif.) according to the manufacturer's instructions. The plate was read by a luminometer (multi-detection microplate reader, DS Pharma, Osaka, Japan).

T cell mediated cytolysis of EGFR-expressing tumor cells by EGF(S2W/D3V)-hIgG1.Fc-scFv α CD3 was studied using MDA-MB-231 tumor cells and A431 tumor cells. MDA-MB-231 was originally derived from a primary invasive ductal carcinoma with pleural effusive metastasis and broadly used in tumor model studies. For this cytotoxicity effects, the source of T cells was important. Isolated human T lymphocytes from donor #56 and #59 were selected to examine the T-cell mediated cytotoxicity. MDA-MB-231 cells were incubated with 10 µg/mL of EGF(S2W/D3V)-hIgG1.Fc or EGF(S2W/D3V)-hIgG1.Fc-scFv α CD3 at 37° C. for 1 hour, and then mixed with human T lymphocytes at different E:T ratios of, 20, 10 or 5, and incubated for 24 hours. Cetuximab mAb was used as a control. Cytolysis was analyzed by using an aCella-Tox kit. The data shown here indicated that scFv α CD3-carrying EGF(S2W/D3V)-hIgG1.Fc recruited effector cells more efficiently to manifest the cytolytic activity.

Figure 27A:
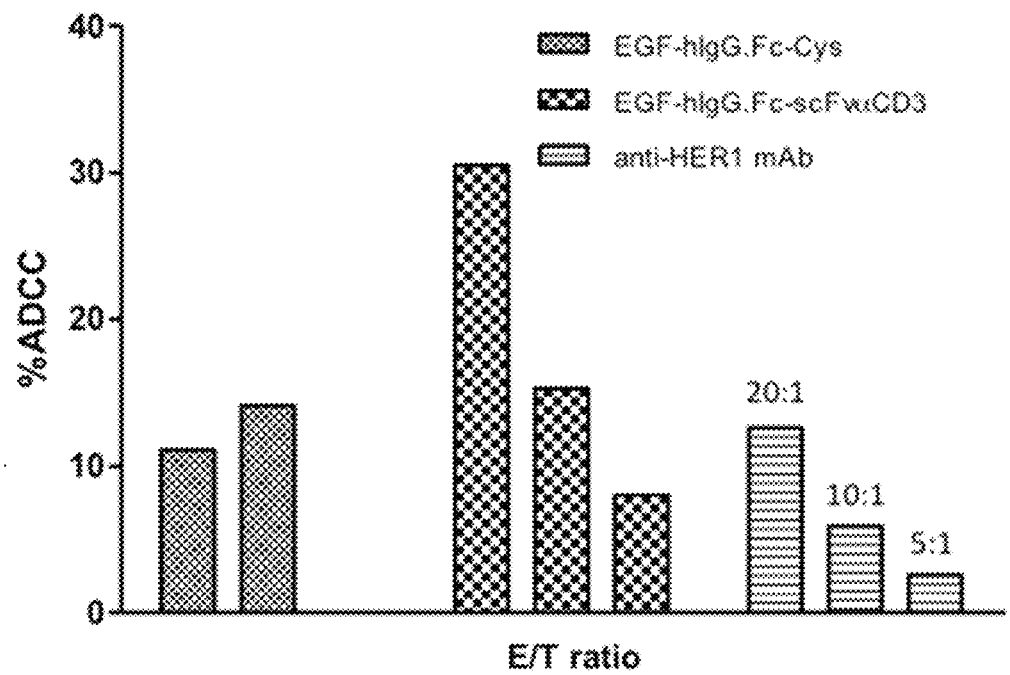
FIGS. 27A and 27B show the T cell-mediated cytolysis of EGFR-expressing of A431 cells upon the incubation with EGF-hIgG.Fc-scFv α CD3 and EGF(S2W/D3V)-IgG1.Fc-(scFv α CD3).
Figure 27B:
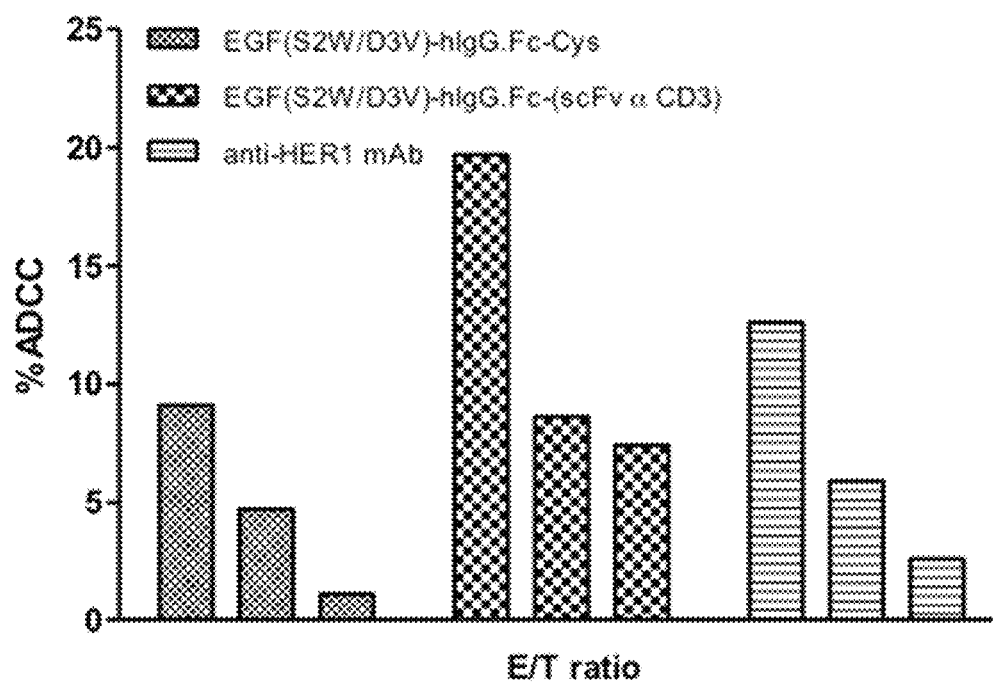
Figure 27C:
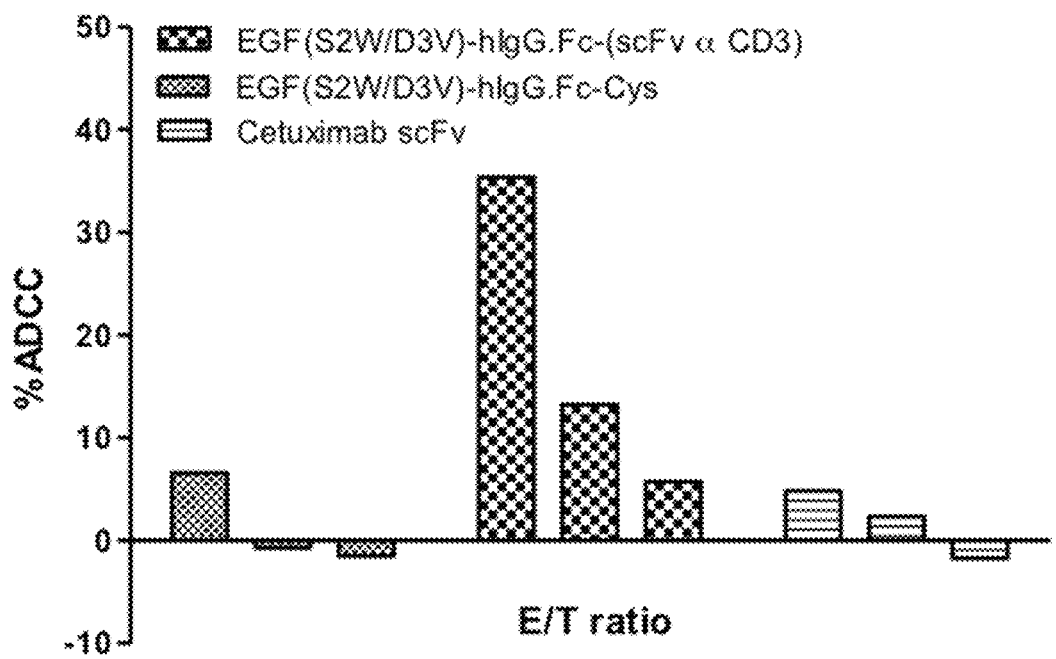
FIGS. 27C and 27D show the degree of cytolysis on MDA-MB-231 cells upon the incubation with EGF(S2W/D3V)-IgG1.Fc-(scFv α CD3).
Figure 27D:
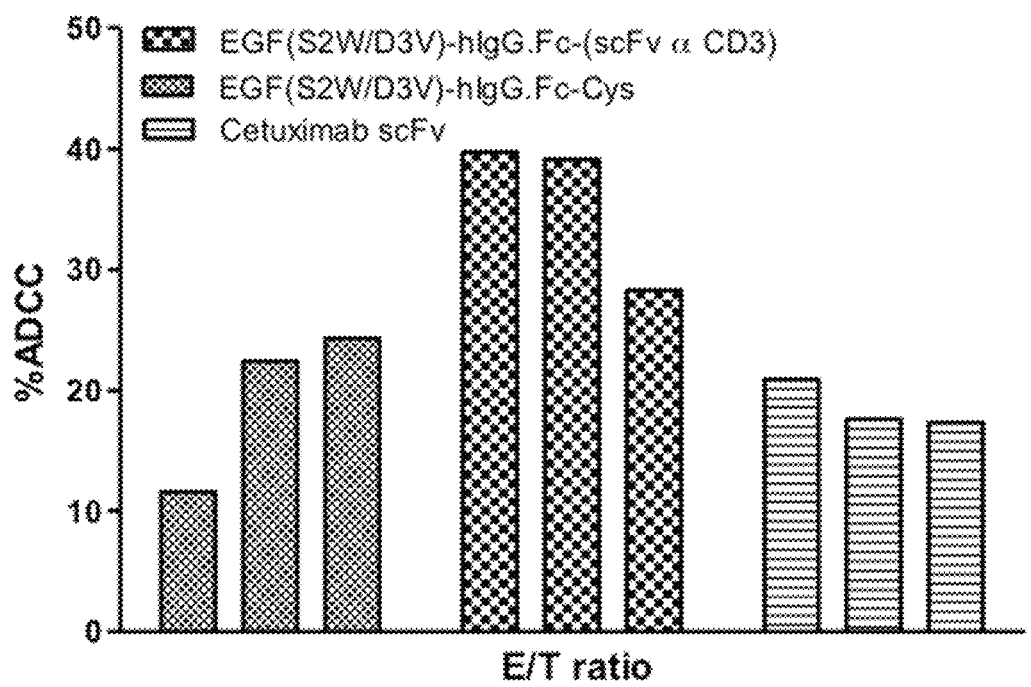

FIGS. 27A and 27B showed the degree of cytolysis of EGFR-expressing of A431 cells upon the incubation with EGF-hIgG1.Fc-Cys, EGF-hIgG1.Fc-scFv α CD3, and EGF (S2W/D3V)-IgG1.Fc-(scFv α CD3); FIGS. 27C and 27D showed the degree of cytolysis on MDA-MB-231 by human T lymphocytes from donor #56 (FIG. 27C) and #59 (FIG. 27D) upon the incubation with EGF(S2W/D3V)-IgG1.Fc-(scFv α CD3). These result indicated that EGF(S2W/D3V)-hIgG1.Fc-scFvaCD3 mediated EGFR-expressing MDA-MB-231 cells lysis by ADCC in vitro.

Figure 28A:
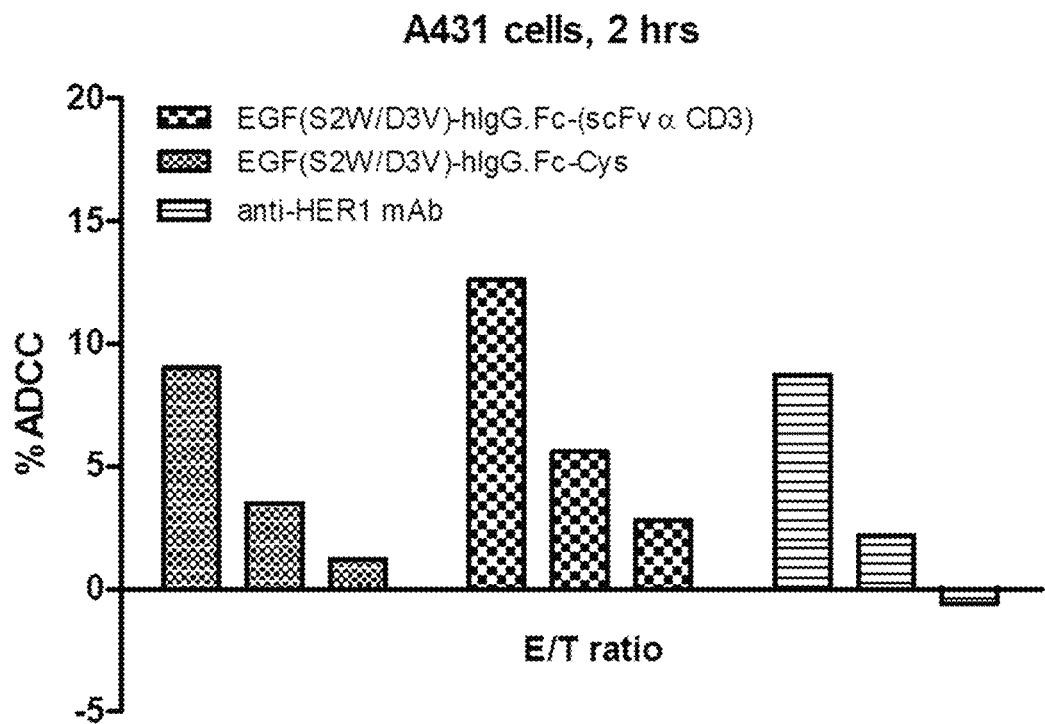
FIGS. 28A to 28C show the time course of T cell-mediated cytolysis of A431 cells upon the incubation with EGF(S2W/D3V)-IgG1.Fc-(scFv α CD3).
Figure 28B:
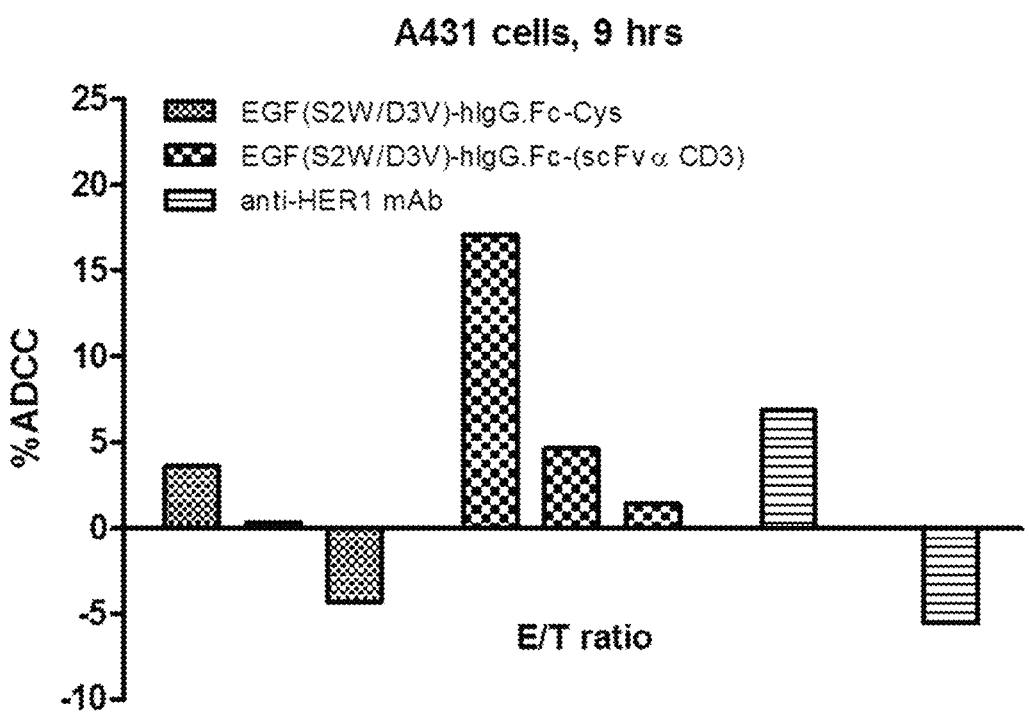
Figure 28C:
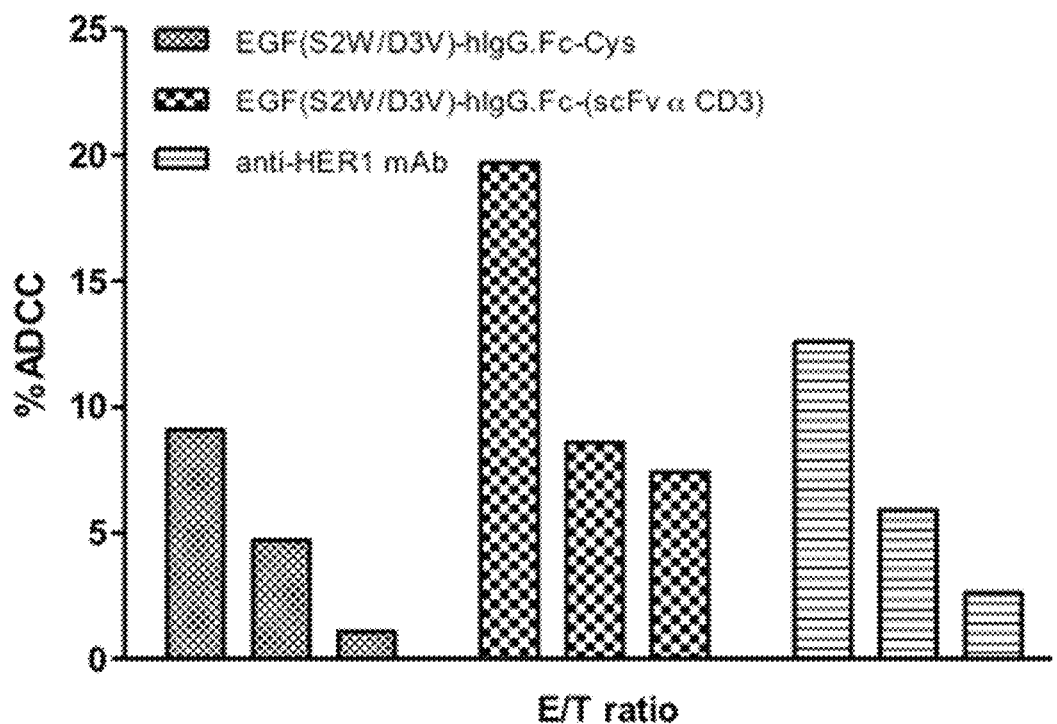

To investigate the time-dependency of cytolysis on A431 cells by human T lymphocytes upon the incubation with EGF(S2W/D3V)-IgG1.Fc-(scFv α CD3), A431 cells were incubated with 10 µg/mL EGF(S2W/D3V)-hIgG1.Fc, EGF (S2W/D3V)-hIgG1.Fc-(scFv α CD3), or anti-HER1 mAb (control) at 37° C. for 1 hour, and then mixed with human T lymphocytes isolated from human PBMC at different E:T ratios of 20, 10 or 5, and incubated for 2 (FIG. 28A), 9 (FIG. 28B), or 24 (FIG. 28C) hours. The results, as summarized in FIGS. 28A to 28C, indicated that degree of cytolysis on human T lymphocyte upon the incubation with EGF(S2W/D3V)-IgG1.Fc-(scFv α CD3) was time-dependent.

Example 32: T Cell-Mediated Cytotoxicity Assay of 2-Chain EGF(S2W/D3V)-IgG1.Fc-(scFv α PD-1) Fusion Protein on A431 Tumor Cells EGF(S2W/D3V)-hIgG1.Fc and EGF(S2W/D3V)-hIgG1.Fc-scFv α PD-1 mediated EGFR-expressing A431 cells lysis by ADCC in vitro. The assay was performed as described in the preceding Example. A431 cells were incubated with 10 µg/mL EGF(S2W/D3V)-hIgG1.Fc, EGF (S2W/D3V)-hIgG1.Fc-scFv α PD-1, or anti-HER1 mAb (control) at 37° C. for 1 hour, and then mixed with human T lymphocytes isolated from human PBMC at different E:T ratios of 20, 10 or 5, and incubated for 24 hours. ADCC were analyzed by using an aCella-TOX kit (Cell Technology Inc.)

Figure 29:
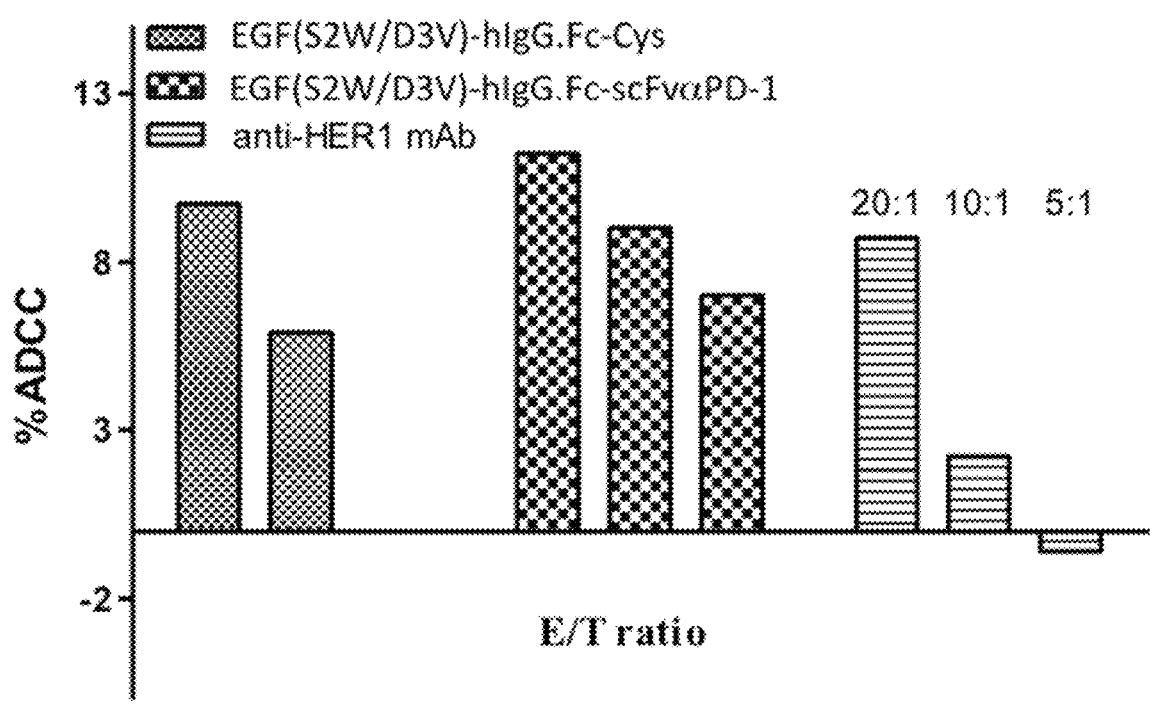
FIG. 29 shows the degree of cytolysis on A431 by human PBMCs upon the incubation with 2-chain EGFw2v3-IgG1.Fc-(scFv α PD-1).

FIG. 29 showed the degree of cytolysis on A431 by human PBMC upon the incubation with 2-chain EGFw2v3-IgG1.Fc-(scFv α PD-1).

Example 33: In Vivo Tumor Model of Recombinant 2-Chain EGFw2v3-IgG1.Fc-(scFv α PD-1) and EGFw2v3-IgG1.Fc-(scFv α CD3) Fusion Proteins Three- to four-week old NOD-SCID mice, NOD.CB17-Prkdcscid/IcrCrlBltw are obtained from BioLasco, Taipei, Taiwan. The mice are injected intraperitoneally with $1 \times 10^6$ A431 cells per mouse 2 weeks before the treatment of EGF(S2W/D3V)-hIgG.Fc-Cys, EGF(S2W/D3V)-hIgG.Fc-scFv α PD-1 (scheme 72), EGF(S2W/D3V)-hIgG.Fc-scFv α CD3, or isotype-matched control recombinant proteins. Mice are grouped into five mice per group, and administrated, intraperitoneally, with the respective protein at 5 mg/kg in 50 mL of PBS 3 times a week. At the first protein treatment, each mouse is also given $2 \times 10^7$ cells of the human PBMCs intraperitoneally. PBMCs are purified from buffy coats of blood samples from healthy donors (Taiwan Blood Service Foundation) by centrifugation over a Ficoll-Paque PLUS (GE Healthcare) density gradient and cryopreserved in 90% FBS/10% DMSO. Prior to use, the PBMCs are thawed and cultured at $2 \times 10^6$ cells/ml overnight in IMDM medium (Invitrogen) supplemented with 10% heat-inactivated FBS, 4 mM L-glutamine, 25 mM HEPES, 50 mg/ml penicillin, and 100 mg/ml streptomycin (complete IMDM medium). Tumor growth is recorded every 3 to 4 days by caliper. Mice is sacrificed on day 35 and s.c. tumors were removed, weighed, and examined.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A molecular construct comprising,
a pair of CH2-CH3 segments of an IgG Fc;
a peptide extension having a sequence of $(G_{2-4}S)_{2-8}C$ and linked to the C-terminus of one of the pair of CH2-CH3 segments;
a coupling arm linked to the C-terminus of the peptide extension via thiol-maleimide reaction occurred therebetween;
a first pair of effector elements, wherein each effector element is a drug bundle; and
a first pair of targeting elements, wherein the targeting element is a growth factor or a peptide hormone, wherein,
the effector elements are respectively linked to the C-termini of the pair of CH2-CH3 segments, and the targeting elements are respectively linked to the N-termini of the pair of CH2-CH3 segments; and
the drug bundle comprises,
a center core that is a compound having a plurality of amine groups or a polypeptide comprising a plurality of lysine (K) residues, wherein each K residue and its next K residue are separated by a filler sequence comprising glycine (G) and serine (S) residues, and the number of K residues ranges from 2 to 15;
a plurality of linking arms, each having one terminus linked to the center core by reacting with one of the amine groups of the compound or one of the K residues, and carrying a maleimide group at the free terminus thereof; and
a plurality of molecules of, a cytotoxic drug, a toll-like receptor (TLR) agonist, or a chelator complexed with a radioactive nuclide, wherein each of the molecules is linked to the center core via connecting through the linking arm by reacting with the maleimide group, and the drug bundle is linked to the coupling arm via inverse electron demand Diels-Alder (iEDDA) reaction, strain-promoted azide-alkyne click chemistry (SPAAC) reaction, or Copper (I)-catalyzed alkyne-azide cycloaddition (CuAAC) reaction occurred therebetween;
wherein the amino acid residue at the N- or C-terminus of the center core has an azide group or an alkyne group; or the amino acid residue at the N- or C-terminus of the center core is a cysteine residue, and the cysteine residue of the center core is linked with the coupling arm having an alkyne group, azide group, tetrazine group, or strained alkyne group at the free terminus of the coupling arm.

2. The molecular construct of claim 1, wherein the pair of CH2-CH3 segments is derived from human γ4 or γ1 immunoglobulin.

3. The molecular construct of claim 1, further comprising a second pair of targeting elements, wherein the second pair of targeting elements is linked, in a tandem or diabody configuration, to the N-termini of the first pair of targeting elements.

4. The molecular construct of claim 1, wherein the cytotoxic drug is auristatin, maytansine, doxorubicin, calicheamicin, or camptothecin.

5. The molecular construct of claim 1, wherein the TLR agonist is LPS, monophosphoryl lipid A, motolimod, imiquimod, resiquimod, gardiquimod, CpG DON, lipoteichoic acid, β-glucan, or zymosan.

6. The molecular construct of claim 1, wherein the chelator is DOTA, NOTA, NODA, or DTPA.

7. The molecular construct of claim 1, wherein the radioactive nuclide is $^{90}$Y, $^{111}$In, or $^{177}$Lu.

8. The molecular construct of claim 1, wherein the growth factor is epidermal growth factor (EGF), mutant EGF, epiregulin, heparin-binding epidermal growth factor (HB-EGF), VEGF-A, basic fibroblast growth factor (bFGF), or hepatocyte growth factor (HGF).

9. The molecular construct of claim 1, wherein the hapten is dinitrophenol (DNP), trinitrophenol (TNP), dansyl, penicillin, p-aminobenzoic acid, or a polypeptide having the amino acid sequence of SEQ ID No: 20.

10. The molecular construct of claim 1, wherein the peptide hormone is cholecystokinin (CCK), somastatin, or thyroid-stimulating hormone (TSH).

11. The molecular construct of claim 1, wherein,
the effector element is the drug bundle comprising the plurality of molecules of the cytotoxic drug; and
the targeting element is EGF.

* * * * *